US006710035B2

(12) United States Patent
Felgner et al.

(10) Patent No.: US 6,710,035 B2
(45) Date of Patent: *Mar. 23, 2004

(54) GENERATION OF AN IMMUNE RESPONSE TO A PATHOGEN

(75) Inventors: Philip L. Felgner, Rancho Santa Fe, CA (US); Jon Asher Wolff, Madison, WI (US); Gary H. Rhodes, Leucadia, CA (US); Robert Wallace Malone, Chicago, IL (US); Dennis A. Carson, Del Mar, CA (US)

(73) Assignees: Vical Incorporated, San Diego, CA (US); Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/452,872

(22) Filed: Dec. 2, 1999

(65) Prior Publication Data

US 2002/0198163 A1 Dec. 26, 2002

Related U.S. Application Data

(63) Continuation of application No. 08/481,919, filed on Jun. 7, 1995, now Pat. No. 6,214,804, which is a continuation of application No. 07/496,991, filed on Mar. 21, 1990, now abandoned, which is a continuation-in-part of application No. 07/467,881, filed on Jan. 19, 1990, now abandoned, which is a continuation-in-part of application No. 07/326,305, filed on Mar. 21, 1989, now abandoned.

(51) Int. Cl.[7] .................. A61K 31/70; A61K 39/00; A01N 43/04
(52) U.S. Cl. .................. 514/44; 424/184.1
(58) Field of Search .................. 514/44; 424/184.1

(56) References Cited

U.S. PATENT DOCUMENTS

| | | | |
|---|---|---|---|
| 3,931,397 A | 1/1976 | Harnden | 424/85 |
| 4,224,404 A | 9/1980 | Viza et al. | 435/2 |
| 4,394,448 A | 7/1983 | Szoka et al. | 435/172 |
| 4,689,320 A | 8/1987 | Kaji | 514/44 |
| 4,699,880 A | 10/1987 | Goldstein | 435/172.2 |
| 4,704,692 A | 11/1987 | Ladner | 364/496 |
| 4,738,927 A | 4/1988 | Taniguchi et al. | 435/243 |
| 4,761,375 A | 8/1988 | Clark | 435/240.2 |
| 4,806,463 A | 2/1989 | Goodchild et al. | 435/5 |
| 4,945,050 A | 7/1990 | Sanford et al. | 435/172.1 |
| 5,580,859 A | * 12/1996 | Felgner | 514/44 |
| 5,589,466 A | * 12/1996 | Felgner | 514/44 |
| 5,661,133 A | 8/1997 | Leiden et al. | 514/44 |
| 5,703,055 A | * 12/1997 | Felgner | 514/44 |

FOREIGN PATENT DOCUMENTS

| | | |
|---|---|---|
| CA | 1 169 793 | 6/1984 |
| EP | 0 027 662 | 4/1981 |
| EP | 187702 | 7/1986 |
| EP | 188574 | 7/1986 |
| FR | 7 781 M | 3/1970 |
| JP | 63-285738 | 11/1988 |
| JP | 1047381 | 2/1989 |
| WO | WO 93/14629 | 5/1983 |
| WO | WO 86/00930 | 2/1986 |
| WO | WO 88/05077 | 7/1988 |
| WO | WO 89/09271 | 10/1989 |
| WO | WO 90/01543 | 2/1990 |
| WO | WO 91/02805 | 3/1991 |
| WO | WO 91/07487 | 5/1991 |
| WO | WO 91/16024 | 10/1991 |
| WO | WO 97/19675 | 6/1997 |
| WO | WO 97/37966 | 10/1997 |

OTHER PUBLICATIONS

Ertl et al. (1996), Viral Immunology, vol. 9 (1).*
Yasutomi et al. (1995) J. Virol., vol. 69 (4).*
Monteil et al. (1996) Veterinary Research, vol. 27 (4–5).*
Ledley et al (1997) J. Pediatrics 110, 1–8.*
Blau et al (Nov. 2, 1995) New Eng. J. Med., 1204–1207.*
Seeger et al (1984) Proced. Natl. Acad. Sci. 81, 5849–5852.*
Robert M. Conry et al., Characterization of a messenger RNA Polynucleotide Vaccine Vector, Cancer Research 55, 1397–1400, Apr. 1, 1995.*
Nelly Kuklin et al., Induction of Mucosal Immunity against Herpes Simplex Virus by Plasmid DNA Immunization, Journal of Virology, Apr. 1997, p. 3138–3145, vol. 71, No. 4.*
Reinhold Schirmbeck et al., Nucleic Acid Vaccination Primes Hepatitis B Virus Surface Antigen–Specific Cytotoxic T Lymphocytes in Nonresponder Mice, Journal Of Virology, Oct. 1995, p. 5929–5934, vol. 69, No. 10.*
Marie–Louise Michael et al., DNA–mediated immunization to the hepatitis B surface antigen in mice: Aspects of the humoral response mimic hepatitis B viral infection in humans, Proc. Natl. Acad. Sci. USA, vol. 92, pp. 5307–5311, Jun. 1995.*

(List continued on next page.)

Primary Examiner—Deborah Crouch
(74) Attorney, Agent, or Firm—Sterne, Kessler, Goldstein & Fox, P.L.L.C.

(57) ABSTRACT

A method for delivering an isolated polynucleotide to the interior of a cell in a vertebrate, comprising the interstitial introduction of an isolated polynucleotide into a tissue of the vertebrate where the polynucleotide is taken up by the cells of the tissue and exerts a therapeutic effect on the vertebrate. The method can be used to deliver a therapeutic polypeptide to the cells of the vertebrate, to provide an immune response upon in vivo translation of the polynucleotide, to deliver antisense polynucleotides, to deliver receptors to the cells of the vertebrate, or to provide transitory gene therapy.

26 Claims, 9 Drawing Sheets

OTHER PUBLICATIONS

Heather L. Davis et al., DNA vaccine for hepatitis B: Evidence for immunogenicity in chimpanzees and comparison with other vaccines et al, Proc. Natl. Acad. Sci. USA vol. 93, pp. 7213–7218, Jul. 1996 Immunology.*

Bin Wang et al., Gene inoculation generates immune responses against human immunodeficiency virus type 1, Proc. Natl. Acad. Sci USA vol. 90, pp. 4156–4160, May 1993.*

Partial English translation of Japanese Patent Application No. 63-285738.

Anwer, K., et al., "Synergistic Effect of Formulated Plasmid and Needle–Free Injection for Genetic Vaccines," *Pharm. Res.* 16:889–895, Plenum Publishing Corp. (Jun. 1999).

Appel, J.D., et al., "Asbestos fibers mediate transformation of monkey cells by exogenous plasmid DNA," *Proc. Natl. Acad. Sci. USA* 85:7670–7674, National Academy of Sciences (Oct. 1988).

Aubin, R., et al., "Chapter 4: Polybrene/DMSO–Assisted Gene Transfer," in: *Methods in Molecular Biology. vol. 7: Gene Transfer and Expression Protocols*, E.J. Murray, Ed., Humana Press Inc., Clifton, N.J., pp. 35–43 (Apr. 1991).

Boussif, O., et al., "A versatile vector for gene and oligonucleotide transfer into cells in culture and in vivo: Polyethylenimine," *Proc. Natl. Acad. Sci. USA* 92:7297–7302, National Academy of Sciences (Aug. 1995).

Chen, S.C., et al., "Protective Immunity Induced by Oral Immunization with a Rotavirus DNA Vaccine Encapsulated in Microparticles," *J. Virol.* 72:5757–5761, American Society for Microbiology (Jul. 1998).

Chisholm, O. and Symonds, G., "Transfection of myeloid cell lines using polybrene/DMSO," *Nucl. Acids Res.* 16:2352, IRL Press Ltd. (Mar. 1988).

Coney, L., et al., "Facilitated DNA inoculation induces anti–HIV–1 immunity in vivo," *Vaccine* 12:1545–1551, Butterworth–Heinemann Ltd. (Dec. 1994).

Danielsen, M., et al., "The mouse glucocorticoid receptor: mapping of functional domains by cloning, sequencing and expression of wild–type and mutant receptor proteins," *EMBO J.* 5:2513–1522, IRL Press Ltd. (1986).

De Smedt, S.C., et al., "Cationic Polymer Based Gene Delivery Systems," *Pharm. Res.* 17:113–126, Plenum Publishing Corp. (Feb. 2000).

de Souza, S.J. and Brentani, R., "Collagen Binding Site in Collagenase Can Be Determined Using the Concept of Sense–Antisense Peptide Interactions," *J. Biol. Chem.* 267:13763–13767, American Society for Biochemistry and Molecular Biology, Inc. (Jul. 1992).

De Wet, J.R., et al., "Firefly Luciferase Gene: Structure and Expression in Mammalian Cells," *Mol. Cell. Biol.* 7:725–737, American Society for Microbiology (1987).

Desnick, R.J. and Schuchman, E.H., "Gene therapy for genetic diseases," *Acta. Paedia. Jap.* 40:191–203, Blackwell Science Ltd. (Jun. 1998).

Duguid, J.G., et al., "A Physicochemical Approach for Predicting the Effectiveness of Peptide–Based Gene Delivery Systems for Use in Plasmid–Based Gene Therapy," *Biophys. J.* 74:2802–2814, Biophysical Society (Jun. 1998).

Esposito, E., et al., "Preparation and characterization of cationic microspheres for gene delivery," *Int. J. Pharmaceutics* 189:29–41, Elsevier Science (Oct. 1999).

Felgner, P.L., et al.,"Lipofection: A highly efficient, lipid–mediated DNA–transfection procedure," *Proc. Natl. Acad. Sci. USA* 84:7413–7417, National Academy of Sciences (1987).

Fynan, E.F., et al., "DNA vaccines: Protective immunizations by parenteral, mucosal, and gene–gun inoculations," *Proc. Natl. Acad. Sci. USA* 90:11478–11482, National Academy of Sciences (Dec. 1993).

Garnett, M.C., "Gene–Delivery Systems Using Cationic Polymers," *Crit. Rev. Ther. Drug Carrier Syst.* 16:147–207, Begell House, Inc. (Mar. 1999).

Jones, D.H., et al., "Poly(DL–lactide–co–glycolide)–encapsulated plasmid DNA elicits systemic and mucosal antibody responses to encoded protein after oral administration," *Vaccine* 15:814–817, Elsevier Science Ltd. (Jun. 1997).

Kawai, S. and Nishizawa, M., "New Procedure for DNA Transfection with Polycation and Dimethyl Sulfoxide," *Mol. Cell. Biol.* 4:1172–1174, American Society for Microbiology (1984).

Kichler, A., et al. ,"Efficient DNA Transfection Mediated by the C–Terminal Domain of Human Immunodeficiency Virus Type 1 Viral Protein R," *J. Virol.* 74:5424–5431, American Society for Microbiology (Jun. 2000).

Kircheis, R., et al., "Polycation–Based DNA Complexes for Tumor–Targeted Gene Delivery in vivo," *J. Gene Med.* 1:111–120, John Wiley and Sons, Ltd. (Feb. 1999).

Klinman, D.M., et al., "Contribution of CpG Motifs to the Immunogenicity of DNA Vaccines," *J. Immunol.* 158:3635–3639, American Association of Immunologies (Apr. 1997).

Krieg, A.M., et al., "Sequence motifs in adenoviral DNA block immune activation by stipulatory CpG motifs," *Proc. Natl. Acad. Sci. USA* 95:12631–12636, National Academy of Sciences (Oct. 1998).

Kukowska–Lattallo, J., et al., "Efficient transfer of genetic material into mammalian cells using Starburst polyamidoamine dendrimers," *Proc. Natl. Acad. Sci USA* 93:4897–4902, National Academy of Sciences (May 1996).

Lemieux, P., et al., "A combination of poloxamers increases gene expression of plasmid DNA in skeletal muscle," *Gene Ther.* 7:986–991, Nature Publishing Group (Jun. 2000).

Li, J.–M., et al., "Efficient Gene Delivery to Vascular Smooth Muscle Cells Using a Nontoxic, Synthetic Peptide Vector System Targeted to Membrane Integrins: A First Step Toward the Gene Therapy of Chronic Rejection," *Transplant. Proc.* 33:589, Elsevier Science (Feb. 2001).

Liaw, J., et al., "In vivo gene delivery into ocular tissues by eye drops of poly(ethylene oxide)–poly(propylene oxide)–poly(ethylene oxide) (PEO–PPO–PEO) polymeric micelles," *Gene Ther.* 8:999–1004, Nature Publishing Group (Jul. 2001).

Lin, H., et al., "Expression of Recombinant Genes in Myocardium In Vivo After Direct Injection of DNA," *Circulation* 82:2217–2221, Lippincott Williams and Wilkins (Dec. 1990).

Liptay, S., et al., "Colon Epithelium Can Be Transiently Transfected with Liposomes, Calcium Phosphate Precipitation and DEAE Dextran in vivo," *Digestion* 59:142–147, S. Karger AG (Mar. 1998).

Lopata, M.A., et al., "High level transient expression of a chloramphenicol acetyl transferase gene by DEAE–dextran mediated DNA transfection coupled with a dimethyl sulfoxide or glycerol shock treatment," *Nucl. Acids, Res.* 12:5707–5717, IRL Press Ltd. (1984).

Luo, D., et al., "Controlled DNA Delivery Systems," *Pharm. Res.* 16:1300–1308, Plenum Publishing Corp. (Aug. 1999).

Luo, D. and Saltzman, W.M., "Synthetic DNA delivery systems," *Nat. Biotechnol.* 18:33–37, Nature Publishing Co. (Jan. 2000).

MacLaughlin, F.C., et al.,, "Chitosan and depolymerized chitosan oligomers as condensing carriers for in vivo plasmid delivery," *J. Control. Release* 56:259–272, Elsevier Science (Dec. 1998).

Manthorpe, M., et al., "Gene Therapy by Intramuscular Injection of Plasmid DNA: Studies on Firefly Luciferase Gene Expression in Mice," *Hum. Gene Ther.* 4:419–431, Mary Ann Liebert, Inc. (Aug. 1993).

Mao, H.–Q., et al., "Chitosan–DNA nanoparticles as gene carriers: synthesis, characterization and transfection efficiency," *J. Control. Release* 70:399–421, Elsevier Science (Feb. 2001).

Martin, T., et al., "Plasmid DNA Malaria Vaccine: The Potential for Genomic Integration after Intramuscular Injection," *Hum. Gene Ther.* 10:759–768, Mary Ann Liebert, Inc. (Mar. 1999).

Mumper, R.J., et al., "Polyvinyl Derivatives as Novel Interactive Polymers for Controlled Gene Delivery to Muscle," *Pharm. Res.* 13:701–709, Plenum Publishing Corp. (May 1996).

Mumper, R.J., et al., "Protective interactive noncondensing (PINC) polymers for enhanced plasmid distribution and expression in rat skeletal muscle," *J. Control. Release* 52:191–203, Elsevier Science (Mar. 1998).

Pachuk, C.J., et al., "Characterization of a new class of DNA delivery complexes formed by the local anesthetic bupivacaine," *Biochim. Biophys. Acta* 1468:20–30, Elsevier Science (Sep. 2000).

Prevec, L., et al., "Use of Human Adenovirus–based Vectors for Antigen Expression in Animals," *J. Gen. Virol.* 70:429–434, Society for General Microbiology (Feb. 1989).

Roy, K., et al., "Oral gene delivery with chitosan–DNA nanoparticles generates immunologic protection in a murine model of peanut allergy," *Nat. Med.* 5:387–391, Macmillan Magazines Ltd. (Apr. 1999).

Sanford, J.C., et al., "Delivery of Substances into Cells and Tissues Using a Particle Bombardment Process," *Partic. Sci. Tech.* 5:27–37, Hemisphere Publishing Corp. (1987).

Sompayrac, L.M. and Danna, K.J., "Efficient infection of monkey cells with DNA of simian virus 40," *Proc. Natl. Acad. Sci. USA* 78:7575–7578, National Academy of Sciences (1981).

Sureau, C., et al., "Clone Hepatitis Delta Virus cDNA Is Infectious in the Chimpanzee," *J. Virol.* 63:4292–4297, American Society for Microbiology (Oct. 1989).

Tang, D.–C., et al., "Genetic immunization is a simple method for eliciting an immune response," *Nature* 356:152–154, Macmillan Magazines Ltd. (Mar. 1992).

Venneman, M.R., "Immongenicity of Ribonucleic Acid Preparations Obtained from *Salmonella typhimurium*," *Infect. Immun.* 1:574–582, American Society for Microbiology (1970).

Wang, D., et al., "Encapsulation of plasmid DNA in biodegradable poly(D.L–lactic–co–glycolic acid) microspheres as a novel approach for immunogen delivery," *J. Control. Release* 57:9–18, Elsevier Science (Jan. 1999).

Williams, R.S., et al., "Introduction of foreign genes into tissues of living mice by DNA–coated microprojectiles," *Proc. Natl. Acad. Sci. USA* 88:2726–2730, National Academy of Sciences (Apr. 1991).

Wolff, J.A., et al., "Conditions Affecting Direct Gene Transfer into Rodent Muscle In Vivo,"*BioTechniques* 11:474–485, Eaton Publishing Co. (Oct. 1991).

Wolff, J.A., et al., "Expression of naked plasmids by cultured myotubes and entry of plasmids into T tubules and caveolae of mammalian skeletal muscle," *J. Cell. Sci.* 103:1249–1259, Company of Biologists Ltd. (Dec. 1992).

Yang, N.–S., "Gene Transfer into Mammalian Somatic Cells In Vivo," *Crit. Rev. Biotech.* 12:335–356, CRC Press, Inc. (Oct. 1992).

Youmans, A.S. and Youmans, G.P., "Factors Affecting Immunogenic Activity of Mycobacterial Ribosomal and Ribonucleic Acid Preparations," *J. Bacteriol.* 99:42–50, American Society for Microbiology (1969).

Davis, H.L., et al., "Use of Plasmid DNA for Direct Gene Transfer and Immunization," *Ann. N.Y. Acad. Sci.* 772:21–29, Springer Press (Nov. 1995).

Wright, M.J., "In vivo myocardial gene transfer: Optimization, evaluation and direct comparison of gene transfer vectors," Basic Res. Cardiol. 96:227–236, Steinkopf Verlag (May 2001).

Declaration of Bruno Picard, In the matter of the Opposition to EP 465 529, mailed Aug. 28, 2001.

English language translation of Document At79, Declaration of Bruno Pitard.

Declaration of Jean–Paul Behr, In the matter of the Opposition to EP 465 529, mailed Aug. 28, 2001.

English language translation of Document AS80, Declaration of Jean–Paul Behr.

Declaration of Benjamin Chain, In the matter of the Opposition to EP 465 529, dated Aug. 9, 2001, submitted to the European Patent Office Aug. 23, 2001.

Declaration of Charles Coutelle, In the matter of the Opposition to EP 465 529, dated Aug. 20, 2001, submitted to the European Patent Office Aug. 23, 2001.

Declaration of Ian A. Ramshaw, In the matter of the Opposition to EP 465 529, mailed Sep. 11, 2001.

Acsadi, G., et al., "Direct Gene Transfer and Expression into Rat Heart in Vivo," *The New Biologist* 3:71–81 (1991).

Adrian et al., *Mol. Cell. Biol.* 4:1712–1717 (1984).

Agadjanyan, M.G., et al., "DNA Inoculation with an HTLV–I Envelope DNA construct Elicits Immune Responses in Rabbits," *Vaccines* 94:47–53 (1994).

Alpaugh, V., "Uncovering Naked DNA," *Merck World* (1993).

Anderson, E. D. et al., "Genetic Immunization of Rainbow Trout (*Oncorhynchus mykiss*) against Infectious Hematopoietic Necrosis Virus," *Mol. Marine Biol. Biotechnol.* 5:114–122 (1996).

Anker, P. et al., "Spontaneous Release of DNA by Human Blood Lymphocytes as Shown in an in Vitro System," *Cancer Res.* 35:2375–2382 (1975).

Anker, P., et al., "The Role of Extracellular DNA in the Transfer of Information of Information from T to B Human Lymphocytes in the Course of an Immune Response," *J. Immunogen.* 7:475–481 (1980).

Anker, P., et al., "Transfert d'information de lymphocytes T `a B au cours d'une réponse immune: rôle de l'ADN extracellulaire," *Schweiz med. Wschr.* 110:1444–1446 (1980).

Anker, P., et al., "Anticorps porteurs d'allotypes humains synthétisés par des souris nues après injection de DNA relâché par des lymphocytes T humains," *Schweiz. Med. Wschr.* 112:1438–1439 (1982).

Anker, P., et al., "Nude Mice Injected with DNA Excreted by Antigen–Stimulated Human T Lymphocytes Synthesize Specific Human Antibodies," *Expl. Cell. Biol.* 53:133–136 (1984).

Ausubel, *Current Protocols in Mol. Biol.*, John Wiley & Sons, New York, §1.5.2 §§9.1.1–9.1.4 (1988).

Bains, W., *Biotechnology from A to Z*, $2^{nd}$ ed., Oxford University Press, New York, NY pp. 17–19 (1998).

Beardsley et al., *Scientific American* 261:28–30 (Nov. 1989).

Beardsley, T., "Better Than a Cure," *Scientific American* 272:88–95 (1995).

Been et al., *Cell* 47:206–216 (1986).

Benvenisty et al., *Proc. Natl. Acad. Sci. USA* 83:9551–9555 (1986).

Berge et al., *J. Pharm. Sci.* 66:1–19 (1977).

Bhoopalam et al., *Clin. Exp. Immunol.* 23:139–148 (1976).

Bouchard et al., *Virol.* 135:53–64 (1984).

Boynton et al., *Science* 240:1534–1538 (1988).

Brock et al., *Cell* 34:207–214 (1983).

Brown et al., *J. Virol.* 62:4828–4831 (Dec. 1988).

Brown et al., *Science* 232:34–47 (1986).

Burmeister et al., *Cytogen. Cell. Genet.* 46:589 (1988).

Buttrick, P.M., et al., "Behavior of Genes Directly Injected into the Rat Ear in vivo." *Circ. Res.* 70:193–198 (1992).

Chan, H.W., et al., "Molecular Cloning of Polyoma Virus DNA in *Escherichia coli*:Lambda Phage Vector System," *Science* 203:887–892 (1979).

Chelly et al., *Nature* 333:858–860 (Jun. 1988).

Chen et al., *Mol. Cell. Biol.* 7:2745–2752 (1987).

Clements–Mann, M.L., et al., "Safety and Immunogenicity of Influenza Hemagglutinin DNA Vaccine Alone or With Aluminum Adjuvant in Adult Volunteers," *American Soc. Virol. Annual Meeting* (1997).

Cohen, J., "Naked DNA Points Way to Vaccines," *Science* 259:1691–1692 (Mar. 1993).

Coney, L., et al., "Facilitated DNA Inoculation Induces Anti–HIV–1 Immunity in Vivo," *Vaccine* 12:1545–1550 (1994).

Conry, R. M., et al., "Characterization of a Messenger RNA Polynucleotide Vaccine Vector," *Cancer Research* 55:1397–1400 (1995).

Cox, G.J.M., et al., "Bovine Herpesvirus 1: Immune Responses in Mice and Cattle Injected with Plasmid DNA," *J. Virol.* 67:5664–5667 (1993).

Dalemans, W., et al., "Protection against Homologous Influenza Challenge by Genetic Immunization with SFV–RNA Encoding Flu–HA," *Ann. New York Acad. Sci.* 772:255–256 (1995).

Daniell et al., *Proc. Natl. Acad. Sci. USA* 87:88–92 (1990).

Davey, J., et al., "Location of Influenza Virus M, NP, and NS1 Proteins in Microinjected Cells," *J. Gen. Virol.* 66:2319–2334 (1985).

Davis, H.L., et al., "Direct gene transfer into mouse diaphragm," *FEBS Lett.* 333:146–150 (1993).

Davis, H.L., et al., "Direct gene transfer in skeletal muscle: plasmid DNA–based immunization against the hepatitis B virus surface antigen," *Vaccine* 12:1503–1509 (1994).

de Wet et al., *Mol. Cell. Biol.* 7:725–737 (1987).

Dean et al., *J. Cell. Biol.* 106:2159–2170 (Jun. 1988).

Deck, R.R., et al., "Characterization of humoral immune responses induced by an influenze hemagglutinin DNA vaccine," *Vaccine* 15:71–78 (Jan. 1997).

DeNoto, F.M., et al., "Human growth hormone DNA sequence and mRNA structure: possible alternative splicing," *Nucl. Acids Res.* 9:3719–3730 (1981).

Dixon, B., "The Third Vaccine Revolution," *Biotechnol.* 13:420 (May 1995).

Dolph et al., *J. Virol.* 62:2059–2066 (Jun. 1988).

Donnelly, J.J., et al., "Vaccination of Mice Against Influenza A Infection with Plasmid DNA: Heterologous and Homologous Protection," *Poster Presentation for Am. Assoc. Immunol./Clinical Immunol. Soc. Meeting*, May 20–25, 1993.

Donnelly, J.J., et al., "Polynucleotide Vaccination against Influenz," *Vaccines* 94:55–59 (1994).

Donnelly, J.J., et al., "Preclinical efficacy of a prototype DNA vaccine: Enhanced protection against antigenic drift in influenza virus," *Nat. Med.* 1:583–597 (Jun. 1995).

Drummond et al., *Nucl. Acids Res.* 13:7375 (1985).

Dubensky et al., *Proc. Natl. Acad. Sci. USA* 81:5849–5852 (1984).

Dunn, J.J., et al., *Gene* 68:259–266 (Sep. 1988).

Eibl et al., *Biophys. Chem.* 10:261–271 (1979).

Elroy–Stein et al., *Proc. Natl. Acad. Sci. USA* 86:6126–6130 (Aug. 1989).

Engelhard, V.H., "How Cells Process Antigens," *Sci. Amer.* 271:54–61 (1994).

Fainboim, L., et al., "Transfer of experimental allergic orchitis with immune RNA. Studies in vivo," *Clin. exp. Immunol.* 34:92–99 (1978).

Feitelson, M.A., et al., "A Chronic Carrierlike State Is Established in Nude Mice Injected with Cloned Hepatitis B Virus DNA," *J. Virol.* 62:1408–1415 (Apr. 1988).

Felgner et al., *Proc. Natl. Acad. Sci. USA* 84:7413–7417 (1987).

Felgner et al., *Proc. Natl. Acad. Sci. USA* 84:6730–6734 (1987).

Fields, B.N., et al., eds., *Fields Virology* 2ed., Raven Press, New York, pp. 1596–1614 (1989).

Friedman et al., *Science* 244:1275–1281 (Jun. 1989).

Fung et al., *Proc. Natl. Acad. Sci. USA* 80:353–357 (1983).

Fynan, E. F., et al., "DNA vaccines: Protective immunization by parenteral, mucosal, and gene–gun inoculations," *Proc. Natl. Acad. Sci. USA* 90:11478–11482 (1993).

Gal, D., et al., "Direct Myocardial Transfection in Two Animal Models," *Lab. Invest.* 68:18–25 (1993).

Gardner, P., and Schaffner, W., "Immunization of Adults," *New England J. Med.* 328:1252–1258 (Apr. 1993).

Gélinas, C., et al., "Tumorigenic activity of cloned polyoma virus DNA in newborn rats," *Experientia* 37:1074–1075 (1981).

Gillies et al., Biotechnol. 7:799–804 (1989).

Goldman, C.K., et al., "In vitro and in vivo gene delivery mediated by a synthetic polycationic amino polymer," *Nat. Biotech.* 15:462–466 (May 1997).

Goodfellow et al., *Nature* 341:102–103 (1989).

Gorman, C.M., et al., "Recombinant Genomes Which Express Chloramphenicol Acetyltransferase in Mammalian Cells," *Mol. Cell. Biol.* 2:1044–1051 (1982).

Gorman, C.M., et al., "The Rous *sarcoma* virus long terminal repeat is a strong promoter when introduced into a variety of eukaryotic cells by DNA–mediated transfection," *Proc. Natl. Acad. Sci. USA* 79:6777–6781 (1982).
Graves et al., *Cell* 48:615–626 (1987).
Hansen, E., et al., "Strong expression of foreign genes following direct injection into fish muscle," *FEBS Lett.* 290:7376 (1991).
Hardman, J.G., et al., eds., *Goodman & Gilman's The Pharmacological Basis of Therapeutics*, 9$^{th}$ ed., McGraw–Hill, p.8 (1996).
Harland et al., *Development* 102:837–852 (Apr. 1988).
Haynes, J.R., et al., "Gene–gun–mediated DNA Immunization Elicits Humoral, Cytotoxic, and Protective immune Responses," *Vaccines 94*:65–70 (1994).
Hentze et al., *Proc. Natl. Acad. Sci. USA* 84:6730–6734 (1987).
Hoffman et al., *Neuron* 2:1019–1029 (Jan. 1989).
Hoffman et al., *Science* 254:1455–1456 (1991).
Hoffman, S.L., et al., "Protection against malaria by immunization with a *Plasmodium yoelii* circumsporozoite protein nucleic acid vaccine," *Vaccine* 12:1529–1533 (1994).
Holt et al., *Neuron* 4:203–214 (1990).
Huang et al., *J. Virol.* 50:417–424 (1984).
Israel, M.A., et al., "Molecular Cloning of Polyoma Virus DNA in *Escherichia coli*: Plasmid Vector System," *Science* 203:883–887 (1979).
Israel, M., et al., "Biological activity of polyoma viral DNA in mice and hamsters," *J. Virol.* 29:990–996 (1979).
Jacherts, D., and Drescher, J., "Antibody Response in Rhesus Monkeys and Guinea Pigs to Inoculation with RNA Derived from Antigenetically Stimulated Cell–Free Systems," *J. Immunol.* 104:746–752 (1970).
Jachertz, D., and Egger, M., "Treatment of P815 Mastocytoma in DBA/2 Mice with RNA," *J. Immunogen.* 1:355–362 (1974).
Jachertz, D., et al., "Information carried by the DNA released by antigen–stimulated lymphocytes," *Immunol.* 37:753–763 (1979).
Jiao, S., et al., "Direct Gene Transfer into Nonhuman Primate Myofibers In Vivo," *Hum. Gen. Ther.* 3:21–33 (Feb. 1992).
Jiao, S., et al., "Particle Bombardment–Mediated Gene Transfer and Expression in Rat Brain Tissues," *Biotechnol.* 11:497–502 (1993).
Johanning, F.W., et al., "A *sindbis* virus mRNA polynucleotide vector achieves prolonged and high level heterologous gene expression in vivo," *Nucl. Acids Res.* 23:1495–1501 (1995).
Johnston et al., *Science* 240:1538–1541 (1968).
Kabnick et al., *Mol. and Cell. Biol.* 8:3244–3250 (1988).
Kaneda et al., *Science* 243:375–378 (Jan. 1989).
Kitsis, R.N., et al., "Hormonal modulation of a gene injected into rat heart in vivo," *Proc. Natl. Acad. Sci. USA* 88:4138–4142 (1991).
Klemenz et al., *EMBO J.* 4:2053–2060 (1985).
Koenig et al., "The Complete Sequency of Dystrophin Predicts a Rod–Shaped Cytoskeletal Protein," *Cell* 53:219–226 (Apr. 1988).
Kozak et al., *Nucl. Acids Res.* 15:8125 (1987).
Kreig et al., *Nucl. Acids Res.* 12:7057–7070 (1984).
Krieg, A.M., et al., "Sequence motifs in adenoviral DNA block immune activation by stimulatory CpG motifs," *Proc. Natl. Acad. Sci. USA* 95:12631–12636 (Oct. 1998).

Kruczek, I., and Doerfler, W., "Expression of the chloramphenicol acetyltransferase gene in mammalian cells under the control of adenovirus type 12 promoters: Effect of promoter methylation on gene expression," *Proc. Natl. Acad. Sci. USA* 80:7586–7590 (1983).
Kuklin, N., et al., "Induction of Mucosal Immunity against Herpes Simplex Virus by Plasmid DNA Immunization," *J. Virol.* 71:3138–3145 (1997).
Laub, O., et al., "Synthesis of Hepatitis B Surface Antigen in Mammalian Cells: Expression of the Entire Gene and the Coding Region," *J. Virol.* 48:271–280 (1983).
Lewin, B., *Genes IV*, Oxford University Press, pp. 178 (1990).
Lin, H., et al., "Expression of Recombinant Genes in Myocardium In Vivo After Direct Injection of DNA," *Circulation* 82:2217–2221 (1990).
Loyter et al., *Exp. Cell Res.* 139:223–234 (1982).
Magee et al., *Cancer Res.* 38:1173–1176 (1978).
Malone et al., *Proc. Natl. Acad. Sci. USA* 86:6077–6081 (Aug. 1989).
Mandi, C.W., et al., " In vitro–synthesized infectious RNA as an attenuated live vaccine in a flavivirus model," *Nat. Med.* 4:1438–1440 (Dec. 1998).
Mannino et al., *Biotechniques* 6:682–690 (Jun.–Aug. 1988).
McCrae et al., *Eur. J. Biochem.* 116:467–470 (1981).
Mosier et al., *Nature* 335:256–259 (Sep. 1988).
Muesing et al., *Cell* 48:691 (1987).
Mullner et al., *Cell* 53:815–825 (Jun. 1988).
Nakatani et al., *Biotechnology* 7:805–810 (1989).
Namikawa et al., *Science* 242:1684–1686 (Dec. 1988).
New England Biolabs 1986/87 Catalog, 32 Tozer Rd., Beverly, MA 01915–0990 USA, p. 45.
Nicolau et al., *Proc. Natl. Acad. Sci. USA* 80:1068–1072 (1983).
Nicolau, C., et al., "Liposomes as Carriers for in Vivo Gene Transfer and Expression," *Meth. Enzymol.* 149:157–176 (1987).
Norton et al., *Mol. Cell Biol.* 5:281–290 (1985).
Ostro et al., *Nature* 274:921–923 (1979).
Oudrhiri, N., et al., "Gene transfer by guanidine–cholestrol cationic lipids into airway epithelial cells in vitro and in vivo," *Proc. Natl. Acad. Sci. USA* 94:1651–1656 (Mar. 1997).
Parks et al., *J. Virol.* 60:376–384 (1986).
Pelletier et al., *Nature* 334320–325 (Jul. 1988).
Potter, C.W., "Inactivated Influenza Virus Vaccine," in *Basic and Applied Influenza Research*, Beare, A.S., ed., CRC Press, Boca Raton, FL, pp. 119–151 (1982).
Poyet et al., *Mol. Endocrinol.* 3:1961–1968 (Dec. 1989).
Price et al., *Proc. Natl. Acad. Sci. USA* 84: 156–160 (1987).
Qiu, P., et al., "Gene gun delivery of mRNA in situ results in efficient transgene expression and genetic immunization," *Gene Ther.* 3:262–268 (1996).
Rao et al., *Mol. Cell. Biol.* 8:284 (Jan. 1988).
Raz, E., et al., "Systematic immunological effects of cytokine genes injected into skeletal muscle," *Proc. Natl. Acad. Sci. USA* 90:4523–4527 (1993).
Raz, E., et al., "Intradermal gene immunization: The possible role of DNA uptake in the induction of cellular immunity to viruses," *Proc. Natl. Acad. Sci. USA* 91:9519–9523 (1994).
Rhodes, G.H., et al., "Characterization of Humoral Immunity after DNA Injection" *Dev. Biol. Stand.* 82:229–236 (1994).

Robinson et al., *Science* 22:417–419 (1984).

Robinson, H.L., et al., "Protection against a lethal influenza virus challenge by immunization with a haemagglutinin–expressing plasmid DNA," *Vaccine* 11:957–960 (1993).

Robinson, H.L., et al., "Use of Direct DNA Inoculations to Elicit Protective Immune Responses," *Abstract of papers*, p. 92 (Cold Spring Harbor Laboratory 1994).

Rommens et al., *Science* 245:1059–1065 (Sep. 1989).

Rosenberg, S.A., et al., "Biological Activity of Recombinant Human Interleukin–2 Produced in *Escherichia coli*," *Science* 223:1412–1415 (1984).

Ross et al., *Mol. Biol. Med.* 5:1–14 (Feb. 1988).

Sato, Y., et al., "Immunostimulatory DNA Sequences Necessary for Effective Intradermal Gene Immunization," *Science* 273:352–354 (Jul. 1996).

Satz, M.L., et al., "Mechanism of immune transfer by RNA extracts," *Mol. Cell. Biochem.* 33:105–113 (1980).

Sedegah, M., et al., "Protection against malaria by immunization with plasmid DNA encoding circumsporozoite protein," *Proc. Natl. Acad. Sci. USA* 91:9866–9870 (1994).

Seeger, C., et al., "The cloned genome of ground squirrel hepatitis virus is infectious in the animal," *Proc. Natl. Acad. Sci. USA* 81:5849–5852 (1984).

Selden et al., *Mol. Cell. Biol.* 6:3173–3179 (1986).

Selden et al., *Proc. Natl. Acad. Sci. USA* 85:8241–8245 (Nov. 1988).

Sell, S., and Mendelsohn, J., "Transfer of Specific Immunity With RNA," *Arch. Path. Lab Med.* 102:217–222 (1978).

Shaw et al., *Cell* 46:659–667 (1986).

Sizemore, D.R., et al., "Attenuated Shigella as a DNA Delivery Vehicle for DNA–Meidated Immunization," *Science* 270:299–302 (1995).

Soares, M.B., et al., "RNA–Mediated Gene Duplication: the Rat Preproinsulin I Gene Is a Functional Retroposon," *Mol. Cell. Biol.* 5:2090–2103 (1985).

Sol, C.J.A., and van der Noordaa, J., "Oncogenecity of SV40 DNA in the Syrian Hamster," *J. Gen. Virol.* 37:635–638 (1977).

Spooner, R.A., et al., "DNA vaccination for cancer treatment," *Gene Ther.* 2:173–180 (1995).

Stamatatos et al., *Biochemistry* 27:3917–3925 (May 1988).

Straubinger et al., *Methods in Enzymology* 101:512–527 (1983).

Taniguchi, T., et al., "Structure and expression of a cloned cDNA for human interleukin–2," *Nature* 302:305–310 (1983).

Taylor, J., et al., "Recombinant fowlpox virus inducing protective immunity in non–avian species," *Vaccine* 6:497–503 (Dec. 1988).

Travis, J., "Tracing the Immune System's Evolutionary History," *Science* 261:164–165 (1993).

Tripathy, S. K., et al., "Long–term expression of erythropoietin in the systemic circulation of mice after intramuscular injection of a plasmid DNA vector," *Proc. Natl. Acad. Sci. USA* 93:10876–10880 (1996).

Ulmer, J.B., et al., "Heterologous Protection Against Influenza by Injection of DNA Encoding a Viral Protein," *Science* 259:1745–1749 (1993).

Ulmer, J.B., et al., "Protective Immunity by intramuscular injection of low doses of influenza virus DNA vaccines," *Vaccine* 12:1541–1544 (1994).

Ulmer, J.B., et al., "DNA vaccines," *Curr. Opin. Immunol.* 8:531–536 (1996).

Valerio et al., *Gene* 31:147–153 (1984).

von Harsdorf, R., et al., "Gene Injection into Canine Myocardium as a Useful Model for Studying Gene Expression in the Heart of Large Mammals," *Circ. Res.* 72:688–695 (1993).

Wang, B., et al., "Gene inoculation generates immune responses against human immunodeficiency virus type 1," *Proc. Natl. Acad. Sci. USA* 90:4156–4160 (1993).

Wang, C., et al., "Direct Gene Delivery of Human Tissue Kallikrein Reduces Blood Pressure in Spontaneously Hypertensive Rats," *J. Clin. Invest.* 95:1710–1716 (1995).

Wang, C.–Y., and Huang, L., "ph–sensitive immunoliposomes mediate target–cell–specific delivery and controlled expression of a foreign gene in mouse," *Proc. Natl. Acad. Sci. USA* 84:7851–7855 (1987).

Ward et al., *Nature* 341:544–546 (Oct. 1989).

Watkins et al., *Nature* 6176:863–866 (Jun. 1988).

Webster, R.G., et al., "Protection of ferrets against influenza challenge with a DNA vaccine to the haemagglutinin," *Vaccine* 12:1495–1498 (1994).

Weeratna, R., et al., "Reduction of Antigen Expression from DNA Vaccines by Coadministered Oligodeoxynucleotides," *Antisense & Nucl. Acid Drug Develop.* 8:351–356 (Aug. 1998).

Whalen, R., et al., "DNA–mediated immunization and the energetic immune response to hepatitis B surface antigen," *Clin. Immunol. Immunopathol.* 75:1–12 (1995).

Wickner et al., *Science* 230:400–407 (1985).

Will, H., et al., "Cloned HBV DNA causes hepatitis in chimpanzees," *Nature* 299:740–742 (1982).

Will, H., et al., "Infectious hepatitis B virus from cloned DNA of known nucleotide sequence," *Proc. Natl. Acad. Sci. USA* 82:891–895 (1985).

Wolff, J.A. et al., "Direct Gene Transfer into Mouse Muscle in Vivo," *Science* 247:1465–1468 (Mar. 1990).

Wu et al., *J. Biol. Chem.* 263:14621–14624 (1986).

Wu et al., *J. Biol. Chem.* 264:16985–16987 (Oct. 1989).

Wynshaw–Boris, A., et al., "Identification of a cAMP Regulatory Region in the Gene for Rate Cytosolic Phosphoenolpyruvate Carboxykinase (GTP)" *J. Biol. Chem.* 259:12161–12169 (1984).

Xiang, Z., et al., "Vaccination with a Plasmid Vector Carrying the Rabies Virus Glycoprotein Gene Induces Protective Immunity against Rabies Virus," *Virol.* 199:132–140 (1994).

Xiang, Z., et al., "Manipulation of the Immune Response to a Plasmid–Encoded Viral Antigen by Coinoculation with Plasmids Expressing Cytokines," *Immunity* 2:129–135 (1995).

Xu, D., et al., "Genetic vaccination against leishmaniasis," *Vaccine* 12:1534–1536 (1994).

Yakubov et al., *Proc. Natl. Acad. Sci. USA* 86:6454–6458 (Sep. 1989).

Yang, J. P., et al., "Direct Gene transfer to mouse melanoma by intratumor injection of free DNA," *Gene Ther.* 3:542–548 (1996).

Yankauckas, M.A., et al., "Long–Term Anti–Nucleoprotein Cellular and Humoral Immunity is Induced by Intramuscular Injection of Plasmid DNA Containing NP Gene," *DNA Cell Biol.* 12:771–776 (1993).

Zhou, X., et al., "Self–replicating Semliki Forest virus RNA as recombinant vaccine," *Vaccine* 12:1510–1513 (1994).

Dialog File 351, Accession No. 67–04439H/196800, Derwent WPI English language abstract for French Patent No. 7 781 M, Document No. AL1.

Kodama, K., et al., "Induction of IgM memory with RNA from the spleens of immunized mice," *Immunology* 44:535–542, Blackwell Scientific Publications (1981).

Kodama, K., et al., "Cells Participating in Immunologic Memory Induced with RNA from the Spleens of Immunized Mice," *Microbiol. Immunol.* 28:611–618, Japanese Society for Bacteriology (1984).

Lopata, M.A., et al., "High level transient expression of a chloramphenicol acetyl transferase gene by DEAE–dextran mediated DNA transfection coupled with a dimethyl sulfoxide or glycerol shock treatment," *Nucl. Acids Res.* 12:5707–5717, IRL Press Limited (1984).

Mitsuhashi, S., et al., "Ribonucleic Acid in the Immune Response," *Mol. Cell. Biochem.* 20:131–147, Dr. W. Junk b.v. Publishers (1978).

Miura, T., et al., "Acceleration of Allogeneic Antitumor Immunity with Immune RNA *in Vitro* and T–Cell Suppression by L1210 Tumor Bearer Spleen Cells," *Cancer Res.* 41:383–389, American Association For Cancer Research (1981).

Saito, K., et al., "Serial Transfers of Immunity through Immune RNA," *Japan. J. Microbiol.* 13:122–124, Japan Bacteriology Society (1969).

Slomski, R., and Latos, A.M., "Studies of Interaction of Immune RNA with Normal Spleen Cells," *Mol. Cell. Biochem.* 17:85–88, Dr. W. Junk b.v. Publishers (1977).

Slomski, R., and Latos, A.M., "Uptake of Immune RNA by Normal Mouse Spleen Cells," *Mol. Cell. Biochem.* 24:15–20, Dr. W. Junk b.v. Publishers (1979).

Sussman, D.J., and Milman, G., "Short–Term, High–Efficiency Expression of Transfected DNA," *Mol. Cell. Biol.* 4:1641–1643, American Society for Microbiology (1984).

Yamaguchi, N., et al., "Establishment of Immunologic Memory by Immune RNA. Effect of Inhibitors of Nucleic Acid Synthesis," *Jpn. J. Bacteriol.* 30:172, Japanese Society for Bacteriology (1975).

Yang, S.–F., and Niu, M.C., "Albumin synthesis in mouse uterus in response to liver mRNA," *Proc. Natl. Acad. Sci. USA* 74:1894–1898, National Academy of Sciences (1977).

Unverified English language translation of Yamaguchi, N., et al., "Establishment of Immunologic Memory by Immune RNA. Effect of Inhibitors of Nucleic Acid Synthesis," *Jpn. J. Bacteriol.* 30:172, Japanese Society for Bacteriology (1975) (Document AR85).

Felgner, P. L., and Ringold, G. M., "Cationic lipsome–mediated transfection," Nature 337:387–388, Macmillan Journals Ltd. (1989).

Felgner, P. L., "Particulate systems and polymers for in vitro and in vivo delivery of polynucleotides," *Adv. Drug Deliv. Rev.* 5;163–187, Elsevier Science B.V. (1990).

Rhodes, G., et al., "Intramuscular Injection of an Expansion Vector Containing the Gene for HIV gp 120 Induces Antibodies to the gp 120 Protein," *Int'l. Conf AIDS* Abs. No. 1048, (1990).

Farber, F. E., et al., "Optimal Conditions for Uptake of Exogenous DNA by Chinese Hamster Lung Cells Deficient in Hypoxanthine–Guanine Phosphoribosyltransferase," *Biochim. Biophys. Acta* 390:298–311, Elsevier Scientific Publishing Company (1975).

Kawai, S., and Nishizawa, M., "New Procedure for DNA Transfection with Polycation and Dimethyl Sulfoxide," *Mol. Cell. Biol.* 4:1172–1174, American Society for Microbiology (1984).

MacLaughlin, F. C., et al., "Chitosan and depolymerized chitosan oligomers as condensing carriers for in vivo plasmid delivery,"*J. Control. Release* 56:259–272, Elsevier Science B.V. (1998).

Wolff, J. A., et al., "Direct Gene Transfer Into Mouse Muscle In Vivi," *J. Cell Biochem Suppl.* 14A:378 (Abstract D 434), Wiley–Liss (1990).

Kodama, K., et al., "Induction of Igm memory with RNA from the spleens of immunized mice," *Immunology* 44:535–542, Blackwell Scientific Publications (1981).

Kodama, K., et al., "Cells Participating in Immunologic Memory Induced with RNA from the Spleens of Immunized Mice," *Microbiol. Immunol.* 28:611–618, Japanese Society for Bacteriology (1984).

Lopata, M. A., et al., "High level transient expression of a chloramphenicol acetyl transferase gene by DEAE–dextran mediated DNA transfection coupled with a dimethyl sulfoxide or glycerol shock treatment," *Nucl. Acids Res.* 12:5707–5717, IRL Press Limited (1984).

Mitsuhashi, S., et al., "Ribonucleic Acid in the Immune Response," *Mol. Cell. Biochem.* 20:131–147, Dr. W. Junk b.v. Publishers (1978).

Miura, T., et al., "Acceleration of Allogenic Antitumor Immunity with Immune RNA in Vitro and T–Cell Suppression by L1210 Tumor Bearer Spleen Cells," *Cancer Res.* 41:383–389, American Association For Cancer Research (1981).

Saito, K., et al., "Serial Transfers of Immunity through Immune RNA," *Japan. aj. amicrobiol.* 13:122–124, Japan Bacteriology Society (1969).

Slomski, R., and Latos, A. M., "Studies of Interaction of Immune RNA with Normal Spllen Cells," *Mol. Cell. Biochem.* 17:85–88, Dr. W. Junk b.v. Publishers (1977).

Slomski, R., and Latos, A. M., "Uptake of Immune RNA by Normal Mouse Spleen Cells," *Mol.mCell. Biochem.* 24:15–20, Dr. W. Junk b.v. Publishers (1979).

Sussman, D. J., and Milman, G., "Short–Term, High–Efficiency Expression of Transfected DNA," *Mol. Cell. Biol.* 4:1641–1643, American Society for Microbiology (1984).

Yamaguchi, N., et al., "Establishment of Immunolgic Memory by Immune RNA. Effect of Inhibitors of Nucleic Acid Synthesis," *Jpn. J. Bacteriol.* 30:172, Japanese Society for Bacteriology (1975).

Yang, S.–F., and Niu, M. C., "Albumin synthesis in mouse uterus in response to liver mRNA," *Proc. Natl. Acad. Sci. USA* 74:1894–1898, National Academy of Sciences (1977).

Univerified English language translation of Yamaguchi, N., et al., "Establishment of Immunologic Memory by Immune RNA. Effect of Inhibitors of Nucleic Acid Synthesis," *Jpn. J. Bacteriol.* 30;172, Japanese Society for Bacteriology (1975) (Document AR85).

* cited by examiner

GENERATION OF AN IMMUNE RESPONSE TO A PATHOGEN

This application is a continuation of U.S. application Ser. No. 08/481,919, filed Jun. 7, 1995, now U.S. Pat. No. 6,214,804 presently pending, which is a continuation of U.S. application Ser. No. 07/496,991, filed Mar. 21, 1990 (now abandoned), which is a continuation-in-part of U.S. application Ser. No. 07/467,881, filed Jan. 19, 1990 (now abandoned), which is a continuation-in-part of U.S. application Ser. No. 07/326,305, filed Mar. 21, 1989 now abandoned. Each of the foregoing disclosures is fully incorporated herein by reference.

BACKGROUND OF THE INVENTION

The present invention relates to introduction of naked DNA and RNA sequences into a vertebrate to achieve controlled expression of a polypeptide. It is useful in gene therapy, vaccination, and any therapeutic situation in which a polypeptide should be administered to cells in vivo.

Current research in gene therapy has focused on "permanent" cures, in which DNA is integrated into the genome of the patient. Viral vectors are presently the most frequently used means for transforming the patient's cells and introducing DNA into the genome. In an indirect method, viral vectors, carrying new genetic information, are used to infect target cells removed from the body, and these cells are then re-implanted. Direct in vivo gene transfer into postnatal animals has been reported for formulations of DNA encapsulated in liposomes and DNA entrapped in proteoliposomes containing viral envelope receptor proteins (Nicolau et al., *Proc. Natl. Acad Sci USA* 80:1068–1072 (1983); Kaneda et al., *Science* 243:375–378 (1989); Mannino et al., *Biotechniques* 6:682–690 (1988). Positive results have also been described with calcium phosphate co-precipitated DNA (Benvenisty and Reshef Proc. *Natl. Acad Sci USA* 83:9551–9555 (1986)).

The clinical application of gene therapy, as well as the utilization of recombinant retrovirus vectors, has been delayed because of safety considerations. Integration of exogenous DNA into the genome of a cell can cause DNA damage and possible genetic changes in the recipient cell that could predispose to malignancy. A method which avoids these potential problems would be of significant benefit in making gene therapy safe and effective.

Vaccination with immunogenic proteins has eliminated or reduced the incidence of many diseases; however there are major difficulties in using proteins associated with other pathogens and disease states as immunogens. Many protein antigens are not intrinsically immunogenic. More often, they are not effective as vaccines because of the manner in which the immune system operates.

The immune system of vertebrates consists of several interacting components. The best characterized and most important parts are the humoral and cellular (cytolytic) branches. Humoral immunity involves antibodies, proteins which are secreted into the body fluids and which directly recognize an antigen. The cellular system, in contrast, relies on special cells which recognize and kill other cells which are producing foreign antigens. This basic functional division reflects two different strategies of immune defense. Humoral immunity is mainly directed at antigens which are exogenous to the animal whereas the cellular system responds to antigens which are actively synthesized within the animal.

Antibody molecules, the effectors of humoral immunity, are secreted by special B lymphoid cells, B cells, in response to antigen. Antibodies can bind to and inactivate antigen directly (neutralizing antibodies) or activate other cells of the immune system to destroy the antigen.

Cellular immune recognition is mediated by a special class of lymphoid cells, the cytotoxic T cells. These cells do not recognize whole antigens but instead they respond to degraded peptide fragments thereof which appear on the surface of the target cell bound to proteins called class I major histocompatibility complex (MHC) molecules. Essentially all nucleated cells have class I molecules. It is believed that proteins produced within the cell are continually degraded to peptides as part of normal cellular metabolism. These fragments are bound to the MHC molecules and are transported to the cell surface. Thus the cellular immune system is constantly monitoring the spectra of proteins produced in all cells in the body and is poised to eliminate any cells producing foreign antigens.

Vaccination is the process of preparing an animal to respond to an antigen. Vaccination is more complex than immune recognition and involves not only B cells and cytotoxic T cells but other types of lymphoid cells as well. During vaccination, cells which recognize the antigen (B cells or cytotoxic T cells) are clonally expanded. In addition, the population of ancillary cells (helper T cells) specific for the antigen also increase. Vaccination also involves specialized antigen presenting cells which can process the antigen and display it in a form which can stimulate one of the two pathways.

Vaccination has changed little since the time of Louis Pasteur. A foreign antigen is introduced into an animal where it activates specific B cells by binding to surface immunoglobulins. It is also taken up by antigen processing cells, wherein it is degraded, and appears in fragments on the surface of these cells bound to Class II MHC molecules. Peptides bound to class II molecules are capable of stimulating the helper class of T cells. Both helper T cells and activated B cells are required to produce active humoral immunization. Cellular immunity is thought to be stimulated by a similar but poorly understood mechanism.

Thus two different and distinct pathways of antigen processing produce exogenous antigens bound to class II MHC molecules where they can stimulate T helper cells, as well as endogenous proteins degraded and bound to class I MHC molecules and recognized by the cytotoxic class of T cells.

There is little or no difference in the distribution of MHC molecules. Essentially all nucleated cells express class I molecules whereas class II MHC proteins are restricted to some few types of lymphoid cells.

Normal vaccination schemes will always produce a humoral immune response. They may also provide cytotoxic immunity. The humoral system protects a vaccinated individual from subsequent challenge from a pathogen and can prevent the spread of an intracellular infection if the pathogen goes through an extracellular phase during its life cycle; however, it can do relatively little to eliminate intracellular pathogens. Cytotoxic immunity complements the humoral system by eliminating the infected cells. Thus effective vaccination should activate both types of immunity.

A cytotoxic T cell response is necessary to remove intracellular pathogens such as viruses as well as malignant cells. It has proven difficult to present an exogenously administered antigen in adequate concentrations in conjunction with Class I molecules to assure an adequate response. This has severely hindered the development of vaccines against tumor-specific antigens (e.g., on breast or colon cancer cells), and against weakly immunogenic viral proteins (e.g., HIV, Herpes, non-A, non-B hepatitis, CMV and EBV).

It would be desirable to provide a cellular immune response alone in immunizing against agents such as viruses for which antibodies have been shown to enhance infectivity. It would also be useful to provide such a response against both chronic and latent viral infections and against malignant cells.

The use of synthetic peptide vaccines does not solve these problems because either the peptides do not readily associate with histocompatibility molecules, have a short serum half-life, are rapidly proteolyzed, or do not specifically localize to antigen-presenting monocytes and macrophages. At best, all exogenously administered antigens must compete with the universe of self-proteins for binding to antigen-presenting macrophages.

Major efforts have been mounted to elicit immune responses to poorly immunogenic viral proteins from the herpes viruses, non-A, non-B hepatitis, HIV, and the like. These pathogens are difficult and hazardous to propagate in vitro. As mentioned above, synthetic peptide vaccines corresponding to viral-encoded proteins have been made, but have severe pitfalls. Attempts have also been made to use vaccinia virus vectors to express proteins from other viruses. However, the results have been disappointing, since (a) recombinant vaccinia viruses may be rapidly eliminated from the circulation in already immune individuals, and (b) the administration of complex viral antigens, may induce a phenomenon known as "antigenic competition," in which weakly immunogenic portions of the virus fail to elicit an immune response because they are out-competed by other more potent regions of the administered antigen.

Another major problem with protein or peptide vaccines is anaphylactic reaction which can occur when injections of antigen are repeated in efforts to produce a potent immune response. In this phenomenon, IgE antibodies formed in response to the antigen cause severe and sometimes fatal allergic reactions.

Accordingly, there is a need for a method for invoking a safe and effective immune response to this type of protein or polypeptide. Moreover, there is a great need for a method that will associate these antigens with Class I histocompatibility antigens on the cell surface to elicit a cytotoxic T cell response, avoid anaphylaxis and proteolysis of the material in the serum, and facilitate localization of the material to monocytes and macrophages.

A large number of disease states can benefit from the administration of therapeutic peptides. Such peptides include lymphokines, such as interleukin-2, tumor necrosis factor, and the interferons; growth factors, such as nerve growth factor, epidermal growth factor, and human growth hormone; tissue plasminogen activator; factor VIII:C; granulocyte-macrophage colony-stimulating factor; erythropoietin; insulin; calcitonin; thymidine kinase; and the like. Moreover, selective delivery of toxic peptides (such as ricin, diphtheria toxin, or cobra venom factor) to diseased or neoplastic cells can have major therapeutic benefits. Current peptide delivery systems suffer from significant problems, including the inability to effectively incorporate functional cell surface receptors onto cell membranes, and the necessity of systemically administering large quantities of the peptide (with resultant undesirable systemic side effects) in order to deliver a therapeutic amount of the peptide into or onto the target cell.

These above-described problems associated with gene therapy, immunization, and delivery of therapeutic peptides to cells are addressed by the present invention.

SUMMARY OF THE INVENTION

Figure 1:
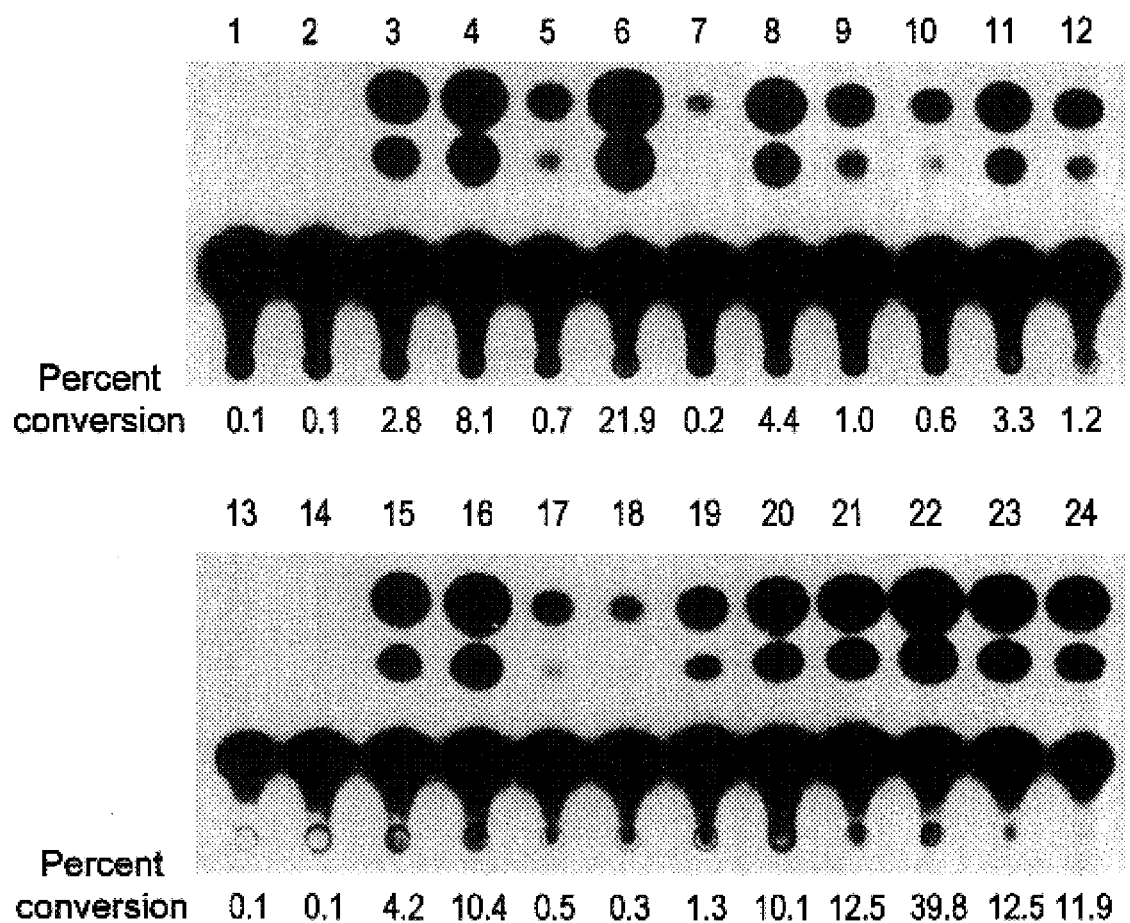
FIG. 1 comprises autoradiograms of chromatographic studies showing the expression of the CAT gene in mouse muscle.

The present invention provides a method for delivering a pharmaceutical or immunogenic polypeptide to the interior of a cell of a vertebrate in vivo, comprising the step of introducing a preparation comprising a pharmaceutically acceptable injectable carrier and a naked polynucleotide operatively coding for the polypeptide into the interstitial space of a tissue comprising the cell, whereby the naked polynucleotide is taken up into the interior of the cell and has an immunogenic or pharmacological effect on the vertebrate. Also provided is a method for introducing a polynucleotide into muscle cells in vivo, comprising the steps of providing a composition comprising a naked polynucleotide in a pharmaceutically acceptable carrier, and contacting the composition with muscle tissue of a vertebrate in vivo, whereby the polynucleotide is introduced into muscle cells of the tissue. The polynucleotide may be an antisense polynucleotide. Alternatively, the polynucleotide may code for a therapeutic peptide that is expressed by the muscle cells after the contacting step to provide therapy to the vertebrate. Similarly, it may code for an immunogenic peptide that is expressed by the muscle cells after the contacting step and which generates an immune response, thereby immunizing the vertebrate.

One particularly attractive aspect of the invention is a method for obtaining long term administration of a polypeptide to a vertebrate, comprising the step of introducing a naked DNA sequence operatively coding for the polypeptide interstitially into tissue of the vertebrate, whereby cells of the tissue produce the polypeptide for at least one month or at least 3 months, more preferably at least 6 months. In this embodiment of the invention, the cells producing the polypeptide are nonproliferating cells, such as muscle cells.

Another method according to the invention is a method for obtaining transitory expression of a polypeptide in a vertebrate, comprising the step of introducing a naked mRNA sequence operatively coding for the polypeptide interstitially into tissue of the vertebrate, whereby cells of the tissue produce the polypeptide for less than about 20 days, usually less than about 10 days, and often less than 3 or 5 days. For many of the methods of the invention, administration into solid tissue is preferred.

One important aspect of the invention is a method for treatment of muscular dystrophy, comprising the steps of introducing a therapeutic amount of a composition comprising a polynucleotide operatively coding for dystrophin in a pharmaceutically acceptable injectable carrier in vivo into muscle tissue of an animal suffering from muscular dystrophy, whereby the polynucleotide is taken up into the cells and dystrophin is produced in vivo. Preferably, the polynucleotide is a naked polynucleotide and the composition is introduced interstitially into the muscle tissue.

The present invention also includes pharmaceutical products for all of the uses contemplated in the methods described herein. For example, there is a pharmaceutical product, comprising naked polynucleotide, operatively coding for a biologically active polypeptide, in physiologically acceptable administrable form, in a container, and a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert.

In another embodiment, the invention provides a pharmaceutical product, comprising naked polynucleotide, operatively coding for a biologically active peptide, in solution in a physiologically acceptable injectable carrier and suitable for introduction interstitially into a tissue to cause cells of the tissue to express the polypeptide, a container enclosing the solution, and a notice associated with the container in form prescribed by a governmental agency regulating the manufacture, use, or sale of pharmaceuticals, which notice is reflective of approval by the agency of manufacture, use, or sale of the solution of polynucleotide for human or veterinary administration. The peptide may be immunogenic and administration of the solution to a human may serve to vaccinate the human, or an animal. Similarly, the peptide may be therapeutic and administration of the solution to a vertebrate in need of therapy relating to the polypeptide will have a therapeutic effect.

Also provided by the present invention is a pharmaceutical product, comprising naked antisense polynucleotide, in solution in a physiologically acceptable injectable carrier and suitable for introduction interstitially into a tissue to cause cells of the tissue to take up the polynucleotide and provide a therapeutic effect, a container enclosing the solution, and a notice associated with the container in form prescribed by a governmental agency regulating the manufacture, use, or sale of pharmaceuticals, which notice is reflective of approval by the agency of manufacture, use, or sale of the solution of polynucleotide for human or veterinary administration.

One particularly important aspect of the invention relates to a pharmaceutical product for treatment of muscular dystrophy, comprising a sterile, pharmaceutically acceptable carrier, a pharmaceutically effective amount of a naked polynucleotide operatively coding for dystrophin in the carrier, and a container enclosing the carrier and the polynucleotide in sterile fashion. Preferably, the polynucleotide is DNA.

From yet another perspective, the invention includes pharmaceutical product for use in supplying a biologically active polypeptide to a vertebrate, comprising a pharmaceutically effective amount of a naked polynucleotide operatively coding for the polypeptide, a container enclosing the carrier and the polynucleotide in a sterile fashion, and means associated with the container for permitting transfer of the polynucleotide from the container to the interstitial space of a tissue, whereby cells of the tissue can take up and express the polynucleotide. The means for permitting such transfer can include a conventional septum that can be penetrated, e.g., by a needle. Alternatively, when the container is a syringe, the means may be considered to comprise the plunger of the syringe or a needle attached to the syringe. Containers used in the present invention will usually have at least 1, preferably at least 5 or 10, and more preferably at least 50 or 100 micrograms of polynucleotide, to provide one or more unit dosages. For many applications, the container will have at least 500 micrograms or 1 milligram, and often will contain at least 50 or 100 milligrams of polynucleotide.

Another aspect of the invention provides a pharmaceutical product for use in immunizing a vertebrate, comprising a pharmaceutically effective amount of a naked polynucleotide operatively coding for an immunogenic polypeptide, a sealed container enclosing the polynucleotide in a sterile fashion, and means associated with the container for permitting transfer of the polynucleotide from the container to the interstitial space of a tissue, whereby cells of the tissue can take up and express the polynucleotide.

Still another aspect of the present invention is the use of naked polynucleotide operatively coding for a physiologically active polypeptide in the preparation of a pharmaceutical for introduction interstitially into tissue to cause cells comprising the tissue to produce the polypeptide. The pharmaceutical, for example, may be for introduction into muscle tissue whereby muscle cells produce the polypeptide. Also contemplated is such use, wherein the peptide is dystrophin and the pharmaceutical is for treatment of muscular dystrophy.

Another use according to the invention is use of naked antisense polynucleotide in the preparation of a pharmaceutical for introduction interstitially into tissue of a vertebrate to inhibit translation of polynucleotide in cells of the vertebrate.

The tissue into which the polynucleotide is introduced can be a persistent, non-dividing cell. The polynucleotide may be either a DNA or RNA sequence. When the polynucleotide is DNA, it can also be a DNA sequence which is itself non-replicating, but is inserted into a plasmid, and the plasmid further comprises a replicator. The DNA may be a sequence engineered so as not to integrate into the host cell genome. The polynucleotide sequences may code for a polypeptide which is either contained within the cells or secreted therefrom, or may comprise a sequence which directs the secretion of the peptide.

The DNA sequence may also include a promoter sequence. In one preferred embodiment, the DNA sequence includes a cell-specific promoter that permits substantial transcription of the DNA only in predetermined cells. The DNA may also code for a polymerase for transcribing the DNA, and may comprise recognition sites for the polymerase and the injectable preparation may include an initial quantity of the polymerase.

In many instances, it is preferred that the polynucleotide is translated for a limited period of time so that the polypeptide delivery is transitory. The polypeptide may advantageously be a therapeutic polypeptide, and may comprise an enzyme, a hormone, a lymphokine, a receptor, particularly a cell surface receptor, a regulatory protein, such as a growth factor or other regulatory agent, or any other protein or peptide that one desires to deliver to a cell in a living vertebrate and for which corresponding DNA or mRNA can be obtained.

In preferred embodiments, the polynucleotide is introduced into muscle tissue; in other embodiments the polynucleotide is incorporated into tissuess of skin, brain, lung, liver, spleen or blood. The preparation is injected into the vertebrate by a variety of routes, which may be intradermally, subdermally, intrathecally, or intravenously, or it may be placed within cavities of the body. In a preferred embodiment, the polynucleotide is injected intramuscularly. In still other embodiments, the preparation comprising the polynucleotide is impressed into the skin. Transdermal administration is also contemplated, as is inhalation.

In one preferred embodiment, the polynucleotide is DNA coding for both a polypeptide and a polymerase for transcribing the DNA, and the DNA includes recognition sites for the polymerase and the injectable preparation further includes a means for providing an initial quantity of the polymerase in the cell. The initial quantity of polymerase may be physically present together with the DNA. Alternatively, it may be provided by including mRNA coding therefor, which mRNA is translated by the cell. In this embodiment of the invention, the DNA is preferably a plasmid. Preferably, the polymerase is phage T7 polymerase and the recognition site is a T7 origin of replication sequence.

In accordance with another aspect of the invention, there is provided a method for treating a disease associated with the deficiency or absence of a specific polypeptide in a vertebrate, comprising the steps of obtaining, an injectable preparation comprising a pharmaceutically acceptable injectable carrier containing a naked polynucleotide coding for the specific polypeptide; introducing the injectable preparation into a vertebrate and permitting the polynucleotide to be incorporated into a cell, wherein the polypeptide is formed as the translation product of the polynucleotide, and whereby the deficiency or absence of the polypeptide is compensated for. In preferred embodiments, the preparation is introduced into muscle tissue and the method is applied repetitively. The method is advantageously applied where the deficiency or absence is due to a genetic defect. The polynucleotide is preferably a non-replicating DNA sequence; the DNA sequence may also be incorporated into a plasmid vector which comprises an origin of replication.

In one of the preferred embodiments, the polynucleotide codes for a non-secreted polypeptide, and the polypeptide remains in situ. According to this embodiment, when the polynucleotide codes for the polypeptide dystrophin, the method provides a therapy for Duchenne's syndrome; alternatively, when the polynucleotide codes for the polypeptide phenylalanine hydroxylase, the method comprises a therapy for phenylketonuria. In another preferred embodiment of the method, the polynucleotide codes for a polypeptide which is secreted by the cell and released into the circulation of the vertebrate; in a particularly preferred embodiment the polynucleotide codes for human growth hormone.

In yet another embodiment of the method, there is provided a therapy for hypercholesterolemia wherein a polynucleotide coding for a receptor associated with cholesterol homeostasis is introduced into a liver cell, and the receptor is expressed by the cell.

In accordance with another aspect of the present invention, there is provided a method for immunizing a vertebrate, comprising the steps of obtaining a preparation comprising an expressible polynucleotide coding for an immunogenic translation product, and introducing the preparation into a vertebrate wherein the translation product of the polynucleotide is formed by a cell of the vertebrate, which elicits an immune response against the immunogen. In one embodiment of the method, the injectable preparation comprises a pharmaceutically acceptable carrier containing an expressible polynucleotide coding for an immunogenic peptide, and on the introduction of the preparation into the vertebrate, the polynucleotide is incorporated into a cell of the vertebrate wherein an immunogenic translation product of the polynucleotide is formed, which elicits an immune response against the immunogen.

In an alternative embodiment, the preparation comprises one or more cells obtained from the vertebrate and transfected in vitro with the polynucleotide, whereby the polynucleotide is incorporated into said cells, where an immunogenic translation product of the polynucleotide is formed, and whereby on the introduction of the preparation into the vertebrate, an immune response against the immunogen is elicited. In any of the embodiments of the invention, the immunogenic product may be secreted by the cells, or it may be presented by a cell of the vertebrate in the context of the major histocompatibility antigens, thereby eliciting an immune response against the immunogen. The method may be practiced using non-dividing, differentiated cells from the vertebrates, which cells may be lymphocytes, obtained from a blood sample; alternatively, it may be practiced using partially differentiated skin fibroblasts which are capable of dividing. In a preferred embodiment, the method is practiced by incorporating the polynucleotide coding for an immunogenic translation product into muscle tissue.

The polynucleotide used for immunization is preferably an mRNA sequence, although a non-replicating DNA sequence may be used. The polynucleotide may be introduced into tissues of the body using the injectable carrier alone; liposomal preparations are preferred for methods in which in vitro transfections of cells obtained from the vertebrate are carried out.

The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide.

The method may be used to selectively elicit a humoral immune response, a cellular immune response, or a mixture of these. In embodiments wherein the cell expresses major histocompatibility complex of Class I, and the immunogenic peptide is presented in the context of the Class I complex, the immune response is cellular and comprises the production of cytotoxic T-cells.

In one such embodiment, the immunogenic peptide is associated with a virus, is presented in the context of Class I antigens, and stimulates cytotoxic T-cells which are capable of destroying cells infected with the virus. A cytotoxic T-cell response may also be produced according the method where the polynucleotide codes for a truncated viral antigen lacking humoral epitopes.

In another of these embodiments, the immunogenic peptide is associated with a tumor, is presented in the context of Class I antigens, and stimulates cytotoxic T cells which are capable of destroying tumor cells. In yet another embodiment wherein the injectable preparation comprises cells taken from the animal and transfected In vitro, the cells expressing major histocompatibility antigen of class I and class II, and the immune response is both humoral and cellular and comprises the production of both antibody and cytotoxic T-cells.

In another embodiment, there is provided a method of immunizing a vertebrate, comprising the steps of obtaining a positively charged liposome containing an expressible polynucleotide coding for an immunogenic peptide, and introducing the liposome into a vertebrate, whereby the liposome is incorporated into a monocyte, a macrophage, or another cell, where an immunogenic translation product of the polynucleotide is formed, and the product is processed and presented by the cell in the context of the major histocompatibility complex, thereby eliciting an immune response against the immunogen. Again, the polynucleotide is preferably mRNA, although DNA may also be used. And as before, the method may be practiced without the liposome, utilizing just the polynucleotide in an injectable carrier.

The present invention also encompasses the use of DNA coding for a polypeptide and for a polymerase for transcribing the DNA, and wherein the DNA includes recognition sites for the polymerase. The initial quantity of polymerase is provided by including mRNA coding therefor in the preparation, which mRNA is translated by the cell. The mRNA preferably is provided with means for retarding its degradation in the cell. This can include capping the mRNA, circularizing the mRNA, or chemically blocking the 5' end of the mRNA. The DNA used in the invention may be in the form of linear DNA or may be a plasmid. Episomal DNA is also contemplated. One preferred polymerase is phage T7 RNA polymerase and a preferred recognition site is a T7 RNA polymerase promoter.

DETAILED DESCRIPTION OF THE INVENTION

The practice of the present invention requires obtaining naked polynucleotide operatively coding for a polypeptide for incorporation into vertebrate cells. A polynucleotide operatively codes for a polypeptide when it has all the genetic information necessary for expression by a target cell, such as promoters and the like. These polynucleotides can be administered to the vertebrate by any method that delivers injectable materials to cells of the vertebrate, such as by injection into the interstitial space of tissues such as muscles or skin, introduction into the circulation or into body cavities or by inhalation or insufflation. A naked polynucleotide is injected or otherwise delivered to the animal with a pharmaceutically acceptable liquid carrier. In preferred applications, the liquid carrier is aqueous or partly aqueous, comprising sterile, pyrogen-free water. The pH of the preparation is suitably adjusted and buffered. The polynucleotide can comprise a complete gene, a fragment of a gene, or several genes, together with recognition and other sequences necessary for expression.

In the embodiments of the invention that require use of liposomes, for example, when the polynucleotide is to be associated with a liposome, it requires a material for A forming liposomes, preferably cationic or positively charged liposomes, and requires that liposomal preparations be made from these materials. With the liposomal material in hand, the polynucleotide may advantageously be used to transfect cells in vitro for use as immunizing agents, or to administer polynucleotides into bodily sites where liposomes may be taken up by phagocytic cells.

Polynucleotide Materials

The naked polynucleotide materials used according to the methods of the invention comprise DNA and RNA sequences or DNA and RNA sequences coding for polypeptides that have useful therapeutic applications. These polynucleotide sequences are naked in the sense that they are free from any delivery vehicle that can act to facilitate entry into the cell, for example, the polynucleotide sequences are free of viral sequences, particularly any viral particles which may carry genetic information. They are similarly free from, or naked with respect to, any material which promotes transfection, such as liposomal formulations, charged lipids such as Lipofectin™ or precipitating agents such as $CaPO_4$.

The DNA sequences used in these methods can be those sequences which do not integrate into the genome of the host cell. These may be non-replicating DNA sequences, or specific replicating sequences genetically engineered to lack the genome-integration ability.

The polynucleotide sequences of the invention are DNA or RNA sequences having a therapeutic effect after being taken up by a cell. Examples of polynucleotides that are themselves therapeutic are anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body.

Therapeutic polynucleotides provided by the invention can also code for immunity-conferring polypeptides, which can act as endogenous immunogens to provoke a humoral or cellular response, or both. The polynucleotides employed according to the present invention can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, Fab', Fab and the like, including hybrid fragments. Also included within the meaning of "antibody" are conjugates of such fragments, and so-called antigen binding proteins (single chain antibodies) as described, for example, in U.S. Pat. No. 4,704,692, the contents of which are hereby incorporated by reference.

Thus, an isolated polynucleotide coding for variable regions of an antibody can be introduced, in accordance with the present invention, to enable the treated subject to produce antibody in situ. For illustrative methodology relating to obtaining antibody-encoding polynucleotides, see Ward et al. *Nature*, 341:544–546 (1989); Gillies et al., *Biotechnol.* 7:799–804 (1989); and Nakatani et al., loc. cit., 805–810 (1989). The antibody in turn would exert a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

Polynucleotide sequences of the invention preferably code for therapeutic or immunogenic polypeptides, and these sequences may be used in association with other polynucleotide sequences coding for regulatory proteins that control the expression of these polypeptides. The regulatory protein can act by binding to genomic DNA so as to regulate its transcription; alternatively, it can act by binding to messenger RNA to increase or decrease its stability or translation efficiency.

The polynucleotide material delivered to the cells In vivo can take any number of forms, and the present invention is not limited to any particular polynucleotide coding for any particular polypeptide. Plasmids containing genes coding for a large number of physiologically active peptides and antigens or immunogens have been reported in the literature and can be readily obtained by those of skill in the art.

Where the polynucleotide is to be DNA, promoters suitable for use in various vertebrate systems are well known. For example, for use in murine systems, suitable strong promoters include RSV LTR, MPSV LTR, SV40 IEP, and metallothionein promoter. In humans, on the other hand, promoters such as CMV IEP may advantageously be used. All forms of DNA, whether replicating or non-replicating, which do not become integrated into the genome, and which are expressible, are within the methods contemplated by the invention.

With the availability of automated nucleic acid synthesis equipment, both DNA and RNA can be synthesized directly when the nucleotide sequence is known or by a combination of PCR cloning and fermentation. Moreover, when the sequence of the desired polypeptide is known, a suitable coding sequence for the polynucleotide can be inferred.

When the polynucleotide is mRNA, it can be readily prepared from the corresponding DNA in vitro. For example, conventional techniques utilize phage RNA polymerases SP6, T3, or T7 to prepare mRNA from DNA templates in the presence of the individual ribonucleoside triphosphates. An appropriate phage promoter, such as a T7 origin of replication site is placed in the template DNA immediately upstream of the gene to be transcribed. Systems utilizing T7 in this manner are well known, and are described in the literature, e.g., in Current Protocols in Molecular Biology, §3.8 (Vol.1 1988).

One particularly-preferred method for obtaining the mRNA used in the present invention is set forth in Examples 2–5. In general, however, it should be apparent that the pXGB plasmid or any similar plasmid that can be readily constructed by those of ordinary skill in the art can be used with a virtually unlimited number of cDNAs in practicing the present invention. Such plasmids may advantageously comprise a promoter for a desired RNA polymerase, followed by a 5' untranslated region, a 3' untranslated region, and a template for a poly A tract. There should be a unique restriction site between these 5' and 3' regions to facilitate the insertion of any desired cDNA into the plasmid. Then, after cloning the plasmid containing the desired gene, the plasmid is linearized by cutting in the polyadenylation region and is transcribed in vitro to form mRNA transcripts. These transcripts are preferably provided with a 5' cap, as demonstrated in Example 5. Alternatively, a 5' untranslated sequence such as EMC can be used which does not require a 5' cap.

While the foregoing represents a preferred method for preparing the mRNA, it will be apparent to those of skill 1' in the art that many alternative methods also exist. For example, the mRNA can be prepared in commercially-available nucleotide synthesis apparatus. Alternatively, mRNA in circular form can be prepared. Exonuclease-resistant RNAs such as circular mRNA, chemically blocked mRNA, and mRNA with a 5' cap are preferred, because of their greater half-life in vivo.

In particular, one preferred mRNA is a self-circularizing mRNA having the gene of interest preceded by the 5' untranslated region of polio virus. It has been demonstrated that circular mRNA has an extremely long half-life (Harland & Misher, Development 102: 837–852 (1988)) and that the polio virus 5' untranslated region can promote translation of mRNA without the usual 5' cap (Pelletier & Sonnenberg, Nature 334:320–325 (1988), hereby incorporated by reference).

This material may be prepared from a DNA template that is self-splicing and generates circular "lariat" mRNAs, using the method of Been & Cech, Cell 47:206–216 (1986) (hereby incorporated by reference). We modify that template by including the 5' untranslated region of the polio virus immediately upstream of the gene of interest, following the procedure of Maniatis, T. et al. MOLECULAR CLONING: A LABORATORY MANUAL, Cold Spring Harbor, N.Y. (1982).

In addition, the present invention includes the use of mRNA that is chemically blocked at the 5' and/or 3' end to prevent access by RNAse. (This enzyme is an exonuclease and therefore does not cleave RNA in the middle of the chain.) Such chemical blockage can substantially lengthen the half life of the RNA in vivo. Two agents which may be used to modify RNA are available from Clonetech Laboratories, Inc., Palo. Alto, Calif. C2 AminoModifier (Catalog # 5204-1) and Amino-7-dUTP (Catalog # K1022-1). These materials add reactive groups to the RNA. After introduction of either of these agents onto an RNA molecule of interest, an appropriate reactive substituent can be linked to the RNA according to the manufacturer's instructions. By adding a group with sufficient bulk, access to the chemically modified RNA by RNAse can be prevented.

Transient Gene Therapy

Unlike gene therapies proposed in the past, one major advantage of the present invention is the transitory nature of the polynucleotide synthesis in the cells. (We refer to this as reversible gene therapy, or TGT.) With mRNA introduced according to the present invention, the effect will generally last about one day. Also, in marked contrast to gene therapies proposed in the past, mRNA does not have to penetrate the nucleus to direct protein synthesis; therefore, it should have no genetic liability.

In some situations, however, a more prolonged effect may be desired without incorporation of the exogenous polynucleic acid into the genome of the host organism. In order to provide such an effect, a preferred embodiment of the invention provides introducing a DNA sequence coding for a specific polypeptide into the cell. We have found, according to the methods of the invention, that non-replicating DNA sequences can be introduced into cells to provide production of the desired polypeptide for periods of about up to six months, and we have observed no evidence of integration of the DNA sequences into the genome of the cells. Alternatively, an even more prolonged effect can be achieved by introducing the DNA sequence into the cell by means of a vector plasmid having the DNA sequence inserted therein. Preferably, the plasmid further comprises a replicator. Such plasmids are well known to those skilled in the art, for example, plasmid pBR322, with replicator pMB1, or plasmid pMK16, with replicator ColE1 (Ausubel, Current Protocols in Molecular Biology, John Wiley and Sons, New York (1988) §II:1.5.2.

Results of studies of the time course of expression of DNA and mRNA introduced into muscle cells as described in Examples 1 and 13 indicate that mRNA expression is more rapid, although shorter in duration than DNA expression. An immediate and long lived gene expression can be achieved by administering to the cell a liposomal preparation. comprising both DNA and an RNA polymerase, such as the phage polymerases T7, T3, and SP6. The liposome also includes an initial source of the appropriate RNA polymerase, by either including the actual enzyme itself, or alternatively, an mRNA coding for that enzyme. When the liposome is introduced into the organism, it delivers the DNA and the initial source of RNA polymerase to the cell.

The RNA polymerase, recognizing the promoters on the introduced DNA, transcribes both genes, resulting in translation products comprising more RNA polymerase and the desired polypeptide. Production of these materials continues until the introduced DNA (which is usually in the form of a plasmid) is degraded. In this manner, production of the desired polypeptide in vivo can be achieved in a few hours and be extended for one month or more.

Although not limited to the treatment of genetic disease, the methods of the invention can accordingly be appropriately applied to treatment strategies requiring delivery and functional expression of missing or defective genes.

The polynucleotides may be delivered to the interstitial space of tissues of the animal body, including those of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. We have discovered that in vivo muscle cells are particularly competent in their ability to take up and express polynucleotides. This ability may be due to the singular tissue architecture of muscle, comprising multinucleated cells, sarcoplasmic reticulum, and transverse tubular system. Polynucleotides may enter the muscle through the transverse tubular system, which contains extra cellular fluid and extends deep into the muscle cell. It is also possible that the polynucleotides enter damaged muscle cells which then recover.

Muscle is also advantageously used as a site for the delivery and expression of polynucleotides in a number of therapeutic applications because animals have a proportionately large muscle mass which is conveniently accessed by direct injection through the skin; for this reason, a comparatively large dose of polynucleotides can be deposited in muscle by multiple injections, and repetitive injections, to extend therapy over long periods of time, are easily performed and can be carried out safely and without special skill or devices.

Muscle tissue can be used as a site for injection and expression of polynucleotides in a set of general strategies, which are exemplary and not exhaustive. First, muscle disorders related to defective or absent gene products can be treated by introducing polynucleotides coding for a non-secreted gene product into the diseased muscle tissue. In a second strategy, disorders of other organs or tissues due to the absence of a gene product, and which results in the build-up of a circulating toxic metabolite can be treated by introducing the specific therapeutic polypeptide into muscle tissue where the non-secreted gene product is expressed and clears the circulating metabolite. In a third strategy, a polynucleotide coding for an secretable therapeutic polypeptide can be injected into muscle tissue from where the polypeptide is released into the circulation to seek a metabolic target. This use is demonstrated in the expression of growth hormone gene injected into muscle, Example 18. Certain DNA segments, are known to serve as "signals" to direct secretion (Wickner, W. T. and H. F. Lodish, Science 230:400–407 (1985), and these may be advantageously employed. Finally, in immunization strategies, muscle cells may be injected with polynucleotides coding for immunogenic peptides, and these peptides will be presented by muscle cells in the context of antigens of the major histocompatibility complex to provoke a selected immune response against the immunogen.

Tissues other than those of muscle, and having a less efficient uptake and expression of injected polynucleotides, may nonetheless be advantageously used as injection sites to produce therapeutic polypeptides or polynucleotides under certain conditions. One such condition is the use of a polynucleotide to provide a polypeptide which to be effective must be present in association with cells of a specific type; for example, the cell surface receptors of liver cells associated with cholesterol homeostasis. (Brown and Goldstein, Science 232:34–47 (1986)). In this application, and in many others, such as those in which an enzyme or hormone is the gene product, it is not necessary to achieve high levels of expression in order to effect a valuable therapeutic result.

One application of TGT is in the treatment of muscular dystrophy. The genetic basis of the muscular dystrophies is just beginning to be unraveled. The gene related to Duchenne/Becker muscular dystrophy has recently been cloned and encodes a rather large protein, termed dystrophin. Retroviral vectors are unlikely to be useful, because they could not accommodate the rather large size of the cDNA (about 13 kb) for dystrophin. Very recently reported work is centered on transplanting myoblasts, but the utility of this approach remains to be determined. Clearly, an attractive approach would be to directly express the dystrophin gene within the muscle of patients with Duchennes. Since most patients die from respiratory failure, the muscles involved with respiration would be a primary target.

Another application is in the treatment of cystic fibrosis. The gene for cystic fibrosis was recently identified (Goodfellow, P. Nature, 341(6238):102–3 (Sept. 14, 1989); Rommens, J. et al. Science, 245(4922):1059–1065 (Sep. 8, 1989); Beardsley, T. et al., Scientific American, 261(5):28–30 (1989). Significant amelioration of the symptoms should be attainable by the expression of the dysfunctional protein within the appropriate lung cells. The bronchial epithelial cells are postulated to be appropriate target lung cells and they could be accessible to gene transfer following instillation of genes into the lung. Since cystic fibrosis is an autosomal recessive disorder one would need to achieve only about 5% of normal levels of the cystic fibrosis gene product in order to significantly ameliorate the pulmonary symptoms.

Biochemical genetic defects of intermediary metabolism can also be treated by TGT. These diseases include phenylketonuria, galactosemia, maple-syrup urine disease, homocystinuria, propionic acidemia, methylmalonic acidemia, and adenosine deaminase deficiency. The pathogenesis of disease in most of these disorders fits the phenylketonuria (PKU) model of a circulating toxic metabolite. That is, because of an enzyme block, a biochemical, toxic to the body, accumulates in body fluids. These disorders are ideal for gene therapy for a number of reasons. First, only 5% of normal levels of enzyme activity would have to be attained in order to significantly clear enough of the circulating toxic metabolite so that the patient is significantly improved. Second, the transferred gene could most often be expressed in a variety of tissues and still be able to clear the toxic biochemical.

Reversible gene therapy can also be used in treatment strategies requiring intracytoplasmic or intranuclear protein expression. Some proteins are known that are capable of regulating transcription by binding to specific promoter regions on nuclear DNA. Other proteins bind to RNA, regulating its degradation, transport from the nucleus, or translation efficiency. Proteins of this class must be delivered intracellularly for activity. Extracellular delivery of recombinant transcriptional or translational regulatory proteins would not be expected to have biological activity, but functional delivery of the DNA or RNA by TGT would be active. Representative proteins of this type that would benefit from TGT would include NEF, TAT, steroid receptor and the retinoid receptor.

Gene therapy can be used in a strategy to increase the resistance of an AIDS patient to HIV infection. Introducing an AIDS resistance gene, such as, for example, the NEF gene or the soluble CD4 gene to prevent budding, into an AIDS patient's T cells will render his T cells less capable of producing active AIDS virus, thus sparing the cells of the immune system and improving his ability to mount a T cell dependent immune response. Thus, in accordance with the invention, a population of the AIDS patient's own T cells is isolated from the patient's blood. These cells are then transfected in vitro and then reintroduced back into the patient's blood. The virus-resistant cells will have a selective advantage over the normal cells, and eventually repopulate the patient's lymphatic system. DNA systemic delivery to macrophages or other target cells can be used in addition to the extracorporeal treatment strategy. Although this strategy would not be expected to eradicate virus in the macrophage reservoir, it will increase the level of T cells and improve the patient's immune response.

In all of the systemic strategies presented herein, an effective DNA or mRNA dosage will generally be in the range of from about 0.05 $\mu$g/kg to about 50 mg/kg, usually about 0.005–5 mg/kg. However, as will be appreciated, this dosage will vary in a manner apparent to those of skill in the art according to the activity of the peptide coded for by the DNA or mRNA and the particular peptide used. For delivery of adenosine deaminase to mice or humans, for example, adequate levels of translation are achieved with a DNA or mRNA dosage of about 0.5 to 5 mg/kg. See Example 10. From this information, dosages for other peptides of known activity can be readily determined.

Diseases which result from deficiencies of critical proteins may be appropriately treated by introducing into specialized cells, DNA or mRNA coding for these proteins. A variety of growth factors such as nerve growth factor and fibroblast growth factor have been shown to affect neuronal cell survival in animal models of Alzheimer's disease. In the aged rat model, NGF infusions have reversed the loss of cholinergic neurons. In the fimbria-fornix lesion rat, NGF infusions or secretion from genetically-modified fibroblasts have also avoided the loss of cholinergic function. Cholinergic activity is diminished in patients with Alzheimer's. The expression within the brain of transduced genes expressing growth factors could reverse the lost of function of specific neuronal groups.

Introduction of DNA or mRNA by transfection of the gene for neuronal growth factor into cells lining the cranial cavity can be used in accordance with the present invention in the treatment of Alzheimer's disease. In particular, the present invention treats this. disease by intracranial injection of from about 10 $\mu$g to about 100 $\mu$g of DNA or mRNA into the parenchyma through use of a stereotaxic apparatus. Specifically, the injection is targeted to the cholinergic neurons in the medial septum. The DNA or mRNA injection is repeated every 1–3 days for 5' capped, 3' polyadenylated mRNA, and every week to 21 days for circular mRNA, and every 30 to 60 days for DNA. Injection of DNA in accordance with the present invention is also contemplated. DNA would be injected in corresponding amounts; however, frequency of injection would be greatly reduced. Episomal DNA, for example, could be active for a number of months, and reinjection would only be necessary upon notable regression by the patient.

In addition, the enzymes responsible for neurotransmitter synthesis could be expressed from transduced genes. For example, the gene for choline acetyl transferase could be expressed within the brain cells (neurons or glial) of specific areas to increase acetylcholine levels and improve brain function.

The critical enzymes involved in the synthesis of other neurotransmitters such as dopamine, norepinephrine, and GABA have been cloned and available. The critical enzymes could be locally increased by gene transfer into a localized area of the brain. The increased productions of these and other neurotransmitters would have broad relevance to manipulation of localized neurotransmitter function and thus to a broad range of brain disease in which disturbed neurotransmitter function plays a crucial role. Specifically, these diseases could include schizophrenia and manic-depressive illnesses and Parkinson's Disease. It is well established that patients with Parkinson's suffer from progressively disabled motor control due to the lack of dopamine synthesis within the basal ganglia. The rate limiting step for dopamine synthesis is the conversion of tyrosine to L-DOPA by the enzyme, tyrosine hydroxylase. L-DOPA is then converted to dopamine by the ubiquitous enzyme, DOPA decarboxylase. That is why the well-established therapy with L-DOPA is effective (at least for the first few years of treatment). Gene therapy could accomplish the similar pharmacologic objective by expressing the genes for tyrosine hydroxylase and possible DOPA decarboxylase as well. Tyrosine is readily available within the CNS.

The genetic form of alpha-1-antitrypsin deficiency can result in both liver and lung disease. The liver disease, which is less common, is caused by the accumulation of an abnormal protein and would be less amenable to gene therapy. The pulmonary complications, however, would be amenable to the increased expression of alpha-1-antitrypsin within the lung. This should prevent the disabling and eventually lethal emphysema from developing.

Alpha-1-antitrypsin deficiency also occurs in tobacco smokers since tobacco smoke decreases alpha-1-antitrypsin activity and thus serine protease activity that leads to emphysema. In addition, some recent data links tobacco smoke's anti-trypsin effect to aneurysms of the aorta. Aneurysms would also be preventable by raising blood levels of anti-1-antitrypsin since this would, decrease protease activity that leads to aneurysms.

Patients with degenerative disease of the lung could also benefit from the expression of enzymes capable of removing other toxic metabolites which tend to accumulate in diseased lung tissue. Superoxide dismutase and catalase could be delivered by TGT to ameliorate these problems.

TGT can be used in treatment strategies requiring the delivery of cell surface receptors. It could be argued that there is no need to decipher methodology for functional in vivo delivery of genes. There is, after all, an established technology for the synthesis and large scale production of proteins, and proteins are the end product of gene expression. This logic applies for many protein molecules which act extracellularly or interact with cell surface receptors, such as tissue plasminogen activator (TPA), growth hormone, insulin, interferon, granulocyte-macrophage colony stimulating factor (GMCSF), erythropoietin (EPO), etc. However, the drug delivery. problems associated with properly delivering a recombinant cell surface receptor to be inserted in the plasma membrane of its target cell in the proper orientation for a functional receptor have hithertofore appeared intractable.

When DNA or RNA coding for a cell surface receptor is delivered intracellularly in accordance with the present invention, the resulting protein can be efficiently and functionally expressed on the target cell surface. If the problem of functional delivery of recombinant cell surface receptors remains intractable, then the only way of approaching this therapeutic modality will be through gene delivery. Similar logic for nuclear or cytoplasmic regulation of gene expression applies to nuclear regulatory factor bound to DNA to regulate (up or down) RNA transcription and to cytoplasmic regulatory factors which bind to RNA to increase or decrease translational efficiency and degradation. TGT could in this way provide therapeutic strategies for the treatment of cystic fibrosis, muscular dystrophy and hypercholesterolemia.

Elevated levels of cholesterol in the blood may be reduced in accordance with the present invention by supplying mRNA coding for the LDL surface receptor to hepatocytes. A slight elevation in the production of this receptor in the liver of patients with elevated LDL will have significant therapeutic benefits. Therapies based on systemic administration of recombinant proteins are not able to compete with the present invention, because simply administering the recombinant protein, could not get the receptor into the plasma membrane of the target cells. The receptor must be properly inserted into the membrane in order to exert its biological effect. It is not usually necessary to regulate the level of receptor expression; the more expression the better. This simplifies the molecular biology involved in preparation of the mRNA for use in the present invention. For example, lipid/DNA or RNA complexes containing the LDL receptor gene may be prepared and supplied to the patient by repetitive I.V. injections. The lipid complexes will be taken up largely by the liver. Some of the complexes will be taken up by hepatocytes. The level of LDL receptor in the liver will increase gradually as the. number of injections increases. Higher liver LDL receptor levels will lead to therapeutic lowering of LDL and cholesterol. An effective mRNA dose will generally be from about 0.1 to about 5 mg/kg.

Other examples of beneficial applications of TGT include the introduction of the thymidine kinase gene into macrophages of patients infected with the HIV virus. Introduction of the thymidine kinase gene into the macrophage reservoir will render those cells more capable of phosphorylating AZT. This tends to overcome their resistance to AZT therapy, making AZT capable of eradicating the HIV reservoir in macrophages. Lipid/DNA complexes containing the thymidine kinase gene can be prepared and administered to the patient through repetitive intravenous injections. The lipid complexes will be taken up largely by the macrophage reservoir leading to elevated levels of thymidine kinase in the macrophages. This will render the AZT resistant cells subject to treatment with AZT. The thymidine kinase therapy can also be focused by putting the thymidine kinase gene under the control of the HTLV III promoter. According to this strategy, the thymidine kinase would only be synthesized on infection of the cell by HIV virus, and the production of the tat protein which activates the promoter. An analogous therapy would supply cells with the gene for diphtheria toxin under the control of the same HTLV III promoter, with the lethal result occurring in cells only after HIV infection.

These AIDS patients could also be treated by supplying the interferon gene to the macrophages according to the TGT method. Increased levels of localized interferon production in macrophages could render them more resistant to the consequences of HIV infection. While local levels of interferon would be high, the overall systemic levels would remain low, thereby avoiding the systemic toxic effects like those observed after recombinant interferon administration. Lipid/DNA or RNA complexes containing the interferon gene can be prepared and administered to the patient by repetitive intravenous injections. The lipid complexes will be taken up largely by the macrophage reservoir leading to elevated localized levels of interferon in the macrophages. This will render them less susceptible to HIV infection.

Various cancers may be treated using TGT by supplying a diphtheria toxin gene on a DNA template with a tissue specific enhancer to focus expression of the gene in the cancer cells. Intracellular expression of diphtheria toxin kills cells. These promoters could be tissue-specific such as using a pancreas-specific promoter for the pancreatic cancer. A functional diphtheria toxin gene delivered to pancreatic cells could eradicate the entire pancreas. This strategy could be used as a treatment for pancreatic cancer. The patients would have no insurmountable difficulty surviving without a pancreas. The tissue specific enhancer would ensure that expression of diphtheria toxin would only occur in pancreatic cells. DNA/lipid complexes containing the diphtheria toxin gene under the control of a tissue specific enhancer would be introduced directly into a cannulated artery feeding the pancreas. The infusion would occur on some dosing schedule for as long as necessary to eradicate the pancreatic tissue. Other lethal genes besides diphtheria toxin could be used with similar effect, such as genes for ricin or cobra venom factor or enterotoxin.

Also, one could treat cancer by using a cell-cycle specific promoter that would only kill cells that are rapidly cycling (dividing) such as cancer cells. Cell-cycle specific killing could also be accomplished by designing mRNA encoding killer proteins that are stable only in cycling cells (i.e. histone mRNA that is only stable during S phase). Also, one could use developmental-specific promoters such as the use of alpha-fetoprotein that is only expressed in fetal liver cells and in hepatoblastoma cells that have dedifferentiated into a more fetal state.

One could also treat specialized cancers by the transfer of genes such as the retinoblastoma gene (and others of that family) that suppress the cancer properties of certain cancers.

The TGT strategy can be used to provide a controlled, sustained delivery of peptides. Conventional drugs, as well as recombinant protein drugs, can benefit from controlled release devices. The purpose of the controlled release device is to deliver drugs over a longer time period, so that the number of doses required is reduced. This results in improvements in patient convenience and compliance. There are a wide variety of emerging technologies that are intended to achieve controlled release.

TGT can be used to obtain controlled delivery of therapeutic peptides. Regulated expression can be obtained by using suitable promoters, including cell-specific promoters. Suitable peptides delivered by the present invention include, for example, growth hormone, insulin, interleukins, interferons, GMCSF, EPO, and the like. Depending on the specific application, the DNA or an RNA construct selected can be designed to result in a gene product that is secreted from the injected cells and into the systemic circulation.

TGT can also comprise the controlled delivery of therapeutic polypeptides or peptides which is achieved by including with the polynucleotide to be expressed in the cell, an additional polynucleotide which codes for a regulatory protein which controls processes of transcription and translation. These polynucleotides comprise those which operate either to up regulate or down regulate polypeptide expression, and exert their effects either within the nucleus or by controlling protein translation events in the cytoplasm.

The T7 polymerase gene can be used in conjunction with a gene of interest to obtain longer duration of effect of TGT. Episomal DNA such as that obtained from the origin of replication region for the Epstein Barr virus can be used, as well as that from other origins of replication which are functionally active in mammalian cells, and preferably those that are active in human cells. This is a way to obtain expression from cells after many cell divisions, without risking unfavorable integration events that are common to retrovirus vectors. Controlled release of calcitonin could be obtained if a calcitonin gene under the control of its own promoter could be functionally. introduced into some site, such as liver or skin. Cancer patients with hypercalcemia would be a group to whom this therapy could be applied.

Other gene therapies using TGT can include the use of a polynucleotide that has a therapeutic effect without being translated into a polypeptide. For example, TGT can be used in the delivery of anti-sense polynucleotides for turning off the expression of specific genes. Conventional anti-sense methodology suffers from poor efficacy, in part, because the oligonucleotide sequences delivered are too short. With TGT, however, full length anti-sense sequences can be delivered as easily as short oligomers. Anti-sense polynucleotides can be DNA or RNA molecules that themselves hybridize to (and, thereby, prevent transcription or translation of) an endogenous nucleotide sequence. Alternatively, an anti-sense DNA may encode an RNA the hybridizes to an endogenous sequence, interfering with translation. Other uses of TGT in this vein include delivering a polynucleotide that encodes a tRNA or rRNA to replace a defective or deficient endogenous tRNA or rRNA, the presence of which causes the pathological condition.

Cell-specific promoters can also be used to permit expression of the gene only in the target cell. For example, certain genes are highly promoted in adults only in particular types of tumors. Similarly, tissue-specific promoters for specialized tissue, e.g., lens tissue of the eye, have also been identified and used in heterologous expression systems.

Beyond the therapies described, the method of the invention can be used to deliver polynucleotides to animal stock to increase production of milk in dairy cattle or muscle mass in animals that are raised for meat.

DNA and mRNA Vaccines

According to the methods of the invention, both expressible DNA and mRNA can be delivered to cells to form therein a polypeptide translation product. If the nucleic acids contain the proper control sequences, they will direct the synthesis of relatively large amounts of the encoded protein. When the DNA and mRNA delivered to the cells codes for an immunizing peptide, the methods can be applied to achieve improved and more effective immunity against infectious agents, including intracellular viruses, and also against tumor cells.

Since the immune systems of all vertebrates operate similarly, the applications described can be implemented in all vertebrate systems, comprising mammalian and avian species, as well as fish.

The methods of the invention may be applied by direct injection of the polynucleotide into cells of the animal in vivo, or by in vitro transfection of some of the animal cells which are then re-introduced into the animal body. The polynucleotides may be delivered to various cells of the animal body, including muscle, skin, brain, lung, liver, spleen, or to the cells of the blood. Delivery of the polynucleotides directly in vivo is preferably to the cells of muscle or skin. The polynucleotides may be injected into muscle or skin using an injection syringe. They may also be delivered into muscle or skin using a vaccine gun.

It has recently been shown that cationic lipids can be used to facilitate the transfection of cells in certain applications, particularly in vitro transfection. Cationic lipid based transfection technology is preferred over other methods; it is more efficient and convenient than calcium phosphate, DEAE dextran or electroporation methods, and retrovirus mediated transfection, as discussed previously, can lead to integration events in the host cell genome that result in oncogene activation or other undesirable consequences. The knowledge that cationic lipid technology works with messenger RNA is a further advantage to this approach because RNA is turned over rapidly by intracellular nucleases and is not integrated into the host genome. A transfection system that results in high levels of reversible expression is preferred to alternative methodology requiring selection and expansion of stably transformed clones because many of the desired primary target cells do not rapidly divide in culture.

The ability to transfect cells at high efficiency with cationic liposomes provides an alternative method for immunization. The gene for an antigen is introduced in to cells which have been removed from an animal. The transfected cells, now expressing the antigen, are reinjected into the animal where the immune system can respond to the (now) endogenous antigen. The process can possibly be enhanced by coinjection of either an adjuvant or lymphokines to further stimulate the lymphoid cells.

Vaccination with nucleic acids containing a gene for an antigen may also provide a way to specifically target the cellular immune response. Cells expressing proteins which are secreted will enter the normal antigen processing pathways and produce both a humoral and cytotoxic response. The response to proteins which are not secreted is more selective. Non-secreted proteins synthesized in cells expressing only class I MHC molecules are expected to produce only a cytotoxic vaccination. Expression of the same antigen in cells bearing both class I and class. II molecules may produce a more vigorous response by stimulating both cytotoxic and helper T cells. Enhancement of the immune response may also be possible by injecting the gene for the antigen along with a peptide fragment of the antigen. The antigen is presented via class I MHC molecules to the cellular immune system while the peptide is presented via class II MHC molecules to stimulate helper T cells. In any case, this method provides a way to stimulate and modulate the immune response in a way which has not previously been possible.

A major disadvantage of subunit vaccines is that glycoprotein antigens are seldom modified correctly in the recombinant expression systems used to make the antigens. Introducing the gene for a glycoprotein antigen will insure that the protein product is synthesized, modified and processed in the same species and cells that the pathogen protein would be. Thus, the expression of a gene for a human viral glycoprotein will contain the correct complement of sugar residues. This is important because it has been demonstrated that a substantial component of the neutralizing antibodies in some viral systems are directed at carbohydrate epitopes.

Any appropriate antigen which is a candidate for an immune response, whether humoral or cellular, can be used in its nucleic acid form. The source of the cells could be fibroblasts taken from an individual which provide a convenient source of cells expressing only class I MHC molecules. Alternatively, peripheral blood cells can be rapidly isolated from whole blood to provide a source of cells containing both class I and class II MHC proteins. They could be further fractionated into B cells, helper T cells, cytotoxic T cells or macrophage/monocyte cells if desired. Bone marrow cells can provide a source of less differentiated lymphoid cells. In all cases the cell will be transfected either with DNA containing a gene for the antigen or by the appropriate capped and polyadenylated mRNA transcribed from that gene or a circular RNA, chemically modified RNA, or an RNA which does not require 5' capping. The choice of the transfecting nucleotide may depend on the duration of expression desired. For vaccination purposes, a reversible expression of the immunogenic peptide, as occurs on mRNA transfection, is preferred. Transfected cells are injected into the animal and the expressed proteins will be processed and presented to the immune system by the normal cellular pathways.

Such an approach has been used to produce cytotoxic immunity in model systems in mice. Cell lines, malignant continuously growing cells, can be stably transformed with DNA. When cells are injected into animals, they induce cellular immunity to the expressed antigen. The cationic lipid delivery system will allow this approach to be extended to normal, non-malignant cells taken from a patient.

There are several applications to this approach of targeting cellular immunity. The first is vaccination against viruses in which antibodies are known to be required or to enhanced viral infection. There are two strategies that can be applied here. One can specifically target the cellular pathway during immunization thus eliminating the enhancing antibodies. Alternatively one can vaccinate with the gene for a truncated antigen which eliminate the humoral epitomes which enhance infectivity.

The use of DNA or mRNA vaccine therapy could similarly provide a means to provoke an effective cytotoxic T-cell response to weakly antigenic tumors. We propose, for example, that if a tumor-specific antigen were expressed by mRNA inside a cell in an already processed form, and incorporated directly into the Class I molecules on the cell surface, a cytotoxic T cell response would be elicited.

A second application is that this approach provides a method to treat latent viral infections. Several viruses (for example, Hepatitis B, HIV and members of the Herpes virus group) can establish latent infections in which the virus is maintained intracellularly in an inactive or partially active form. There are few ways of treating such an infections. However, by inducing a cytolytic immunity against a latent viral protein, the latently infected cells will be targeted and eliminated.

A related application of this approach is to the treatment of chronic pathogen infections. There are numerous examples of pathogens which replicate slowly and spread directly from cell to cell. These infections are chronic, in some cases lasting years or decades. Examples of these are the slow viruses (e.g. Visna), the Scrapie agent and HIV. One can eliminate the infected cells by inducing an cellular response to proteins of the pathogen.

Finally, this approach may, also be applicable to the treatment of malignant disease. Vaccination to mount a cellular immune response to a protein specific to the malignant state, be it an activated oncogene, a fetal antigen or an activation marker, will result in the elimination of these cells.

The use of DNA/mRNA vaccines could in this way greatly enhance the immunogenicity of certain viral proteins, and cancer-specific antigens, that normally elicit a poor immune response. The mRNA vaccine technique should be applicable to the induction of cytotoxic T cell immunity against poorly immunogenic viral proteins from the Herpes viruses, non-A, non-B hepatitis, and HIV, and it would avoid the hazards and difficulties associated with in vitro propagation of these viruses. For cell surface antigens, such as viral coat proteins (e.g., HIV gp120), the antigen would be expressed on the surface of the target cell in the context of the major histocompatibility complex (MHC), which would be expected to result in a more appropriate, vigorous and realistic immune response. It is this factor that results in the more efficacious immune responses frequently observed with attenuated virus vaccines. Delivery of a single antigen gene by TGT would be much safer than attenuated viruses, which can result in a low frequency of disease due to inadequate attenuation.

There is an additional advantage of TGT which can be exploited during the vaccine development phase. One of the difficulties with vaccine development is the requirement to screen different structural variants of the antigen, for the optimal immune response. If the variant is derived from a recombinant source, the protein usually must be expressed and purified before it can be tested for antigenicity. This is a laborious and time consuming process. With in vitro mutagenesis, it is possible to obtain and sequence numerous clones of a given antigen. If these antigen can be screened for antigenicity at the DNA or RNA level by TGT, the vaccine development program could be made to proceed much faster.

Finally, in the case of the DNA/mRNA vaccines, the protein antigen is never exposed directly to serum antibody, but is always produced by the transfected cells themselves following translation of the mRNA. Hence, anaphylaxis should not be a problem. Thus, the present invention permits the patient to be immunized repeatedly without the fear of allergic reactions. The use of the DNA/mRNA vaccines of the present invention makes such immunization possible.

One can easily conceive of ways in which this technology can be modified to enhance still further the immunogenicity of antigens. T cell immunization can be augmented by increasing the density of Class I and Class II histocompatibility antigens on the macrophage or other cell surface and/or by inducing the transfected cell to release cytokines that promote lymphocyte proliferation. To this end, one may incorporate in the same liposomes that contain mRNA for the antigen, other mRNA species that encode interferons or interleukin-1. These cytokines are known to enhance macrophage activation. Their systemic use has been hampered because of side effects. However, when encapsulated in mRNA, along with mRNA for antigen, they should be expressed only by those cells that co-express antigen. In this situation, the induction of T cell immunity can be enhanced greatly.

Therapeutic Formulations

Polynucleotide salts: Administration of pharmaceutically acceptable salts of the polynucleotides described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., Journal of Pharmaceutical Sciences 66:1–19 (1977) the disclosure of which is hereby incorporated by reference.

Polynucleotides for injection, a preferred route of delivery, may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The container in which the polynucleotide is packaged is labeled, and the label bears a notice in the form prescribed by a governmental agency, for example the Food and Drug Administration, which notice is reflective of approval by the agency under Federal law, of the manufacture, use, or sale of the polynucleotide material therein for human administration.

Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. 301–392. Regulation for biologic material, comprising products made from the tissues of animals is provided under 42 U.S.C 262. Similar approval is required by most foreign countries. Regulations vary from country to country, but the indivdual procedures are well known to those in the art.

Dosage and Route of Administration

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tisues or lungs.

In preferred protocols, a formulation comprising the naked polynucleotide in an aqueous carrier is injected into tissue in amounts of from 10 $\mu$l per site to about 1 ml per site. The concentration of polynucleotide in the formulation is from about 0.1 $\mu$g/ml to about 20 mg/ml.

Regulation of TGT

Just as DNA based gene transfer protocols require appropriate signals for transcribing (promoters, enhancers) and processing (splicing signals, polyadenylation signals) the mRNA transcript, mRNA based TGT requires the appropriate structural and sequence elements for efficient and correct translation, together with those elements which will enhance the stability of the transfected mRNA.

In general, translational efficiency has been found to be regulated by specific sequence elements in the 5' non-coding or untranslated region (5'UTR) of the RNA. Positive sequence motifs include the translational initiation consensus sequence (GCC)$^A$CC$\underline{ATG}$G (Kozak, Nucleic Acids Res.15:8125 (1987)) and the $5^G$ 7 methyl GpppG cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, Supra, Rao et al., Mol. and Cell. Biol. 8:284(1988)). In addition, certain sequence motifs such as the beta globin 5' UTR may act to enhance translation (when placed adjacent to a heterologous 5' UTR) by an unknown mechanism. There are also examples of specific 5' UTR sequences which regulate eukaryotic translational efficiency in response to environmental signals. These include the human ferritin 5' UTR (Hentze et al., Proc. Natl. Acad. Sci. USA 84:6730 (1987)) and the drosophila hsp$^7$0 5' UTR (Klemenz et al., EMBO Journal 4:2053 (1985)). Finally, there are viral 5' UTR sequences which are able to bypass normal cap dependant translation and translational controls and mediate ann efficient translation of viral or chimeric mRNAs (Dolph et al., J. of Virol. 62:2059 (1988)), Pelletier and Sonnenberg, Nature 334, 320 (1988)). mRNA based TGT protocols must therefore include appropriate 5' UTR translational elements flanking the coding sequence for the protein of interest.

In addition to translational concerns, mRNA stability must be considered during the development of mRNA based TGT protocols. As a general statement, capping and 3' polyadenylation are the major positive determinants of eukaryotic mRNA stability (Drummond, supra; Ross, Mol. Biol. Med. 5:1(1988)) and function to protect the 5' and 3' ends of the mRNA from degradation. However, regulatory elements which affect the stability of eukaryotic mRNAs have also been defined, and therefore must be considered in the development of mRNA TGT protocols. The most notable and clearly defined of these are the uridine rich 3' untranslated region (3' UTR) destabilizer sequences found in many short half-life mRNAs (Shaw and Kamen Cell 46:659 (1986)), although there is evidence that these are not the only sequence motifs which result in mRNA destabilization (Kabnick and Housman, Mol. and Cell. Biol. 8:3244 (1988)). In addition, specific regulatory sequences which modulate cellular mRNA half life in response to environmental stimuli have also been demonstrated. These include the estrogen mediated modulation of Vitellogenin mRNA stability (Brock and Shapiro, Cell 34:207 (1983)), the iron dependant regulation of transferrin receptor mRNA stability (Mullner and Kuhn, Cell 53:815 (1988)) which is due to a specific 3' UTR motif, the prolactin mediated control of Casein mRNA stability (Guyette et al., Cell 17:1013 (1989)), the regulation of Fibronectin mRNA stability in response to a number of stimuli (Dean et al., J. Cell. Biol. 106:2159 (1988)), and the control of Histone mRNA stability (Graves et al., Cell 48:615 (1987)). Finally, just as viral RNA sequences have evolved which bypass normal eukaryotic mRNA translational controls, likewise some viral RNA sequences seem to be able to confer stability in the absence of 3' polyadenylation (McGrae and Woodland, Eur. J. of Biochem. 116: 467 (1981)). Some 5', such as EMC, according to Example 21, are known to function without a cap. This cacophony of stability modulating elements must also be carefully considered in developing mRNA based TGT protocols, and can be used to modulate the effect of an mRNA treatment.

Liposome-forming Materials

The science of forming liposomes is now well developed. Liposomes are unilamellar or multilamellar vesicles, having a membrane portion formed of lipophilic material and an interior aqueous portion. The aqueous portion is used in the present invention to contain the polynucleotide material to be delivered to the target cell.

It is preferred that the liposome forming materials used herein have a cationic group, such as a quaternary ammonium group, and one or more lipophilic groups, such as saturated or unsaturated alkyl groups having from about 6 to about 30 carbon atoms. One group of suitable materials is described in European Patent Publication No. 0187702. These materials have the formula:

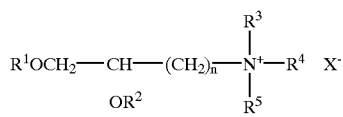

wherein $R^1$ and $R^2$ are the same or different and are alkyl or alkenyl of 6 to 22 carbon atoms, $R^3$, $R^4$, and $R^5$ are the same or different and are hydrogen, alkyl of 1 to 8 carbons, aryl, aralkyl of 7 to 11 carbons, or when two or three of $R^3$, $R^4_1$ and $R^5$ are taken together they form quinuclidino, piperidino, pyrrolidino, or morpholino; n is 1 to 8, and X is a pharmaceutically acceptable anion, such as a halogen. These compounds may be prepared as detailed in the above-identified patent application; alternatively, at least one of these compounds, N-(2,3-di-(9-(Z)-octadecenyloxy))-prop-1-yl-N,N,N-trimethylammonium chloride (DOTMA), is commercially available from Bethesda Research Laboratories (BRL), Gaithersburg, Md. 20877, USA.

These quaternary ammonium diether compounds, however, do have some drawbacks. Because of the ether linkages, they are not readily metabolized in vivo. When long-term therapy is contemplated, there is some possibility that these materials could accumulate in tissue, ultimately resulting in lipid storage disease and toxic side effects. Accordingly, a preferred class of compositions for use in the present invention has the formula:

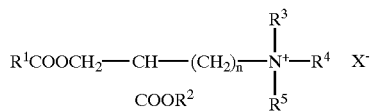

wherein $R^1$ and $R^2$ are the same or different and are alkyl or alkenyl of 5 to 21 carbon atoms, $R^3$, $R^4$, and $R^5$ are the same or different and are hydrogen, alkyl of 1 to 8 carbons, aryl, aralkyl of 7 to 11 carbons, or when two or three of $R^3$, $R^4$, and $R^5$ are taken together they form quinuclidino, piperidino, pyrrolidino, or morpholino; n is 1 to 8, and X is a pharmaceutically acceptable anion, such as a halogen. These compounds may be prepared using conventional techniques, such as nucleophilic substitution involving a carboxylic acid and an alkyl halide, by transesterification, or by condensation of an alcohol with an acid or an acid halide.

Moreover, many suitable liposome-forming cationic lipid compounds are described in the literature. See, e.g., L. Stamatatos, et al., Biochemistry 27:3917–3925 (1988); H. Eibl, et al., Biophysical Chemistry 10:261–271 (1979).

Liposome Preparation

Suitable liposomes for use in the present invention are commercially available. DOTMA liposomes, for example, are available under the trademark Lipofectin from Bethesda Research Labs, Gaithersburg, Md.

Alternatively, liposomes can be prepared from readily-available or freshly synthesized starting materials of the type previously described. The preparation of DOTAP liposomes is detailed in Example 6. Preparation of DOTMA liposomes is explained in the literature, see, e.g., P. Felgner, et al., Proc. Nat'l Acad. Sci. USA 84:7413–7417. Similar methods can be used to prepare liposomes from other cationic lipid materials. Moreover, conventional liposome forming, materials can be used to prepare liposomes having negative charge or neutral charge. Such materials include phosphatidyl choline, cholesterol, phosphatidyl-ethanolamine, and the like. These materials can also advantageously be mixed with the DOTAP or DOTMA starting materials in ratios from 0% to about 75%.

Conventional methods can be used to prepare other, noncationic liposomes. These liposomes do not fuse with cell walls as readily as cationic liposomes. However, they are taken up by macrophages in vivo, and are thus particularly effective for delivery of polynucleotide to these cells. For example, commercially dioleoyl-phosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15° C. Alternatively, negatively charged vesicles can be prepared without sonication to produce multilamellar vesicles or by extrusion through nucleopore membranes to produce unilamellar vesicles of discrete size. Other methods are known and available to those of skill in the art.

The present invention is described below in detail using the 23 examples given below; however, the methods described are broadly applicable as described herein and are not intended to be limited by the Examples.

EXAMPLE 1

Preparation of Liposome-Forming DOTAP

The cationic liposome-forming material 1,2-bis (oleoyloxy)-3-(trimethylammonio)propane (DOTAP) is prepared as reported by L. Stamatatos, et al. (supra) or H. Eibl, et al. (supra).

Briefly, Stamatatos, et al. report that 1 mmol of 3-bromo-1,2-propanediol (Aldrich) was acylated for 48 hours at 20° C. with 3 mmol of oleyl chloride (freshly prepared from oleic acid and oxaloyl chloride) in dry, alcohol-free diethyl ether (20 ml) containing 5 mmol of dry pyridine. The precipitate of pyridinium hydrochloride was filtered off, and the filtrate was concentrated under nitrogen and redissolved in 10 ml of hexane. The hexane solution was washed 3 times with an equal volume of 1:1 methanol/0.1 N aqueous NCOONa, pH 3.0, 3 times with 1:1 methanol/0.1 N aqueous NaOH, an dl time with 1% aqueous NaCl. The crude 3-bromo-1,2-bis-(oleolyloxy)propane was then stirred for 72 hours in a sealed tube with a solution of 15% trimethylamine in dry dimethyl sulfoxide (30 ml) at 25° C. The products of this reaction were dissolved in chloroform (200 ml), which was repeatedly washed with 1:1 methanol/100 mM aqueous HCOONa, pH 3.0, and then evaporated in vacuo to yield a light yellow oil. This material was purified on a column of silicic acid (Bio-Sil A, Bio-Rad Laboratories), eluting with a 0–15% gradient of methanol in chloroform to give the desired product in pure form at 9–10% methanol. The purified product was a colorless, viscous oil that migrates with an $R_f$ of 0.4 on thin layer chromatography plates (silica gel G) that were developed with 50:15:5:5:2 $CHCl_3$/acetone/$CH_3OH$/$CH_3COOH$/$H_2O$.

EXAMPLE 2

Preparation of Plasmids for Making DNA Templates for Any Gene of Interest

Suitable template DNA for production of mRNA coding for a desired polypeptide may be prepared in accordance with standard recombinant DNA methodology. As has been previously reported (P. Kreig, et al., Nucleic Acids Res. 12:7057–7070 (1984)), a 5' cap facilitates translation of the mRNA. Moreover, the 3' flanking regions and the poly A tail are believed to increase the half life of the mRNA in vivo.

The readily-available SP6 cloning vector pSP64T provides 5' and 3' flanking regions from β-globin, an efficiently translated mRNA. The construction of this plasmid is detailed by Kreig, et al. (supra), and is hereby incorporated by this reference. Any cDNA containing an initiation codon can be introduced into this plasmid, and mRNA can be prepared from the resulting template DNA. This. particular plasmid can be cut with. BglII. to insert any desired cDNA coding for a polypeptide of interest.

Although good results can be obtained with pSP64T when linearized and then transcribed in vivo with SP6 RNA polymerase, we prefer to use the xenopus β-globin flanking sequences of pSP64T with phage T7 RNA polymerase. These flanking sequences are purified from pSP64T as the small (approx. 150 bp) HindIII to EcoRI fragment. These sequences are then inserted into a purified linear HindIII/EcoRI fragment (approx. 2.9k bp) from pIBI 31 (commercially available from International Biotechnologies, Inc., Newhaven, Conn. 06535) with T4 DNA ligase. Resulting plasmids, designated pXGB, are screened for orientation and transformed into E. coli. These plasmids are adapted to receive any gene of interest at a unique BglII restriction site, which is situated between the two xenopus β-globin sequences.

EXAMPLE 3

Preparation of Plasmid Coding for Chloramphenicol Acetyltransferase

A convenient marker gene for demonstrating in vivo expression of exogenous polynucleotides is chloramphenicol acetyltransferase, CAT. A plasmid pSP-CAT containing the CAT gene flanked by the xenopus β-globin 5' and 3' sequences was produced by adding the CAT gene into the BglII site of pSP64T. We used CAT gene in the form of the small BamHI/HindIII fragment from pSV2-CAT (available from the American Type Culture Collection, Rockville, Md., Accession No. 37155). However, the CAT gene is commonly used in molecular biology and is available from numerous sources. Both the CAT BamHI/HindIII fragment and the BglII-cleaved pSP64T were incubated with the Klenow fragment to generate blunt ends, and were then ligated with T4 DNA ligase to form pSP-CAT.

The small PstI/HindIII fragment was then generated and purified, which comprises the CAT gene between, the 5' and 3' β-globin flanking sequences of pSP64T. pIBI31 (International Biotechnologies, Inc.) was cleaved with PstI and HindIII, and the long linear sequence was purified. This fragment was then combined with the CAT-gene containing sequence and the fragments were ligated with T4 DNA ligase to form a plasmid designated pT7CAT An. Clones are selected on the basis of β-galactosidase activity, with Xgal and ampicillin resistance.

EXAMPLE 4

Preparation of Purified DNA Template

The plasmid DNA from Example 3 is grown up and prepared as per Maniatis (supra), except without RNAse, using 2 CsCl spins to remove bacterial RNA. Specifically, E. coli containing pT7CAT An from Example 3 was grown up in ampicillin-containing LB medium. The cells were then pelleted, by spinning at 5000 rpm for 10 min. in a Sorvall RC-5 centrifuge (E.I. DuPont, Burbank, Calif. 91510), resuspended in cold TE, pH 8.0, centrifuged again for 10 min. at 5000 rpm., resuspended in a solution of 50 mM glucose, 25 mM Tris-Cl pH 8.0, 10 mM EDTA, and 40 mg/ml lysozyme. After incubation for 5 to 10 minutes with occasional inversion, 0.2 N NaOH containing 1% SDS was added, followed after 10 minutes at 0° C. with 3 M potassium acetate and 2 M acetic acid. After 10 more minutes, the material was again centrifuged. at 6000 rpm, and the supernatant was removed with a pipet. The pellet was then mixed into 0.6 vol. isopropanol (−20° C.), mixed, and stored at −20° C. for 15 minutes. The material was then centrifuged again at 10,000 rpm for 20 min., this time in an HB4 swinging bucket rotor apparatus (DuPont, supra) after which the supernatant was removed and the pellet was washed in 70% EtOH and dried at room temperature. Next, the pellet was resuspended in 3.5 ml TE, followed by addition of 3.4 g CsCl and 350 µl of 5 mg/ml EtBr. The resulting material was placed in a quick seal tube, filled to the top with mineral oil. The tube was spun for 3.5 hours at 80,000 rpm in a VTi80 centrifuge (Beckman Instruments, Pasadena, Calif., 91051). The band was removed, and the material was centrifuged again, making up the volume with 0.95 g CsCl/ml and 0.1 ml or 5 mg/ml EtBr/ml in TE. The EtBr was then extracted with an equal volume of TE saturated N-Butanol after adding 3 volumes of TE to the band, discarding the upper phase until the upper phase is clear. Next, 2.5 vol. EtOH was added, and the material was precipitated at −20° C. for 2 hours. The resultant DNA precipitate is used as a DNA template for preparation of mRNA in vitro.

EXAMPLE 5

Preparation of mRNA for Transfection

The DNA from Example 4 was linearized downstream of the poly A tail with a 5-fold excess of PstI. The linearized DNA was then purified with two phenol/chloroform extractions, followed by two chloroform extractions. DNA was then precipitated with NaOAc (0.3 M) and 2 volumes of EtOH. The pellet was resuspended at about 1 mg/ml in DEP-treated deionized water.

Next, a transcription buffer was prepared, comprising 400 mM Tris-HCl (pH 8.0), 80 mM $MgCl_2$, 50 mM DTT, and 40 mM spermidine. Then, the following materials were added in order to one volume of DEP-treated water at room temperature: 1 volume T7 transcription buffer, prepared above; rATP, rCTP, and rUTP to 1 mM concentration; rGTP to 0.5 mM concentration; 7meG(5')ppp(5')G cap analog (New England Biolabs, Beverly, Mass., 01951) to 0.5 mM concentration; the linearized DNA template prepared above to 0.5 mg/ml concentration; RNAsin (Promega, Madison, Wis.) to 2000 U/ml concentration; and T7 RNA polymerase (N.E. Biolabs) to 4000 U/ml concentration.

This mixture was incubated for 1 hour at 37 C. The successful transcription reaction was indicated by increasing,cloudiness of the reaction mixture.

Following generation of the mRNA, 2 U RQ1 DNAse (Promega) per microgram of DNA template used was added and. was permitted to digest the template for 15 minutes. Then, the RNA was extracted twice with chloroform/phenol and twice with chloroform. The supernatant was precipitated with 0.3 M NaOAc in 2 volumes of EtOH, and the pellet was. resuspended in 100 µl DEP-treated deionized water per 500 µl transcription product. This solution was passed over an RNAse-free Sephadex G50 column (Boehringer Mannheim #100 411). The resultant mRNA was sufficiently pure to be used in transfection of vertebrates in vivo.

EXAMPLE 6

Preparation of Liposomes

A number of liposome preparation methods can be used to advantage in the practice of the present invention. One particularly preferred liposome is made from DOTAP as follows:

A solution of 10 mg dioleoyl phosphatidylethanolamine (PE) and 10 mg DOTAP (from Example 1) in 1 ml chloroform is evaporated to dryness under a stream of nitrogen, and residual solvent is removed under vacuum overnight. Liposomes are prepared by resuspending the lipids in deionized water (2 ml) and sonicating to clarity in a closed vial. These preparations are stable for at least 6 months.

Polynucleotide complexes were prepared by mixing 0.5 ml polynucleotide solution (e.g., from Example 5) at 0.4 mg/ml by slow addition through a syringe with constant gentle vortexing to a 0.5 ml solution of sonicated DOTMA/PE or DOTAP/PE liposomes at 20 mg/ml, at room temperature. This procedure results in positively charged complexes which will spontaneously deliver the polynucleotide into cells in vivo. Different ratios of positively charged liposome to polynucleotide can be used to suit the particular need in any particular situation. Alternatively, as reported by Felgner, et al. (supra), it may be advantageous to dilute the polynucleotide (DNA or RNA) with Hepes buffered saline (150 mM NaCl; 20 mM Hepes, pH 7.4) prior to combining the materials to spontaneously form liposome/polynucleotide complexes. In many instances, however, the use of solutions having low ionic strength (such as sucrose) instead of saline solution is believed to be preferable; in particular, it is believed that such solutions facilitate delivery of polynucleotide to the cell by minimizing precipitation of polynucleotide/lipid complex.

EXAMPLE 7

In vivo Expression of Liposomally and Non-Liposomally Introduced mRNA in the Rat The ability of mRNA coding for chloramphenicol acetyl transferase (CAT) to transfect cells in vivo and the subsequent expression of the CAT protein was demonstrated by directly injecting 0.200 ml of each of the formulations below, prepared as indicated, into the abdominal muscle of rats, forming a bleb. Six replicates of each formulation were tested. After 12 to 14 h, the segment of the abdominal muscle into which the injection was made, weighing approximately 0.1 to 0.2 grams, was excised, minced, and placed in a 1.5 ml disposable mortar (Kontes, Morton Grove, Ill.) together with 200 µl of the an aqueous formulation having the following components: 20 mM Tris, pH 7.6; 2 mM $MgCl_2$; and 0.1% Triton X-100 surfactant. The contents of the mortar were then ground for 1 minute with a disposable pestle. The mortar was then covered (with Parafilm) and placed in a 1 liter Parr cell disrupter bomb (Parr Instrument Company, Moline, Ill.) and pressurized to 6 atmospheres with nitrogen at 4° C. After 30 minutes, the pressure was quickly released to disrupt the tissue and produce a crude lysate. The lysate was then centrifuged in a microcentrifuge at 13,000 rpm, 4° C., for 10 minutes. The supernatant was then decanted and stored at −20° C. until analyzed.

The lysates were then assayed for the presence of the CAT protein by thin-layer chromatography. First, 75 µl of each sample (the supernatant prepared above) was incubated for two hours at 37° C. with 5 µl $C^{14}$ chloramphenicol (Amersham); 20 µl 4 mM Acetyl CoA; and 50 µl M Tris, pH 7.8. Thereafter, 20 µl of 4 mM Acetyl CoA was added, and the mixture was again incubated for 2 hours at 37° C. The resulting solution was extracted with 1 ml EtOAc, and the organic phase was removed and lyophilized in a vacuum centrifuge (SpeedVac, Savant Co.). The pellet was resuspended in 20 µl EtOAc, and was spotted onto a silica gel thin layer chromatography plate. The plate was developed for 45 minutes in 95% chloroform/5% methanol, was dried, and was sprayed with a radioluminescent indicator (Enhance Spray for Surface Radiography, New England Nuclear Corp.). The plate was then sandwiched with Kodak XAR5 film with overnight exposure at −70° C., and the film was developed per manufacturer's instructions. The following results were obtained:

| FORMULATION | mRNA Expression (No. positive/total) |
|---|---|
| 1. 1 ml Optimem; 37.5 µg DOTMA | 0/6 |
| 2. 1 ml Optimem; 15 µg CAT RNA | 3/6 |
| 3. Formulation 1 plus 15 µg CAT RNA | 4/6 |
| 4. 10% Sucrose; 37.5 µg DOTMA; 15 µg CAT RNA | 3/6 |
| 5. 10% Sucrose; 187 µg DOTMA; 75 µg CAT RNA | 0/6 |

Optimem: Serum-free media (Gibco Laboratories, Life Technologies, Inc, Grand Island, N.Y. 14072)
DOTMA: (Lipofectin brand; Bethesda Research Labs, Gaithersburg, MD)
CAT RNA: From Example 5
All formulations made up in DEPC-treated RNAse-free water
(International Biotechnologies, Inc., New Haven, CT 06535).

EXAMPLE 8 mRNA Vaccination of Mice to Produce the gp120Protein of HIV Virus

A liposomal formulation containing mRNA coding for the gp120 protein of the HIV virus is prepared according to Examples 1 through 5, except that the gene for gp120 (pIIIenv3-1 from the Aids Research and Reagent Program, National Institute of Allergy and Infectious Disease, Rockville, Md. 20852) is inserted into the plasmid pXBG in the procedure of Example 4. A volume of 200 al of a formulation, prepared according to Example 6, and containing 200 µg/ml of gp120 mRNA and 500 µg/ml 1:1 DOTAP/PE in 10% sucrose is injected into the tail vein of mice 3 times in one day. At about 12 to 14 h after the last injection, a segment of muscle is removed from the injection site, and prepared as a cell lysate according to Example 7. The HIV specific protein gp120 is identified in the lysate also according to the procedures of Example 7.

The ability of gp120 antibody present in serum of the mRNA vaccinated mice to protect against HIV infection is determined by a HT4-6C plaque reduction assay, as follows:

HT4-6C cells (CD4+ HeLa cells) are obtained from Dr. Bruce Chesebro, (Rocky Mountain National Lab, Montana) and grown in culture in RPMI media (BRL, Gaithersburg, Md.). The group of cells is then divided into batches. Some of the batches are infected with HIV by adding approximately $10^5$ to $10^6$ infectious units of HIV to approximately $10^7$ HT4-6C cells. Other batches are tested for the protective effect of gp120 immune serum against HIV infection by adding both the HIV and approximately 50 µl of serum from a mouse vaccinated with gp120 mRNA. After 3 days of incubation, the cells of all batches are washed, fixed and stained with crystal violet, and the number of plaques counted. The protective effect of gp120 immune serum is determined as the reduction in the number of plaques in the batches of cells treated with both gp120 mRNA-vaccinated mouse serum and HIV compared to the number in batches treated with HIV alone.

EXAMPLE 9 mRNA Vaccination of Human Stem Cell-Bearing SCID Mice with nef mRNA Followed by HIV Challenge Severe combined immunodeficient mice (SCID mice (Molecular Biology Institute, (MBI), La Jolla, Calif. 92037)) were reconstituted with adult human peripheral blood lymphocytes by injection into the peritoneal cavity according to the method of Mosier (Mosier et al., Nature 335:256 (1988)). Intraperitoneal injection of 400 to 4000 infectious units of HIV-1 was then performed. The mice were maintained in a P3 level animal containment facility in sealed glove boxes.

MRNA coding for the nef protein if HIV was prepared by obtaining the nef gene in the form of a plasmid (pGM92, from the NIAID, Rockville, Md. 20852); removing the nef gene from the plasmid; inserting the nef gene in the pXBG plasmid for transcription; and purifying the transcription product nef mRNA as described in Examples 2 through 5. The nef mRNA was then incorporated into a formulation according to Example 6. 200 microliter tail vein injections of a 10% sucrose solution containing 200 µg/ml NEF RNA and 500 µg/ml 1:1 DOTAP:DOPE (in RNA/liposome complex form) were performed daily on experimental animals, while control animals were likewise injected with RNA/liposome complexes containing 200 µg/ml yeast tRNA and 500 µg/ml 1:1 DOTAP/DOPE liposomes. At 2, 4 and 8 weeks post injection, biopsy specimens were obtained from injected lymphoid organs and prepared for immunohistochemistry. At the same time points, blood samples were obtained and assayed for p24 levels by means of an ELISA kit (Abbott Labs, Chicago, Ill.) and virus titer by the plaque assay of Example 8. Immunostaining for HIV-1 was performed as described (Namikawa et al., Science 242:1684 (1988)) using polyclonal serum from a HIV infected patient. Positive cells were counted and the number of infected cells per high power field (400×) were determined. Using these assays, at least a 2 fold reduction in the number of positive staining cells was observed at 8 weeks, and titer and p24 expression was reduced by at least 50%. Together, these results indicate a moderate anti-viral effect of the (in vivo) treatment. A volume of 200 µl of the formulation, containing 200 µg/ml of nef mRNA, and 500 µg/ml 1:1 DOTAP:DOPE in 10% sucrose is injected into the tail vein of the human stem cell-containing SCID mice 3 times in one day. Following immunization, the mice are challenged by infection with an effective dose of HIV virus. Samples of blood are periodically withdrawn from the tail vein and monitored for production of the characteristic HIV protein p24 by an ELISA kit assay (Abbott Labs, Chicago, Ill.).

EXAMPLE 10

A Method of Providing Adenosine Deaminase to Mice by in vivo mRNA Transfection

The full-length sequence for the cDNA of the human adenosine deaminase (ADA) gene is obtained from the 1,300 bp EcoR1-AccI fragment of clone ADA 211 (Adrian, G. et al. Mol. Cell Biol. 4:1712 (1984). It is blunt-ended, ligated to BgIII linkers and then digested with BgIII. The modified fragment is inserted into the BgIII site of pXBG. ADA mRNA is transcribed and purified according to Examples 2 through 5, and purified ADA mRNA is incorporated into a formulation according to Example 6. Balb 3T3 mice are injected directly in the tail vein with 200 µl of this formulation, containing 200 µg/ml of ADA mRNA, and 500 µg/ml DOTAP in 10% sucrose.

The presence of human ADA in the tissues of the liver, skin, and muscle of the mice is confirmed by an isoelectric focusing (IEF) procedure. Tissue extracts were electrofocused between pH 4 and 5 on a non-denaturing gel. The gel was then stained for in situ ADA activity as reported by Valerio, D. et al. Gene 31:137–143 (1984).

A preliminary separation of human and non-human ADA is carried out by fast protein liquid chromatography (FPLC). The proteins are fractionated on a Pharmacia (Piscataway, N.J.) MonoQ column (HR5/5) with a linear gradient from 0.05 to 0.5 M KCl, 20 mM Tris (pH 7.5). Activity for ADA within the fractions is measured by reacting the fractions with $^{14}C$-adenosine (Amersham, Chicago, Ill.) which is converted to inosine. Thin layer chromatography (0.1 M NaPi pH 6.8 saturated ammonium sulfate:n-propylalcohol/100:60:2) is used to separate the radioactive inosine from the substrate adenosine.

EXAMPLE 11

In vivo Expression of Pure RNA and DNA Injected Directly into the Muscles of Mice The quadriceps muscles of mice were injected with either 100 µgrams of pRSVCAT DNA plasmid or 100 µgrams of βgCATβgA$_n$ RNA and the muscle tissue at the injection site later-tested for CAT activity.

Five to six week old female and male Balb/C mice were anesthetized by intraperitoneal injection with 0.3 ml of 2.5% Avertin. A 1.5 cm incision was made on the anterior thigh, and the quadriceps muscle was directly visualized. The DNA and RNA were injected in 0.1 ml of solution in a 1 cc syringe through a 27 gauge needle over one minute, approximately 0.5 cm from the distal insertion site of the muscle into the knee and about 0.2 cm deep. A suture was placed over the injection site for future localization, and the skin was then closed with stainless steel clips.

3T3 mouse fibroblasts were also transfected in vitro with 20 μg of DNA or RNA complexed with 60 μg of Lipofectin™ (BRL) in 3 ml of Opti-Mem™ (Gibco), under optimal conditions described for these cells (Malone, R. et al. *Proc. Nat'l. Acad. Sci. USA* 86:6077–6081(1989). The same fibroblasts were also transfected using calcium phosphate according to the procedure described in Ausubel et al.(Eds) *Current Protocols in Molecular Biology,* John Wiley and Sons, New York (1989).

The pRSVCAT DNA plasmid and βgCATβgA$_n$ RNA were prepared as described in the preceding examples. The RNA consisted of the chloramphenicol acetyl transferase (CAT) coding sequences flanked by 5' and 3' β-globin untranslated sequences and a 3' poly-A tract.

Muscle extracts were prepared by excising the entire quadriceps, mincing the muscle into a 1.5 ml microtube containing 200 μl of a lysis solution (20 mM Tris, pH 7.4, 2 mM MgCl$_2$ and 0.1% Triton X), and grinding the muscle with a plastic pestle (Kontes) for one minute. In order to ensure complete disruption of the muscle cells, the muscle tissue was then placed under 600 psi of N$_2$ in a bomb (Parr) at 4° C. for 15 min before releasing the pressure.

Fibroblasts were processed similarly after they were trypsinized off the plates, taken up into media with serum, washed 2× with PBS, and the final cell pellet suspended into 200 μl of lysis solution. 75 μl of the muscle and fibroblast extracts were assayed for CAT activity by incubating the reaction mixtures for 2 hours with $C^{14}$-chloramphenicol, followed by extraction and thin-layer chromatography, all as described in Example 7.

FIG. 1 comprises autoradiograms from two separate experiments showing CAT activity within extracts of the injected quadriceps muscles. Lane numbers appear at the top of the autoradiograms and the % chloramphenicol conversions are at the bottom. Sample locations are as follows:

Lanes 1 and 13: Control fibroblasts
Lanes 2 and 14: Muscle injected only with 5% sucrose
Lanes 3 and 15: 0.005 units of non-injected, purified CAT standard
Lanes 4 and 16: 0.05 units of purified CAT (Sigma)
Lanes 5 to 8: Muscle injected with 100 μg of βgCATβgA$_n$ RNA in 5% sucrose
Lanes 11, 12, and 17 to 20: Muscle injected with 100 μgrams pRSVCAT DNA in 5% sucrose
Lanes 9 and 10: 2.0 μgrams of βgCATβgA$_n$ RNA, lipofected, with 60 μgrams of DOTMA, into a 70% confluent 60 mm plate of 3T3 cells (10$^6$)
Lanes 21, 22: 20 μgrams of pRSVCAT lipofected, with 60 μg of DOTMA, into a 50% confluent 60 mm plate of 3T3 cells
Lanes 23, 24: 20 μg of pRSVCAT calcium phosphate lipofected into a 50% confluent 60 mm plate of 3T3 cells.

CAT activity was readily detected in all four RNA injection sites 18 hours after injection and in all six DNA injection sites 48 hours after injection. Extracts from two of the four RNA injection sites (FIG. 1, lanes 6 and 8) and from two of the six DNA injection sites (FIG. 1, lanes 11 and 20) contained levels of CAT activity comparable to the levels of CAT activity obtained from fibroblasts transiently transfected in vitro under optimal conditions (FIG. 1, lanes 9, 10, 21–24). The average total amount of CAT activity expressed in muscle was 960 pg for the RNA injections and 116 pg for the DNA injections. The variability in CAT activity recovered from different muscle sites probably represents variability inherent in the injection and extraction technique, since significant variability was observed when pure CAT protein or pRSVCAT-transfected fibroblasts were injected into the muscle sites and immediately excised for measurement of CAT activity. CAT activity was also recovered from abdominal muscle injected with the RNA or DNA CAT vectors, indicating that other muscle groups can take up and express polynucleotides.

EXAMPLE 12

Site of in vivo Expression of Pure DNA Injected Directly into the Muscles of Mice The site of gene expression in injected muscle was determined by utilizing the pRSVLac-Z DNA vector (P. Norton and J. Coffin *Molec. Cell Biol.* 5:281–290 (1985)) expressing the *E. coli* β-galactosidase gene for injection and observing the In situ cytochemical staining of muscle cells for *E. coli* β-galactosidase activity. The quadriceps muscle of mice was exposed as described in the previous example. Quadriceps muscles were injected once with 100 μg of pRSVLAC-Z DNA in 20% sucrose. Seven days later the individual quadriceps muscles were removed in their entirety and every fifth 15 μm cross-section was histochemically stained for β-galactosidase activity.

The muscle biopsy was frozen in liquid N$_2$-cooled isopentane. 15 μm serial sections were sliced using a cryostat and placed immediately on gelatinized slides. The slide were fixed in 1.5% glutaraldehyde in PBS for 10 minutes and stained 4 hours for β-galactosidase activity (J. Price. et al. *Proc. Nat'l Acad. Sci. USA* 84:156–160 (1987). The muscle was counterstained with eosin.

The photographed sections (FIG. 2) are as follows:
(A) and (B): Cross-sections of a muscle injected with pRSVLacZ at 25× and 160× magnification. respectively.
(C): A longitudinal section of another muscle injected with pRSVLacZ 160×.
(D), (E), and (F): Serial cross-sections of the same muscle that are 0.6 mm apart.

Figure 2A:
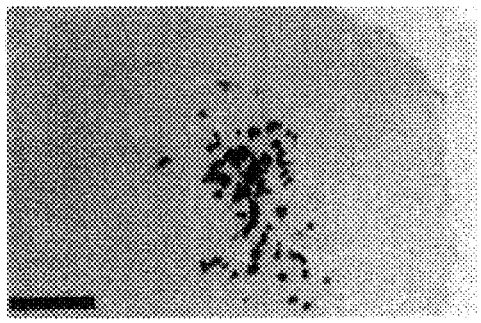
FIGS. 2A to 2F comprise photomicrographs of muscle tissue stained for beta-gabetosidase activity following injection with the pRSVLac-Z DNA vector.
Figure 2D:
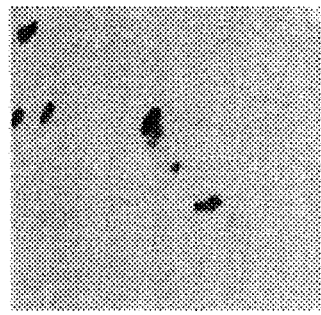
Figure 2B:
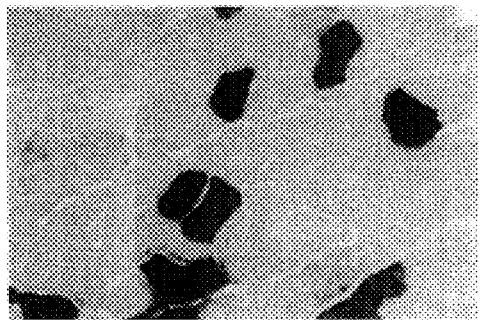
Figure 2E:
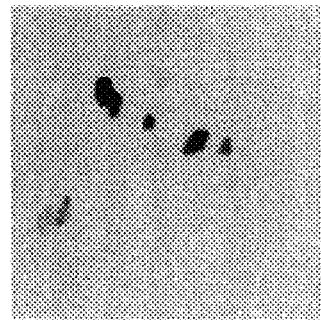
Figure 2C:
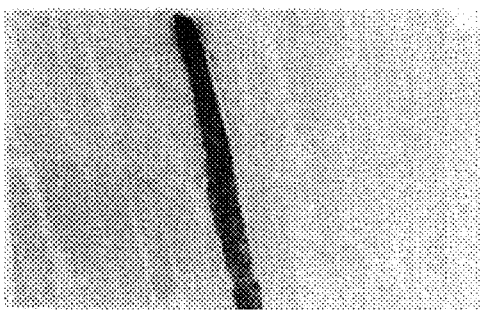
Figure 2F:
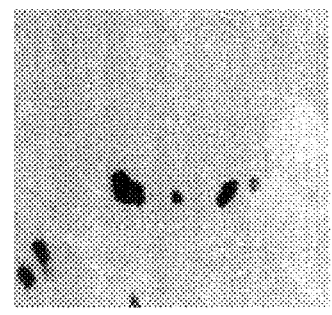

Approximately 60 muscle cells of the approximately 4000 cells (1.5%) that comprise the entire quadriceps and approximately 10–30% of the cells within the injection area were stained blue (FIGS. 2A and 2B). Control muscle injected with only a 20% sucrose solution did not show any background staining. Positive B-galactosidase staining within some individual muscle cells was at least 1.2 mm deep on serial cross-sections (FIGS. 2D, 2E, and 2F), which may be the result of either transfection into multiple nuclei or the ability of cytoplasmic proteins expressed from one nucleus to he distributed widely within the muscle cell. Longitudinal sectioning also revealed β-galactosidase staining within muscle cells for at least 400 mm (FIG. 2C). In cells adjacent to intensely blue cells, fainter blue staining often appeared in their bordering areas. This most likely represents an artifact of the histochemical β-galactosidase stain in which the reacted X-gal product diffuses before precipitating.

Similar results are obtained with linear DNA.

EXAMPLE 13

Dose-Response Effects of RNA and DNA Injected into Muscles of Mice

Experiments with the firefly luciferase reporter gene (LUC) explored the effect of parameters of dose level and time on the total luciferase extracted from injected muscle.

The RNA and DNA vectors were prepared, and the quadriceps muscles of mice injected as previously described. Muscle extracts of the entire quadriceps were prepared as described in Example 11, except that the lysis buffer was 100 mM KPi pH 7.8, 1 mM DTT, and 0.1% Triton X. 87.5 µl of the 200 µl extract was analyzed for luciferase activity (J. de Wet et al. *Molec. Cell Biol.* 7:725–737(1987)) using an LKB 1251 luminometer. Light units were converted to picograms (pg) of luciferase using a standard curve established by measuring the light units produced by purified firefly luciferase (Analytical Luminescence Laboratory) within control muscle extract. The RNA and DNA preparations prior to injection did not contain any contaminating luciferase activity. Control muscle injected with 20% sucrose had no detectable luciferase activity. All the above experiments were done two to three times and specifically, the DNA time points greater than 40 days were done three times.

Figure 3A:
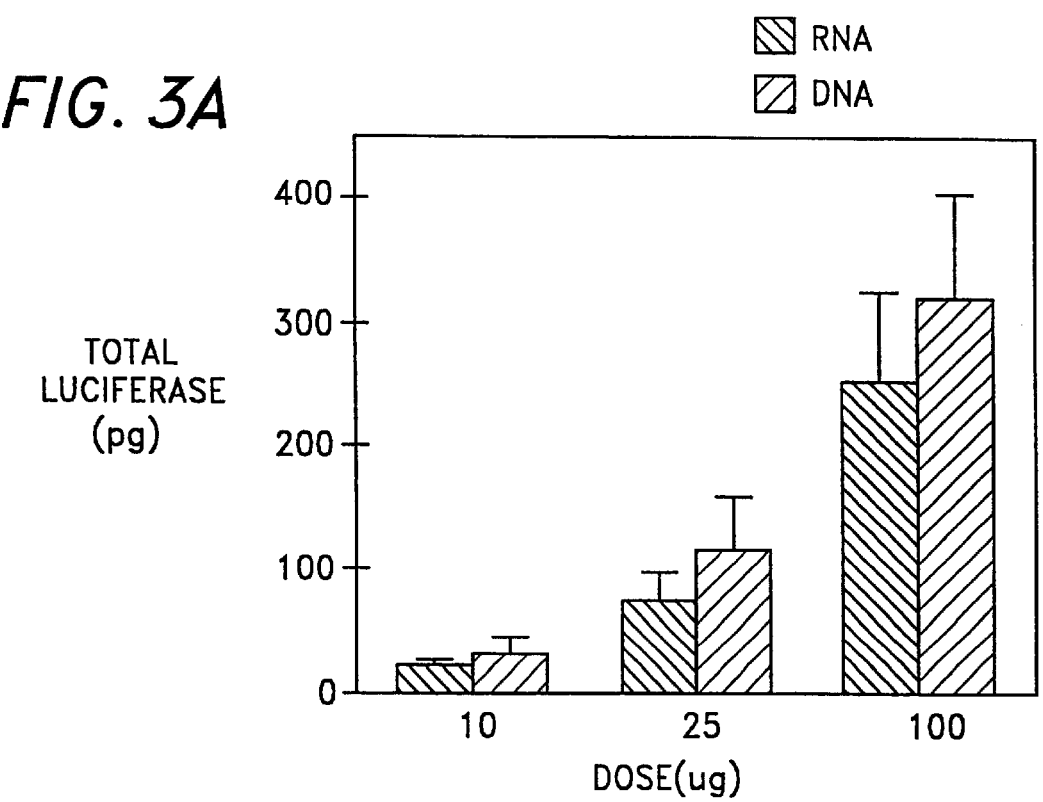
FIGS. 3A, 3B, and 3C present data for luciferase activity in muscle following the injection of $\beta gLuc\beta gA_n$ into muscle.
Figure 3B:
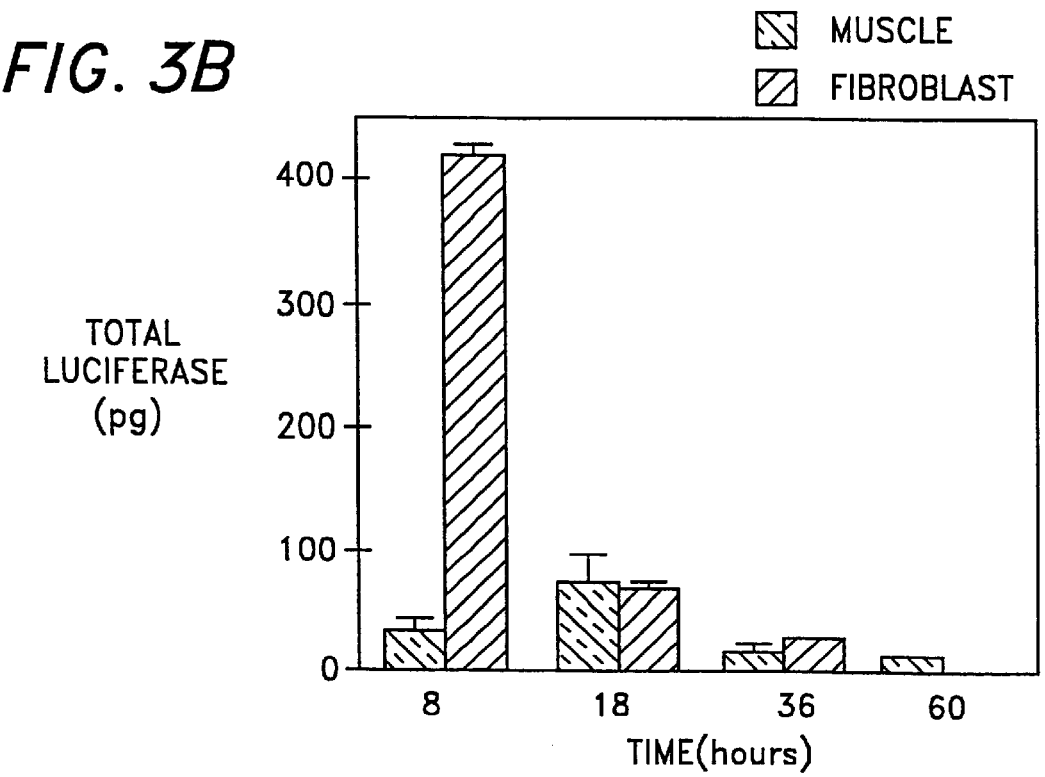
Figure 3C:
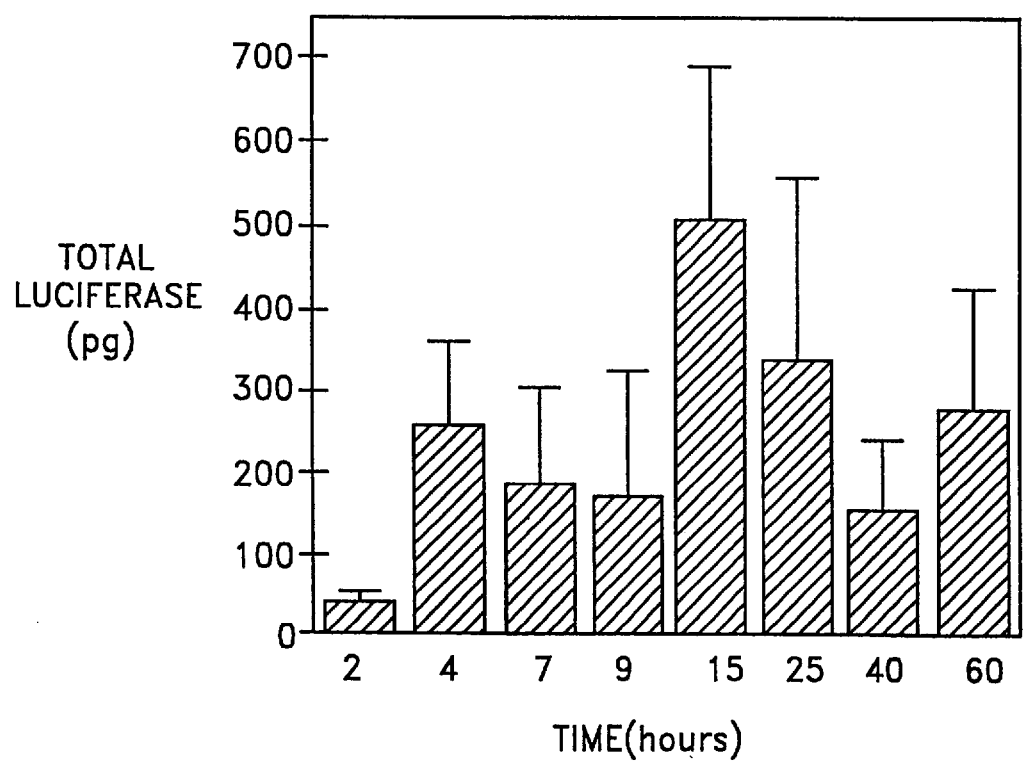

The FIGS. 3A to 3C illustrate the results of the following:

3(A) Luciferase activity measured 18 hours following the injection of varying amounts of βgLUCβA$_n$ RNA in 20% sucrose and 4 days following the injection of varying amounts of pRSVL in 20% sucrose 3(B) Luciferase activity assayed at varying times after 20 µg of βgLUCβA$_n$ RNA were lipofected into a million 3T3 fibroblasts (Malone, R. et al. *Proc. Nat'l. Acad. Sci. USA* 86:6077–6081 (1989), and after 100 µg of βgLUCβA$_n$ RNA in 20% sucrose were injected into quadriceps.

3(C) Luciferase activity assayed at varying times after pRSVL DNA was injected intramuscularly.

A. Level of Gene Expression

A dose-response effect was observed when quadriceps muscles were injected with various amounts of βgLucβA$_n$ RNA or DNA pRSVL constructs (FIG. 3A). The injection of ten times more DNA resulted in luciferase activity increasing approximately ten-fold from 33 pg luciferase following the injection of 10 µg of DNA to 320 pg luciferase following the injection of 100 µg of DNA. The injection of ten times more RNA also yielded approximately ten times more luciferase. A million 3T3 mouse fibroblasts in a 60 mm dish were lipofected with 20 µg of DNA or RNA complexed with 60 µg of Lipofectin™ (Bethesda Research Labs) in 3 ml of Opti-MEM™ (Gibco). Two days later, the cells were assayed for luciferase activity and the results from four separate plates were averaged. Twenty pg of pRSVL DNA transfected into fibroblasts yielded a total of 120 pg of luciferase (6 pg luciferase/pg DNA), while 25 µg injected into muscle yielded an average of 116 pg of luciferase (4.6 pg luciferase/µg DNA; FIG. 3A). The expression from the RNA vectors was approximately seven-fold more efficient in transfected fibroblasts than in injected muscles. Twenty pg of βgLucβA$_n$ RNA transfected into fibroblasts yielded a total of 450 pg of luciferase, while 25 µg injected into muscle yielded 74 pg of luciferase (FIGS. 3A and 3B). Based on the amount of DNA delivered, the efficiency of expression from the DNA vectors was similar in both transfected fibroblasts and injected muscles.

B. Time Course of Expression

The time course was also investigated (FIGS. 3B and 3C). Luciferase activity was assayed at varying times after 25 µg of βgLucβA$_n$ RNA or 100 µg of pRSVL DNA were injected. Following RNA injection, the average luciferase activity reached a maximum of 74 pg at 18 hours, and then quickly decreased to 2 pg at 60 hours. In transfected fibroblasts, the luciferase activity was maximal at 8 hours. Following DNA injection into muscle, substantial amounts of luciferase were present for at least 60 days.

The data in FIG. 3B suggest that luciferase protein and the in vitro RNA transcript have a half-life of less than 24 hours in muscle. Therefore, the persistence of luciferase activity for 60 days is not likely to be due to the stability of luciferase protein or the stability of the in vivo RNA transcript.

EXAMPLE 14

Persistence of DNA in Muscle Following Injection as Determined by Southern Blot Analysis Preparations of muscle DNA were obtained from control, uninjected quadriceps or from quadriceps, 30 days after injection with 100 µg of pRSVL in 20% sucrose. Two entire quadriceps muscles from the same animal were pooled, minced into liquid N$_2$ and ground with a mortar and pestle. Total cellular DNA and HIRT supernatants were prepared (F. M. Ausubel et al.(Eds) *Current Protocols in Molecular Biology*, John Wiley, New York (1987). Fifteen µg of the total cellular DNA or 10 µl out of the 100 µl of HIRT supernatant were digested, run on a 1.0% agarose gel, transferred to Nytran™ (Schleicher and Schuell, New York), using a vacublot apparatus (LKB) and hybridized with multiprimed $^{32}$P-luciferase probe (the HindIII-BamHI fragment of pRSVL). Following hybridization overnight, the final wash of the membrane was with 0.2×SSC containing 0.5% SDS at 68° C. Kodak XAR5 film was exposed to the membrane for 45 hours at −70° C.

Figure 4:
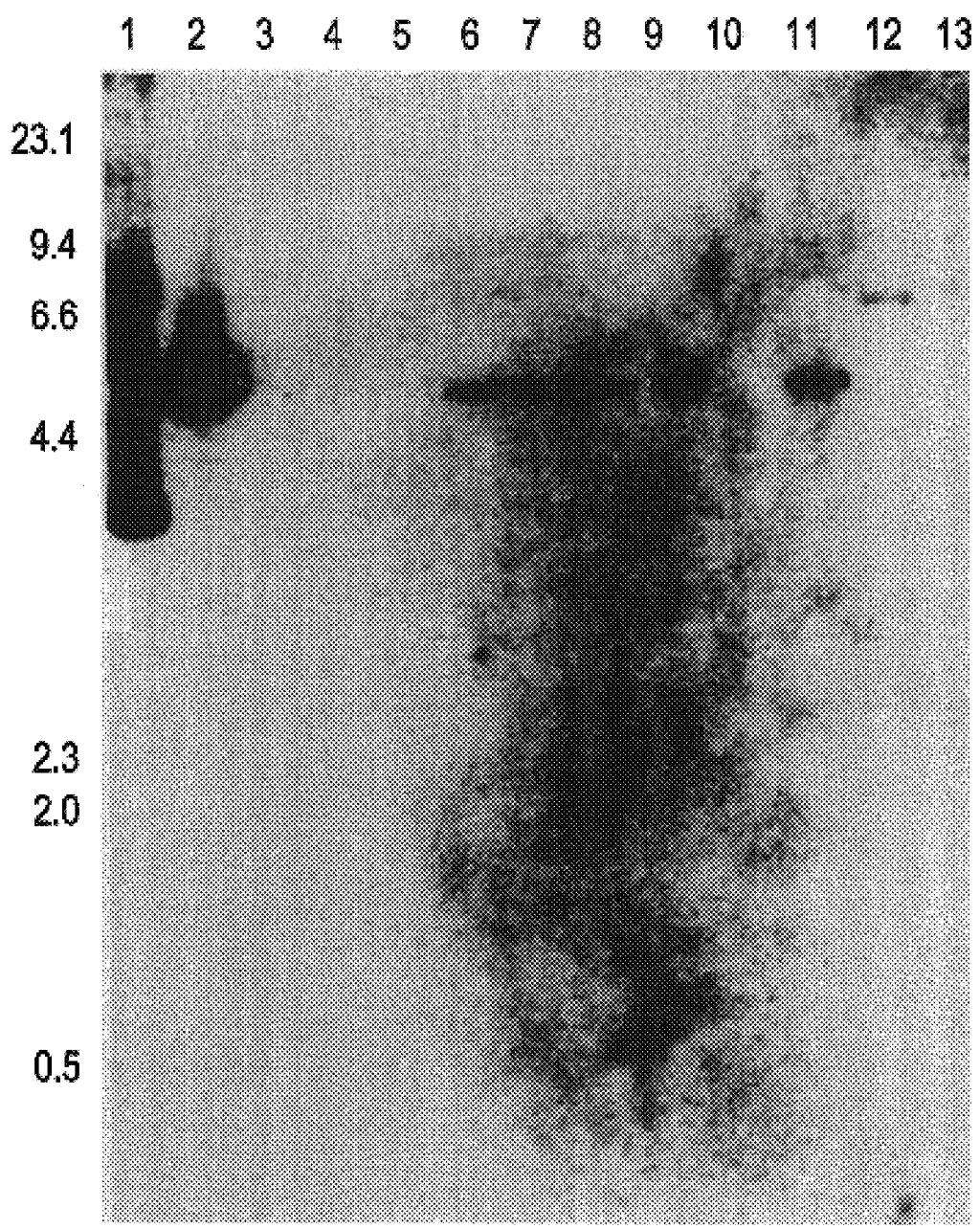
FIG. 4 presents an autoradiogram of a Southern blot after analysis of extracts from pRSVL-injected muscle.

FIG. 4 is an autoradiogram of a Southern blot having a sample pattern as follows:

Lane 1: 0.05 ng of undigested pRSVL plasmid

Lane 2: 0.05 ng of BamH1 digested pRSVL

Lane 3: Blank

Lane 4: BamH1 digest of HIRT supernatant from control muscle

Lane 5: BamH1 digest of cellular DNA from control, uninjected muscle

Lanes 6, 7: BamH1 digest of HIRT supernatant from two different pools of pRSVL injected muscles Lanes 8, 9: BamH1 digest of cellular DNA from two different pools of pRSVL injected muscle Lane 10: Cellular DNA (same as Lane 9) digested with BamH1 and Dpn1

Lane 11: Cellular DNA (Same as in Lane 9) digested with BamH1 and Mbo1

Lane 12: Cellular DNA digested with BgIII

Lane 13: HIRT supernatant digested with BgIII (Size markers (λ/HindIII) are shown at the left).

Southern blot analysis of muscle DNA indicates that the foreign pRSVL DNA is present within the muscle tissue for at least 30 days (FIG. 4, lanes 6–9) and is similar to the levels of DNA present in muscle two and 15 days following injection. In muscle DNA digested with BamHI (which cuts pRSVL once; FIG. 4, lanes 6–9), the presence of a 5.6 kb band that corresponds to linearized pRSVL (FIG. 4, lane 2) suggest that the DNA is present either in a circular, extrachromosomal form or in large tandem repeats of the plasmid integrated into chromosome. In muscle DNA digested with BgIII (which does not cut pRSVL), the presence of a band smaller than 10 kb (FIG. 4, lanes 12 and 13) and at the same size as the open, circular form of the plasmid pRSVL (FIG. 4, lane 1) implies that the DNA is present extrachromosomally in an open, circular form. The appearance of the pRSVL DNA in HIRT supernatants (FIG. 4, lanes 6, 7, and 13) and in bacteria rendered ampicillin-resistant following transformation with HIRT supernatants also suggest that the DNA is present unintegrated. Although the majority of the exogenous DNA appears to be extrachromosomal, low levels of chromosomal integration cannot be definitively excluded. Overexposure of the blobs did not reveal smears of hybridizing DNA larger than the 10 kb that would represent plasmid DNA integrated at random sites. The sensitivity of the pRSVL DNA is muscle to DPNI digestion (FIG. 4, lane 10) and its resistance to MboI digestion (FIG. 4, lane 11), suggests that the DNA has not replicated within the muscle cells.

EXAMPLE 15

In vivo Expression of Pure DNA Implanted Directly into the Muscle of Mice pRSVL DNA was precipitated in ethanol and dried. The pellet was picked up with fine forceps and deposited into various muscle groups as described in the preceding examples. Five days later the muscle was analyzed for luciferase activity as described in Example 13. The DNA was efficiently expressed in different muscle groups as follows:

| Implant: | Luciferase Activity (Light Units, LU): | | | |
|---|---|---|---|---|
| 25 μg pRSVL DNA | Control | Biceps | Calf | Quadriceps |
| | 428 | 46420 | 27577 | 159080 |
| | 453 | 53585 | 34291 | 35512 |
| | | 1171 | 106865 | |
| | | 53397 | 105176 | |
| | | 499 | 40481 | |

EXAMPLE 16

Direct Gene Delivery into Lung: Intratracheal Injection of DNA, DNA/Cl Complexes or Pure Protein The DNA luciferase vector (pRSVL), complexed with Lipofectin™, was injected intratracheally into rats either in 20% sucrose (2 rats) or in 5% sucrose (6 rats). Two days following the injection, the rat lungs were divided into 7 sections: LUL, LLL, RUL, RML, RLL, AL, (defined as follows) and Trachea. The rat lung differs from that of the human in having one large left lung off the left main bronchus. The left lung for this study was cut in half into a left upper part (LUL) and left lower part (LLL). The right lung contains 4 lobes: right cranial lobe (RUL), right middle lobe (RML), right lower lobe ((RLL), and an accessory lobe (AL). Extracts were prepared by mincing these lung parts into separate 1.5 ml microtubes containing 200 μl of a lysis solution (20 mM Tris, pH 7.4, 2 mM $MgCl_2$ and 0.1% Triton X), and grinding the lung with a plastic pestle. (Kontes) for one minute. In order to ensure complete disruption of the lung cells, the lung tissue was then placed under 600 psi of $N_2$ in a Parr bomb at 4° C. for 15 minutes before releasing the pressure. Luciferase assays were done on 87.5 μl of lung extract out of a total volume of about 350 μl.

| Injection | RUL | RLL | LUL | LML | LLL | AL | Trachea |
|---|---|---|---|---|---|---|---|
| Mock | 22.6 | 22.4 | 21.9 | 21.3 | 20.1 | 19.8 | — |
| 25 μg DNA alone | 21.2 | 21.5 | 21.8 | 21.6 | 21.9 | 21.2 | — |
| 25 μg DNA alone | 21.7 | 21.4 | 21.3 | — | 22.2 | 21.5 | — |

-continued

| Injection | RUL | RLL | LUL | LML | LLL | AL | Trachea |
|---|---|---|---|---|---|---|---|
| 250 μg DNA alone | 21.7 | 23.2 | 21.9 | 28.5 | 22.6 | 22.0 | 21.3 |
| 250 μg DNA alone | 22.9 | 22.5 | <u>33.3</u> | 23.0 | <u>25.4</u> | 24.3 | 21.5 |
| 250 μg DNA alone | 21.8 | 21.5 | 21.8 | 20.4 | 20.7 | 20.8 | 20.7 |
| 25 μg DNA/CL | 20.8 | 22.2 | 19.6 | 22.3 | 22.3 | 22.0 | — |
| 25 μg DNA/CL | 22.9 | 22.0 | 22.7 | 21.7 | 22.8 | — | 22.18 |
| 25 μg DNA/CL | 22.2 | 23.8 | 22.1 | 23.9 | 22.8 | — | 21.6 |
| 25 μg DNA/CL | 20.9 | 20.9 | 20.9 | 20.6 | 20.3 | — | 19.3 |
| 25 μg DNA/CL | 19.8 | 20.0 | 20.3 | 20.2 | 20.1 | 20.3 | 20.1 |
| 25 μg DNA/CL | 20.5 | 20.5 | 19.8 | 19.5 | 19.9 | 19.9 | 19.8 |
| Luc Protein $3 \times 10^4$ 1.u. | 105.3 | 77.1 | 98.7 | 80.0 | 86.3 | 89.6 | 178.9 |
| Blank | 22.5 | | | | | | |

Mock: Values are those for an animal that received 25 μg of DNA in 0.3 ml 20% sucrose into the esophagus. (A sample containing only water yields 22.5 l.u.)

25 μg DNA alone: represent separate animals that received intratracheal injections of 25 μg of pPGKLuc in 0.3 ml 20% sucrose.

25 μg DNA/CL: represent separate animals that received intratracheal injections of 25 Mg of pPGKLuc complexed with Lipofectin™ in 0.3.ml 5% sucrose.

The above animals were sacrificed and lung extracts prepared 2 days after injection.

Luc Protein 104 l.u.: represents an animal that received the equivalent of 30,000 light units (l.u.) of purified firefly luciferase (Sigma), and then was immediately sacrificed.

The luciferase activity in the 25 μg DNA alone and the 25 μg DNA/CL groups of animals were not greater than that in the mock animal; however, in the 250 μg DNA alone animals, three lung sections showed small but reliably elevated l.u. activity. above control lung or blanks (Bold, underlined). Duplicate, assays on the same extract confirmed the result. Experience with the LKB 1251 luminometer indicates that these values, although just above background, indicate real luciferase activity.

EXAMPLE 17

Luciferase Activity in Mouse Liver Directly Injected with DNA Formulations

The DNA luciferase expression vector pPGKLuc was injected intrahepatically (IH) into the lower part of the left liver lobe in mice. The pPGKLuc DNA was either injected by itself (450 Mg DNA in 1.0 ml 20% sucrose) or complexed with Lipofectin™ (50 μg DNA+150 μg Lipofectin™ in 1.0 ml 5% sucrose). Three days following injection, the left liver lobe was divided into two sections (a lower part where the lobe was injected and an upper part of the lobe distant from the injection site) and assayed for luciferase activity as described in the preceding examples.

| Mice Intrahepatic Liver Injection | Luciferase Activity (Light Units, LU) | |
|---|---|---|
| | Lower | Upper |
| Blank (20.2 LU) | | |
| Control: 20% Sucrose Only | 20.8 | 23.8 |
| 50 μg pPGKLuc + Lipofectin | 35.4 | 23.1 |
| 50 μg pPGKLuc + Lipofectin | 38.1 | 21.4 |

-continued

| Mice Intrahepatic Liver Injection | Luciferase Activity (Light Units, LU) | |
|---|---|---|
| | Lower | Upper |
| 50 µg pPGKLuc + Lipofectin | 22.1 | 22.7 |
| 450 µg pPGKLuc | 43.7 | 29.2 |
| 450 µg pPGKLuc | 78.8 | 21.7 |
| 450 µg pPGKLuc | 21.7 | 20.8 |

Two of the three animals that received the pure pPGKLuc injections and two of the three animals that received pPGKLuc+Lipofectin™ injections had luciferase activity significantly above background (bold, underlined). The lower part of the liver lobe, which was directly injected, had larger amounts of luciferase activity than the upper part, which was distant from the injection site. Similar results have been obtained using pRSVCAT DNA expression vector and CAT assays. Luciferase activity was not detected three says after similar preparations of pPGKLuc (+ and −Lipofectin™) were injected into the portal circulation of rats.

EXAMPLE 18

Expression of Growth Hormone Gene Injected into Liver and Muscle

Mice were injected with the pXGH5 (metalothionien promoter-growth hormone fusion gene) (Selden Richard et al., *Molec. Cell Biol.* 6:3173–3179 (1986)) in both liver and muscle. The mice were placed on 76 mM zinc sulfate water. Later the animals were bled and the serum analyzed for growth hormone using the Nichols GH Kit.

A. Two mice were injected with 20 µg of pXGH5 gene complexed with 60 µg/ml of Lipofectin in 5% sucrose. One ml of this solution was injected into the liver and the ventral and dorsal abdominal muscles were injected with 0.1 ml in 7 sites two times. Two days later, the animals were bled. The serum of one animal remained at background level, while that of the other contained 0.75 ng/ml growth hormone.

B. Three mice were injected with 0.1 ml of 1 mg/ml of pXGH5 in 5% sucrose, 2× in the quadriceps, 1× in the hamstring muscle, 1× in pectoralis muscle, and 1× in trapezoid muscles on two separate days. The results were as follows:

| Animal No. | Growth Hormone(ng/ml):Day 1 | Day 2 |
|---|---|---|
| 1 | 0.6 | 0.6 |
| 2 | 0.8 | 1.0 |
| 3 | 0.95 | 0.8 |
| Background: 0.5 ng/ml | | |

EXAMPLE 19

Figure 5A:
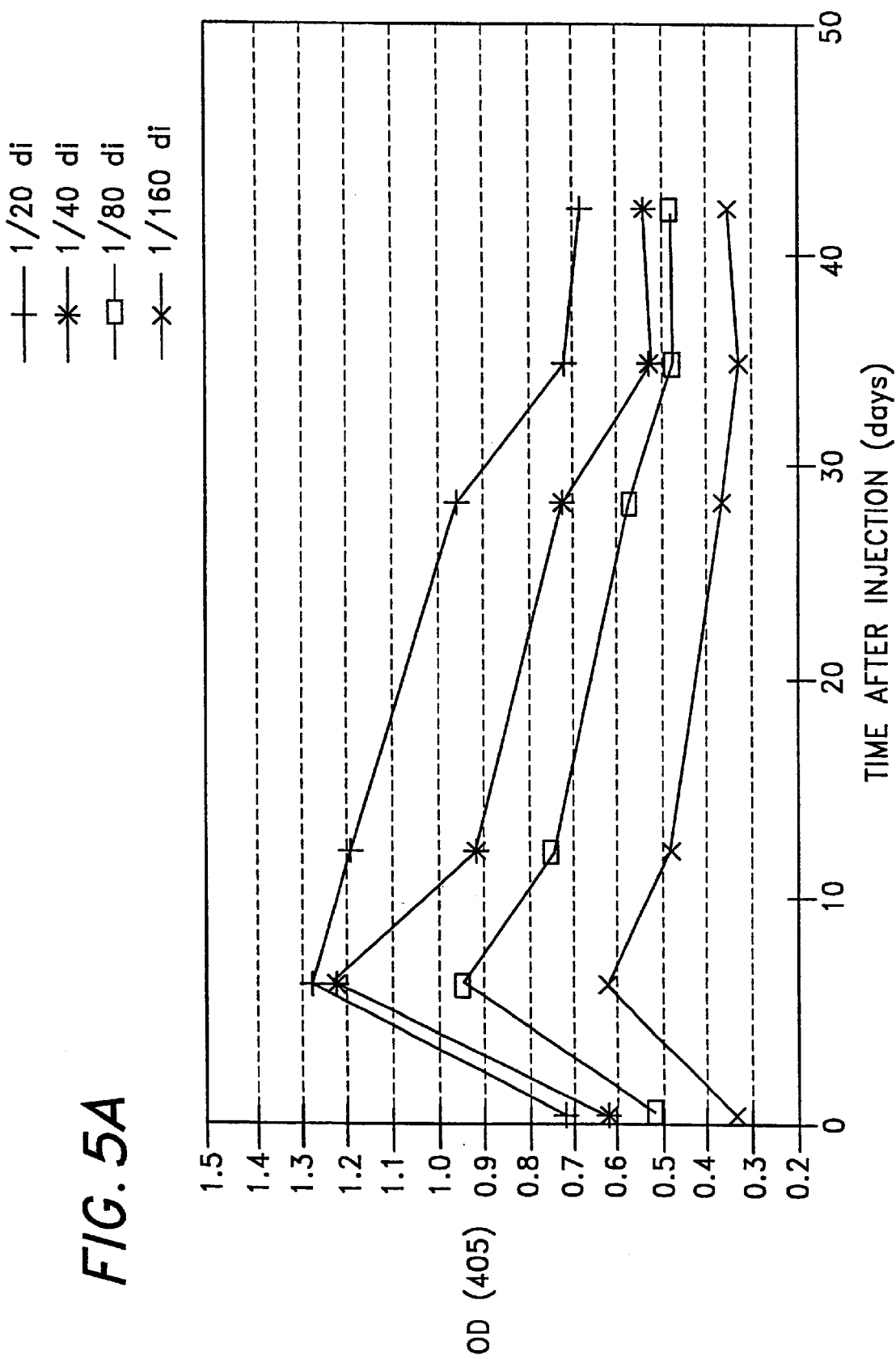
FIGS. 5A and 5B comprise graphs showing antibody production in mice following the injection of a gene for an immunogenic peptide.
Figure 5B:
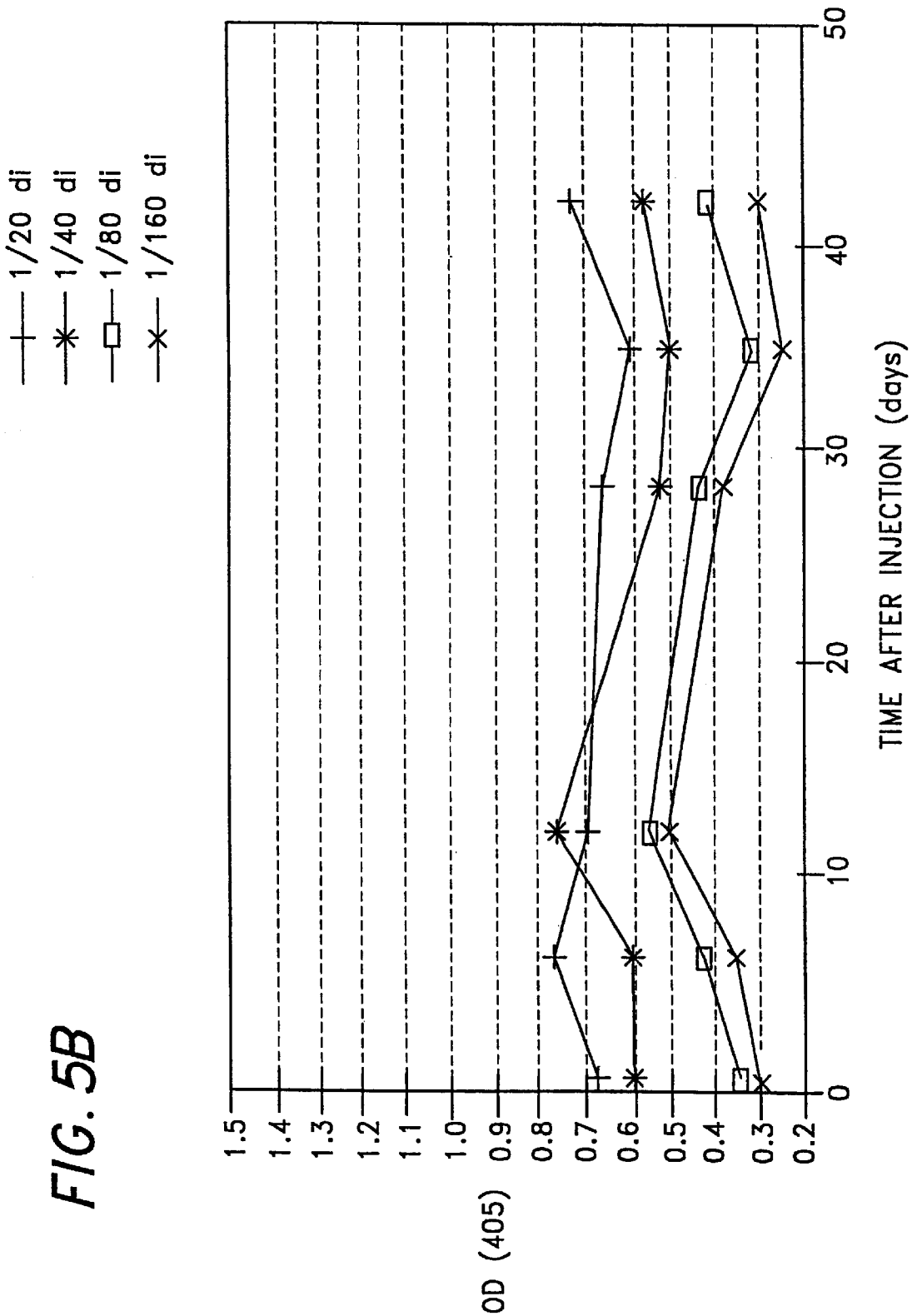

Antibody Production in Mice Directly Injected with a Gene for an Immunizing Peptide Mice were injected with a quantity of 20 µg of a plasmid construct consisting of the gp-120 gene, driven by a cytomegalovirus (CMV) promotor. The DNA was injected into the quadriceps muscle of mice according to the methods described in Example 11. Mouse 5 (FIG. 5A) was injected in the quadriceps muscle with 20 µg of plasmid DNA in isotonic sucrose. Mouse 2 (FIG. SB) was injected with sucrose solution alone. Blood samples were obtained prior to the injection (Day 0) at the times indicated on FIG. 5, up to more than 40 days post injection. The serum from each sample was serially diluted and assayed in a standard ELISA technique assay for the detection of antibody, using recombinant gp-120 protein made in yeast as the antigen. Both IgG and IgM antibodies were detected. The study indicates that the gene retains its signal sequence, and the protein is efficiently excreted from cells.

EXAMPLE 20

Figure 6A:
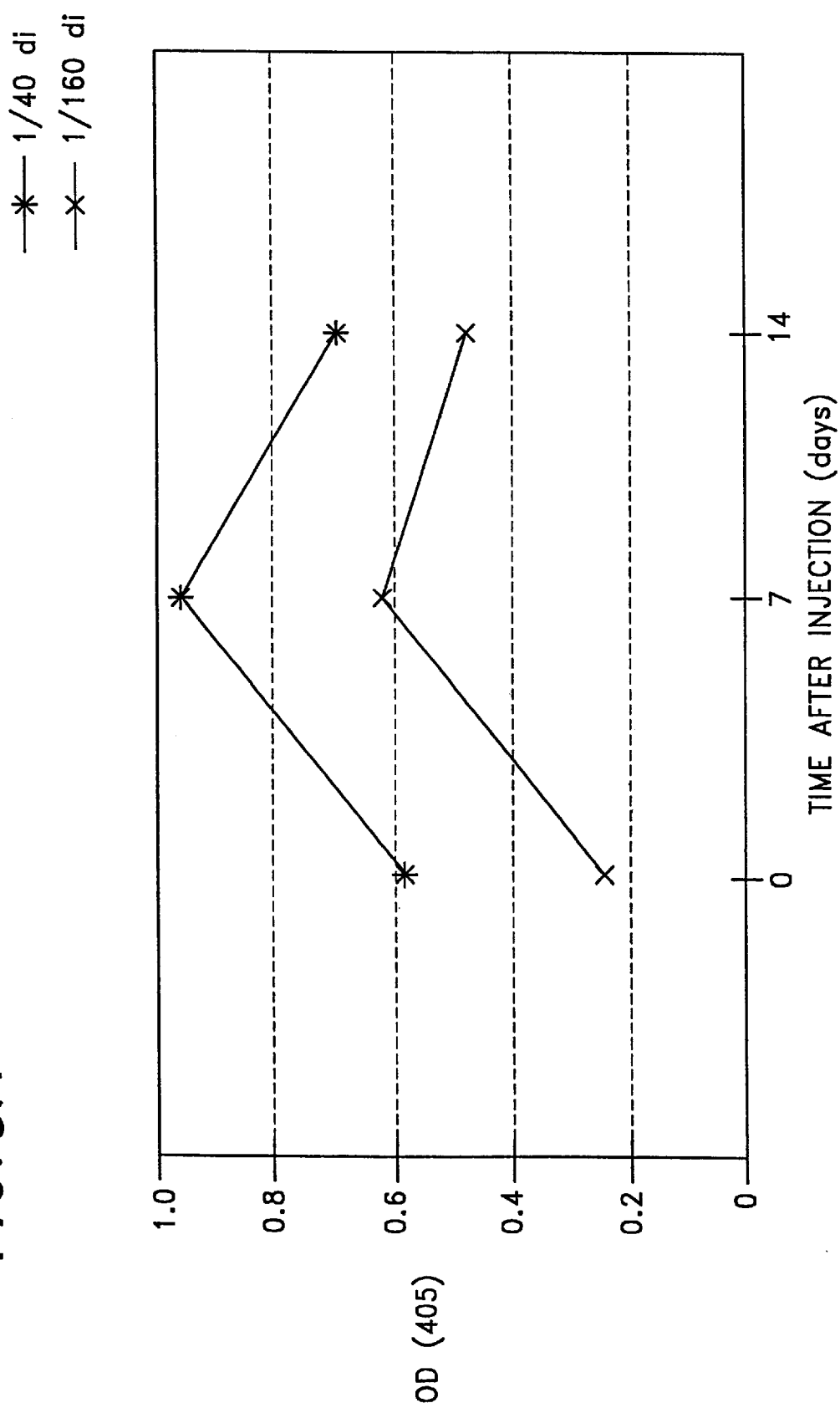
FIGS. 6A and 6B comprise graphs showing antibody production in mice following the injection of mouse cells transfected with a gene for an immunogenic peptide.
Figure 6B:
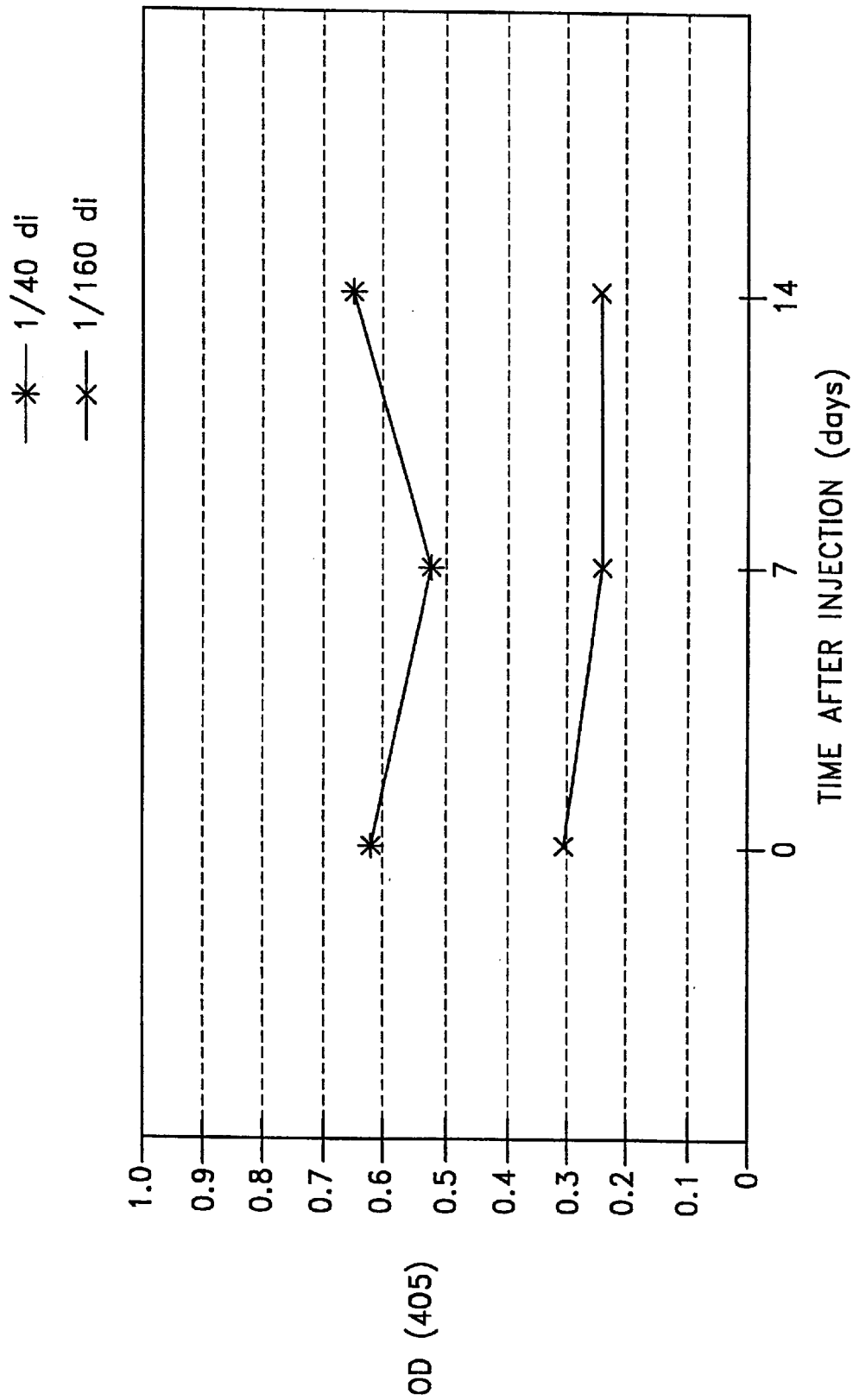

Antibody Production in Mice Injected with Cells Transfected with a Gene for an Immunizing Peptide The cell line BALB/C C1.7 (TIB 80) was obtained from the American Type Tissue Culture Collection. These cells were transfected with the gp-120 gene construct described in Example 19. To 0.75 ml OptiMEM™ (Gibco. Inc.) were added 6.1 µg of DNA. The quantity of 30 µg of cationic liposomes (containing DOTMA and cholesterol in a 70:30 molar ratio) were added to another 0.75 ml OptiMEMM™. The mixtures were combined and 1.5 ml or OptiMEM™ containing 20% (v/v) fetal bovine calf serum was added. This solution was poured into a 60 mm plastic petri dish containing 80% confluent cells (approximately one million total cells per plate). At 3.2 hours after lipofection, the cells were detached from the plate with trypsin and EDTA treatment, washed with OptiMEM™ and resuspended in 0.1 ml OptiMEM™ with 10% fetal calf serum. These cells were injected (IP) into mice. Mouse I2 (FIG. 6A) was injected with the transfected cells. Mouse I1 (FIG. 6B) received an identical number of untransfected cells. Blood samples were obtained prior to the injection (Day 0) and at the times indicated in FIGS. 6A and 6B. The serum samples were processed as in the preceding example. Both IgG and IgM antibodies were detected as indicated in FIGS. 6A and 6B.

EXAMPLE 21

Use of Uncapped 5 Sequences to Direct Translation of DNA Transfected into Cells in vitro Two different DNA templates were constructed, both of which code for the synthesis of RNA that express the *E. coli.* β-galactosidase reporter gene. A Lac-Z gene that contains the Kozak consensus sequence was inserted in place of the luciferase coding sequences of the pβGLucβGA$_n$ template to generate the pβGLacZβGA$_n$ template. The pEMCLacZβGA$_n$ template was made by replacing the 5' β-globin untranslated sequences of pβGLacZβGA$_n$ with the 588 bp EcoRI/NcoI fragment from the encephalomyocarditis virus (EMCV). (See construction of plasmid pE5LVPO from DNA of plasmid pE3T11 in Parks, et al., *J. Virology* 60:376–384, at 378 (1986)). These EMC 5' untranslated sequences had previously been shown to be able to initiate efficient translation in vitro in reticulocyte lysates. We demonstrated that these sequences can also direct efficient translation when transfected into fibroblasts in culture. The percentage of blue cells was slightly greater in cells transfected with the uncapped EMCLacZ↑GA$_n$ RNA than in cells transfected with the capped pEMCLacZβGA$_n$ RNA. Transfection with either uncapped or capped pEMCLacZβGA$_n$ RNA yielded a greater number of positive β-galactosidase cells than transfection with capped βGLacZβGA$_n$ RNA. It has recently been shown that this EMC 5' untranslated sequence, as a component of vaccinia-T7 polymerase vectors, can increase translation of an uncapped mRNA 4 to 7-fold (Elroy-Stein, O. et al., *Proc. Natl. Acad. Sci. USA* 86:6126–6130 (1989)). These EMC sequences thus have the ability to direct efficient translation from uncapped messengers.

EXAMPLE 22

T7 Polymerase Transcription in Transfected Cell Cultures

An SV40-T7 polymerase plasmid containing T7 polymerase protein expressed off the SV40 promotor (Dunn, J. et al., *Gene* 68: 259 (1988)) was co-lipofected with the pEMCLacZβGA$_n$ template DNA into 3T3 fibroblasts in culture to demonstrate that T7 polymerase transcription can occur via plasmids. Two different SV40-T7 polymerase expression vectors were used:

(a) pSV-G1-A: pAR3126-SV40 promotor driving expression of T7 polymerase protein which is directed to the cytoplasm.

(b) pSVNU-G1-A: pAR3132-SV40 promotor driving expression of T7 polymerase protein which is directed to the cytoplasm.

Each of these two plasmids were co-lipofected with pEMCLacZβGAn at 1:3 and 3:1 ratios into a 60 mm plates of 3T3 cells. The number of blue β-galactosidase cells were counted and scored as indicated below.

| β-gal template | Ratio: template/ polymerase vector | Co-Lipofectant: pSV-G1-A | pSVNU-G1-A |
|---|---|---|---|
| βGLacZβGAn | 3:1 | 0 | 1 |
|  | 1:3 | 0 | 1 |
| EMCLacZβGAn | 3:1 | 74 | 70 |
|  | 1:3 | 45 | 15 |

EXAMPLE 23

Expression of Luciferase in Brain Following Directed Injection of Messenger RNA Two adult mice and one newborn mouse were injected with the βgLucβgA$_n$ mRNA containing the 5' cap and prepared according to Example 13. In the adult mice, injections were from a stock solution of mRNA at 3.6 µg/µl in 20% sucrose; injection volumes were 5 µl, 2 injections into each of the bilateral parietal cortex, 4 injections per mouse. Tissue was assayed at 18 hours post injection, according to Example 13 using 200 µl of brain homogenate, disrupted in a Parr bomb, and 87.5 µl was taken for assay. The results are as follows:

|  |  | Hemisphere: | |
|---|---|---|---|
| Treatment | Animal I.D. | Left | Right |
| Sham Injection | AMra | 649 | 629 |
| βgLucβgA$_n$ | AMrb | 1,734 | 1,911 |
| βgLucβgA$_n$ | NRr | 1,569 | 963 |

The newborn mouse was injected with 1 µl βgLucβgA$_n$ (3.6 µg/µl; 20% sucrose) into the bilateral forebrain and tissues were similarly processed and analyzed.

EXAMPLE 24

Functional Expression of Dystrophin in Dystrophic Mouse Muscle in vivo

A plasmid containing the dystrophin gene under control of the Rous Sarcoma virus promoter was prepared from the Xp21 plasmid containing the complete dystrophin coding region and the SV40 poly A segment, which was cloned by Kunkel and colleagues. (Brumeister M., Monaco A P, Gillard Kunkel and colleagues. (Brumeister, et al., *Genomics* 3:189–202 (1988); Hoffman and Kunkel, *Neuron* 2:1019–1029 (1989); Koenig, et al., *Cell* 53:219–226 (1988)). 200 µg of the plasmid in 100 µl of phosphate buffered saline was injected into the quadriceps the mutant mouse strain lacking the dystrophin gene product (MDX mouse; Jackson labs). Expression of functional dystrophin was monitored 7 days post injection by immunohistochemistry according to the procedures described by Watkins et al. and using the same anti-dystrophin antibody (anti-60 kd antibody with a fluorescent secondary antibody) obtained from Kunkel. Functional expression of the dystrophin gene product in the dystrophic mice was detected by comparing the pattern of fluorescence observed in cross-sections of quadriceps muscle from injected animals, with the fluorescence pattern observed in normal animals. (Watkins S. C., Hoffman E. P., Slayter H. S., Kinkel L. M., Immunoelectron microscopic localization of dystrophin in myofibres. Nature 1988, June 30; 333 (6176:863–6). Normal dystrophin expression is localized underneath the plasma membrane of the muscle fiber, so that a cross section of the quadriceps muscle give a fluorescence pattern encircling the cell. In addition dystrophin expression was quantitated by Western blot analysis using the affinity purified anti-60kd antibody.

EXAMPLE 25

Adminstration of the Correcting Dystrophin Gene Directly into the Muscle of Patients with Duchenne's Muscular Dystrophy Patients with muscular dystrophy are given multiple 200 ug injections of plasmid containing the functional dystrophin gene (see previous example) in 100 ul of phosphate buffered saline. While under light anesthesia the patients are injected at 5 cm intervals into the entire skeletal muscle mass directly through the skin without surgery. Patient recovery evaluated by monitoring twitch tension and maximum voluntary contraction. In addition, biopsies of 300–500 muscle cells from an injected area are taken for histological examination, observing muscle structure and biochemical analysis of the presence of dystrophin, which is absent in patients with Duchenne's muscular dystrophy. Respiratory muscles, including the intercostal muscles which move the rib cage and the diaphragm, are particularly important impaired muscle groups in patients with muscular dystrophy. The intercostals can be reached by injection through the skin as can the other skeletal muscle groups. The diaphragm can accessed by a surgical procedure to expose the muscle to direct injection of plasmid DNA.

There will be various modifications, improvements, and applications of the disclosed invention that will be apparent to those of skill in the art, and the present application is intended to cover such embodiments. Although the present invention has been described in the context of certain preferred embodiments, it is intended that the full scope of these be measured by reference to the scope of the following claims.

What is claimed is:

1. A method of generating an immune response to a pathogen in a vertebrate, comprising:

administering in vivo into a tissue of a vertebrate in need of said immune response a composition consisting essentially of (a) a polynucleotide which directs synthesis of an immunogenic peptide or polypeptide in vertebrate cells, wherein said peptide or polypeptide is a pathogen-specific antigen;

(b) a pharmaceutically acceptable carrier; and optionally, (c) an adjuvant;

wherein said polynucleotide is a DNA plasmid operably encoding said immunogenic peptide or polypeptide through association with a promoter;

wherein said immune response is selected from the group consisting of a detectable antibody response, a detectable T-cell response, and a combination thereof;

wherein a sufficient amount of said composition is administered to allow incorporation of said polynucleotide into the cells of said vertebrate; and wherein sufficient expression of said immunogenic peptide or polypeptide occurs to generate said immune response in said vertebrate.

2. The method of claim 1, wherein said immune response is a detectable antibody response.

3. The method of claim 1, wherein said immune response is a detectable T-cell response.

4. The method of claim 3, wherein said immune response is a detectable cytotoxic T-cell response.

5. The method of claim 1, wherein said immune response is a combination of a detectable antibody response and a detectable T-cell response.

6. The method of claim 1, wherein said immunogenic peptide or polypeptide is metabolically incorporated into the cell membranes of said mammal in conjunction with one or more molecules selected from the group consisting of a class I major histocompatibility antigen, a class II major histocompatibility antigen, and a combination of class I and class II major histocompatibility antigens.

7. The method of claim 1, wherein said promoter is selected from the group consisting of a Rous sarcoma virus long terminal repeat (RSV LTR), a myeloproliferative sarcoma virus long terminal repeat (MPSV LTR), a simian virus 40 immediate early promoter (SV40 IEP), a metallothionein promoter, and a human cytomegalovirus immediate early promoter (CMV IEP).

8. The method of claim 1, wherein said composition is introduced into mucous membrane tissue.

9. The method of claim 1, wherein said composition is introduced into muscle.

10. The method of claim 1, wherein said composition is introduced into skin.

11. The method of claim 1, wherein said composition is injected.

12. The method of claim 1, wherein said administration is intramuscular, intravenous, intradermal, subcutaneous, or intranasal.

13. The method of claim 12, wherein said administration is intravenous.

14. The method of claim 12, wherein said administration is intranasal.

15. The method of claim 12, wherein said administration is intramuscular.

16. The method of claim 12, wherein said administration is intradermal.

17. The method of claim 12, wherein said administration is subcutaneous.

18. The method of claim 1, wherein said pathogen is a virus.

19. The method of claim 18, wherein said immunogenic peptide or polypeptide is selected from the group consisting of a viral glycoprotein and a viral coat protein.

20. The method of claim 19, wherein said virus is selected from the group consisting of a herpesvirus and a hepatitis B virus.

21. The method of claim 1, wherein said vertebrate is a mammal.

22. The method of claim 21, wherein said mammal is a human.

23. The method of claim 1, wherein the vertebrate is a bird.

24. The method of claim 1, wherein the vertebrate is a fish.

25. The method of claim 1, wherein said immune response is preventative.

26. The method of claim 1, wherein said immune response is ameliorative.

* * * * *